(12) United States Patent
Van der Lee et al.

(10) Patent No.: US 11,008,400 B2
(45) Date of Patent: May 18, 2021

(54) ANTI-5T4 ANTIBODIES AND ANTIBODY-DRUG CONJUGATES

(71) Applicant: Byondis B.V., Nijmegen (NL)

(72) Inventors: Miranda Maria Cornelia Van der Lee, Nijmegen (NL); Gerardus Joseph Andreas Ariaans, Nijmegen (NL); Jan Schouten, Nijmegen (NL); Marion Blomenrohr, Nijmegen (NL); Patrick Gerhard Groothuis, Nijmegen (NL); Rudy Gerardus Elisabeth Coumans, Nijmegen (NL)

(73) Assignee: Byondis B.V., Nijmegen (NL)

( * ) Notice: Subject to any disclaimer, the term of this patent is extended or adjusted under 35 U.S.C. 154(b) by 213 days.

(21) Appl. No.: 15/778,759

(22) PCT Filed: Nov. 24, 2016

(86) PCT No.: PCT/EP2016/078642
§ 371 (c)(1),
(2) Date: May 24, 2018

(87) PCT Pub. No.: WO2017/089447
PCT Pub. Date: Jun. 1, 2017

(65) Prior Publication Data
US 2019/0194346 A1  Jun. 27, 2019

(30) Foreign Application Priority Data

Nov. 24, 2015 (EP) ..................................... 15195978
Sep. 29, 2016 (EP) ..................................... 16191272

(51) Int. Cl.
*C07K 16/32* (2006.01)
*C07K 16/30* (2006.01)
(Continued)

(52) U.S. Cl.
CPC ............ *C07K 16/32* (2013.01); *A61K 31/437* (2013.01); *A61K 39/44* (2013.01); *A61K 45/06* (2013.01);
(Continued)

(58) Field of Classification Search
None
See application file for complete search history.

(56) References Cited

U.S. PATENT DOCUMENTS 8,044,178 B2  10/2011  Boghaert et al.

FOREIGN PATENT DOCUMENTS

WO   WO89/07947      9/1989
WO   WO2005/084390   9/2005
(Continued)

OTHER PUBLICATIONS

Fan et al. Breast Cancer Res. 2012; 14: R116 and Brersky et al. PNAS 2009; 106: 17864-17869).
Doronina et al. Bioconjugate Chem. 17 (2006): 114-124.
Brezski et al. "Tumor-associated and microbial proteases compromise host Ig effector functions by a single cleavage proximal to the hinge" GPNAS 2009; 106: 17864-17869.
(Continued)

*Primary Examiner* — Karl J Puttlitz
(74) *Attorney, Agent, or Firm* — Buscher Patent PLLC

(57) ABSTRACT

The present disclosure relates to CDR defined antibodies targeting the 5T4 oncofoetal antigen (TPBG, 5T4, Wnt Activated Inhibitory Factor 1, WAIF1) which exhibit a binding affinity for human 5T4 antigen which is in the same order of magnitude as their affinity for cynomolgus monkey 5T4. Antibody-drug conjugates (ADCs), and their use in the treatment of human solid tumours and haematological malignancies are claimed.

20 Claims, 7 Drawing Sheets

Specification includes a Sequence Listing.

(51) Int. Cl.

| | | |
|---|---|---|
| *A61K 47/60* | (2017.01) | |
| *A61K 47/54* | (2017.01) | |
| *A61K 47/68* | (2017.01) | |
| *A61K 39/44* | (2006.01) | |
| *A61K 45/06* | (2006.01) | |
| *A61P 35/00* | (2006.01) | |
| *A61K 31/437* | (2006.01) | |

(52) U.S. Cl.
CPC ............ *A61K 47/546* (2017.08); *A61K 47/60* (2017.08); *A61K 47/6803* (2017.08); *A61K 47/6851* (2017.08); *A61K 47/6889* (2017.08); *A61P 35/00* (2018.01); *C07K 16/30* (2013.01); *C07K 2317/34* (2013.01); *C07K 2317/92* (2013.01)

(56) References Cited

FOREIGN PATENT DOCUMENTS

| | | |
|---|---|---|
| WO | WO2006/031653 | 3/2006 |
| WO | WO2006/034488 | 3/2006 |
| WO | WO2007/106744 | 9/2007 |
| WO | WO2011/133039 | 10/2011 |
| WO | WO2012/131527 | 10/2012 |
| WO | WO2015/155345 | 10/2015 |
| WO | WO2015/177360 | 11/2015 |
| WO | 2018215427 | * 11/2018 |

OTHER PUBLICATIONS

Le Franc, "The IMGT Unique Numbering for Immunoglobulins, T-Cell Receptors, and Ig-Like Domains" *The Immunologist*, 7/4 (1999), pp. 132-136.

B.Q. Shen et al. "Conjugation site modulates the in vivo stability and therapeutic activity of antibody-drug conjugates" nature biotechnology, vol. 30, No. 2, Feb. 2012.

J.R. Junutula et al., "Site-specific conjugation of a cytotoxic drug to an antibody improves the therapeutic index" Nature Biotechnology, vol. 26, No. 8, Aug. 2008.

F. Tian et al, "A general approach to site-specific antibody drug conjugates", Proceedings of the National Academy of Sciences, (Jan. 17, 2014), vol. 111, No. 5, pp. 1766-1771.

P. Sapra et al, "Long-term Tumor Regression Induced by an Antibody-Drug Conjugate That Targets 5T4, an Oncofetal Antigen Expressed on Tumor-Initiating Cells", Molecular Cancer Therapeutics, (Dec. 5, 2012), vol. 12, No. 1, pp. 38-47.

Forsberg G et al, "Therapy of Human Non-Small-Cell Lung Carcinoma Using Antibody Targeting of a Modified Superantigen", British Journal of Cancer, Nature Publishing Group, GB, (Jul. 6, 2001), vol. 85, No. 1, pp. 129-136.

P. Agarwal et al., "Site-Specific Antibody-Drug Conjugates: The Nexus of Bioorthogonal Chemistry, Protein Engineering, and Drug Development." Bioconjugate Chem., Feb. 18, 2015, 26(2), pp. 176-192.

D. Lu et al., "Semi-mechanistic Multiple-Analyte Pharmacokinetic Model for an Antibody-Drug-Conjugate in Cynomolgus Monkeys." Pharrn Res., Jun. 2015, 32(6), pp. 1907-1919.

* cited by examiner ns against the 5T4

SEQUENCE LISTING

<160> NUMBER OF SEQ ID NOS: 64

<210> SEQ ID NO 1
<211> LENGTH: 115
<212> TYPE: PRT
<213> ORGANISM: Oryctolagus cuniculus
<220> FEATURE:
<221> NAME/KEY: misc_feature
<223> OTHER INFORMATION: HC variable region of clone/well 789 - rabbit

<400> SEQUENCE: 1

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Trp
            20                  25                  30

Met Ser Trp Val Arg Gln Ala Pro Gly Lys Gly Leu Glu Trp Ile Gly
        35                  40                  45

Ile Ile Ala Gly Arg Gly Ser Thr Tyr Tyr Ala Ser Trp Ala Lys Gly
    50                  55                  60

Arg Cys Thr Ile Ser Lys Thr Ser Thr Val Asp Leu Lys Ile Thr
65                  70                  75                  80

Ser Pro Thr Thr Glu Asp Thr Ala Ala Tyr Phe Cys Ala Arg Val Ser
                85                  90                  95

Ser Ile Tyr Tyr Thr Phe Asn Leu Trp Gly Gln Gly Thr Leu Val Thr
            100                 105                 110

Val Ser Ser
        115

<210> SEQ ID NO 2
<211> LENGTH: 113
<212> TYPE: PRT
<213> ORGANISM: Oryctolagus cuniculus
<220> FEATURE:
<221> NAME/KEY: misc_feature
<223> OTHER INFORMATION: LC variable region of clone/well 789 - rabbit

<400> SEQUENCE: 2

Ala Gln Val Leu Thr Gln Thr Pro Ser Ser Val Ser Ala Ala Val Gly
1               5                   10                  15

Gly Thr Val Thr Ile Asn Cys Gln Ser Ser Gln Ser Val Tyr Ser Asn
            20                  25                  30

Asn Glu Leu Ser Trp Tyr Gln Gln Lys Pro Gly Gln Pro Pro Lys Leu
        35                  40                  45

Leu Ile Tyr Tyr Ala Ser Thr Leu Ala Ser Gly Val Pro Ser Arg Phe
    50                  55                  60

Lys Gly Ser Gly Ser Gly Thr Gln Phe Thr Leu Thr Ile Ser Gly Val
65                  70                  75                  80

Gln Ser Asp Asp Ala Ala Thr Tyr Tyr Cys Gln Gly Ser Tyr Tyr Ser
                85                  90                  95

Gly Ser Gly Trp Tyr Tyr Ala Phe Gly Gly Gly Thr Glu Val Val Val
            100                 105                 110

Lys

<210> SEQ ID NO 3
<211> LENGTH: 118
<212> TYPE: PRT
<213> ORGANISM: Oryctolagus cuniculus
<220> FEATURE:
<221> NAME/KEY: misc_feature
<223> OTHER INFORMATION: HC variable region of clone/well 811 - rabbit

<400> SEQUENCE: 3

Gln Ser Val Glu Glu Ser Gly Gly Arg Leu Val Thr Pro Gly Thr Ser
1               5                   10                  15

Leu Thr Leu Thr Cys Thr Ala Ser Gly Phe Ser Leu Ser Thr Tyr Ala
            20                  25                  30

Met Ile Trp Val Arg Gln Ala Pro Gly Lys Gly Leu Glu Trp Ile Gly
        35                  40                  45

Ile Ile Asn Ser Ser Gly Tyr Thr Tyr Tyr Ala Asn Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Gly Asn
                85                  90                  95

Ala Gly Ile Ser Tyr Asp Val Ser Phe Asn Leu Trp Gly Gln Gly Thr
            100                 105                 110

Leu Val Thr Val Ser Ser
        115

<210> SEQ ID NO 4
<211> LENGTH: 110
<212> TYPE: PRT
<213> ORGANISM: Oryctolagus cuniculus
<220> FEATURE:
<221> NAME/KEY: misc_feature
<223> OTHER INFORMATION: LC variable region of clone/well 811 - rabbit

<400> SEQUENCE: 4

Ala Tyr Asp Met Thr Gln Thr Pro Ala Ser Val Glu Ala Gly Val Gly
1               5                   10                  15

Gly Thr Val Thr Ile Asn Cys Gln Ala Ser Glu Ser Ile Ser Ser Trp
                20                  25                  30

Leu Ala Trp Tyr Gln Lys Pro Gly Gln Pro Pro Asn Leu Leu Ile
            35                  40                  45

Tyr Glu Ala Ser Lys Leu Ala Ser Gly Val Pro Ser Arg Phe Ser Gly
50                  55                  60

Ser Gly Ser Gly Thr Glu Phe Thr Leu Thr Ile Ser Gly Val Glu Ser
65                  70                  75                  80

Ala Asp Ala Ala Thr Tyr Tyr Cys Gln Gln Gly Trp Thr Ser Ser Asn
                85                  90                  95

Ile Asp Asn Ala Phe Gly Gly Gly Thr Glu Val Val Val Lys
            100                 105                 110

<210> SEQ ID NO 5
<211> LENGTH: 118
<212> TYPE: PRT
<213> ORGANISM: Oryctolagus cuniculus
<220> FEATURE:
<221> NAME/KEY: misc_feature
<223> OTHER INFORMATION: HC variable region of clone/well 825 - rabbit

<400> SEQUENCE: 5

Gln Ser Val Glu Glu Ser Gly Arg Leu Val Thr Pro Gly Thr Pro
1               5                   10                  15

Leu Thr Leu Thr Cys Thr Val Ser Gly Ile Asp Leu Ser Ser Tyr Gly
                20                  25                  30

Met Gly Trp Val Arg Gln Ala Pro Gly Lys Gly Leu Glu Tyr Ile Gly
            35                  40                  45

Ile Ile Ser Arg Asn Ser Val Thr Tyr Tyr Ala Thr Trp Ala Lys Gly
50                  55                  60

Arg Phe Thr Ile Ser Lys Thr Ser Thr Thr Val Asp Leu Lys Met Thr
65                  70                  75                  80

Ser Pro Thr Thr Glu Asp Thr Ala Thr Tyr Phe Cys Ala Arg Arg Ala
                85                  90                  95

Thr Tyr Ser Gly Ala Leu Gly Tyr Phe Asp Ile Trp Gly Pro Gly Thr
            100                 105                 110

Leu Val Thr Val Ser Phe
        115

<210> SEQ ID NO 6
<211> LENGTH: 110
<212> TYPE: PRT
<213> ORGANISM: Oryctolagus cuniculus
<220> FEATURE:
<221> NAME/KEY: misc_feature
<223> OTHER INFORMATION: LC variable region of clone/well 825 - rabbit

<400> SEQUENCE: 6

Gly Tyr Asp Met Thr Gln Thr Pro Ala Ser Val Ser Ala Ala Val Gly
1               5                   10                  15

Gly Thr Val Thr Ile Asn Cys Gln Ala Ser Glu Asn Ile Tyr Ser Thr
                20                  25                  30

Leu Ala Trp Tyr Gln Lys Pro Gly Gln Pro Pro Lys Val Leu Ile
            35                  40                  45

Tyr Asp Ala Phe Asp Leu Ala Ser Gly Val Pro Ser Arg Phe Lys Gly

```
                    50                  55                  60
Ser Gly Ser Gly Thr Glu Tyr Thr Leu Thr Ile Ser Gly Val Gln Ser
 65                  70                  75                  80

Asp Asp Ala Ala Thr Tyr Tyr Cys Gln Gln Gly Tyr Ser Gly Thr Asn
                 85                  90                  95

Val Asp Asn Ala Phe Gly Gly Gly Thr Glu Val Val Val Lys
                100                 105                 110
```

<210> SEQ ID NO 7
<211> LENGTH: 121
<212> TYPE: PRT
<213> ORGANISM: Oryctolagus cuniculus
<220> FEATURE:
<221> NAME/KEY: misc_feature
<223> OTHER INFORMATION: HC variable region of clone/well 828 - rabbit

<400> SEQUENCE: 7

```
Gln Ser Val Glu Glu Ser Gly Gly Arg Leu Val Thr Pro Gly Thr Pro
 1               5                  10                  15

Leu Thr Leu Thr Cys Thr Val Ser Glu Ile Asp Leu Ser Thr Tyr Ala
                20                  25                  30

Met Ser Trp Val Arg Gln Ala Pro Gly Lys Gly Leu Glu Trp Ile Gly
            35                  40                  45

Ile Ile Ser Ala Gly Gly Ser Ala Tyr Tyr Ala Ser Trp Ala Lys Gly
 50                  55                  60

Arg Phe Thr Ile Ser Arg Thr Ser Thr Thr Val Asp Leu Lys Met Thr
 65                  70                  75                  80

Ser Leu Thr Thr Glu Asp Thr Ala Thr Tyr Phe Cys Ala Arg Gly Ala
                85                  90                  95

Ala Tyr Ala Gly Tyr Thr Tyr Gly Phe Ser Phe Asp Ile Trp Gly
                100                 105                 110

Pro Gly Thr Leu Val Thr Val Ser Leu
            115                 120
```

<210> SEQ ID NO 8
<211> LENGTH: 110
<212> TYPE: PRT
<213> ORGANISM: Oryctolagus cuniculus
<220> FEATURE:
<221> NAME/KEY: misc_feature
<223> OTHER INFORMATION: LC variable region of clone/well 828 - rabbit

<400> SEQUENCE: 8

```
Asp Ile Val Met Thr Gln Thr Pro Ser Ser Val Ser Ala Ala Val Gly
 1               5                  10                  15

Gly Thr Val Thr Ile Asn Cys Gln Ala Ser Gln Asn Ile Tyr Ser Asn
                20                  25                  30

Leu Ala Trp Tyr Gln Gln Lys Pro Gly Gln Arg Pro Lys Leu Leu Ile
            35                  40                  45

Tyr Gly Ala Ser Asn Leu Glu Ser Gly Val Pro Ser Arg Phe Lys Gly
 50                  55                  60

Ser Gly Ser Gly Thr Glu Tyr Thr Leu Thr Ile Ser Asp Leu Glu Ser
 65                  70                  75                  80

Asp Asp Ala Ala Thr Tyr Tyr Cys Gln Ser Ile Asp Tyr Gly Asn Asn
                85                  90                  95

Tyr Leu Gly Ser Phe Gly Gly Gly Thr Glu Val Val Val Lys
                100                 105                 110
```

-continued

```
<210> SEQ ID NO 9
<211> LENGTH: 117
<212> TYPE: PRT
<213> ORGANISM: Oryctolagus cuniculus
<220> FEATURE:
<221> NAME/KEY: misc_feature
<223> OTHER INFORMATION: HC variable region of clone/well 829 - rabbit

<400> SEQUENCE: 9

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Asp
            20                  25                  30

Met Ser Trp Val Arg Gln Ala Pro Gly Lys Gly Leu Glu Tyr Ile Gly
        35                  40                  45

Trp Ile Asn Ser Asp Asp Gly Ala Tyr Tyr Ala Asn Trp Ala Lys Gly
    50                  55                  60

Arg Phe Thr Ile Ser Arg Thr Ser Thr Thr Val Asp Leu Lys Ile Thr
65                  70                  75                  80

Ser Pro Thr Thr Glu Asp Thr Ala Thr Tyr Phe Cys Ala Arg Asp Ala
                85                  90                  95

Gly Ser Thr Tyr Leu Tyr Gly Leu Asp Pro Trp Gly Pro Gly Thr Leu
            100                 105                 110

Val Thr Val Ser Ser
        115

<210> SEQ ID NO 10
<211> LENGTH: 109
<212> TYPE: PRT
<213> ORGANISM: Oryctolagus cuniculus
<220> FEATURE:
<221> NAME/KEY: misc_feature
<223> OTHER INFORMATION: LC variable region of clone/well 829 - rabbit

<400> SEQUENCE: 10

Asp Val Val Met Thr Gln Thr Pro Ser Ser Val Ser Ala Gly Val Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly Gln Arg Pro Lys Leu Leu Ile
        35                  40                  45

Tyr Ala Ala Ser Thr Leu Ala Ser Gly Val Ser Ser Arg Phe Lys Gly
    50                  55                  60

Ser Gly Ser Gly Thr Glu Tyr Thr Leu Thr Ile Asn Asp Leu Glu Ser
65                  70                  75                  80

Ala Asp Ala Ala Thr Tyr Tyr Cys Gln Cys Thr Tyr Tyr Gly Gly Thr
                85                  90                  95

Tyr Asn Thr Phe Gly Gly Gly Thr Glu Val Val Val Lys
            100                 105

<210> SEQ ID NO 11
<211> LENGTH: 119
<212> TYPE: PRT
<213> ORGANISM: Oryctolagus cuniculus
<220> FEATURE:
<221> NAME/KEY: misc_feature
<223> OTHER INFORMATION: HC variable region of clone/well 833 - rabbit

<400> SEQUENCE: 11

Gln Ser Leu Glu Glu Ser Gly Gly Gly Leu Val Thr Pro Gly Gly Ser
1               5                   10                  15
```

```
Leu Thr Leu Thr Cys Thr Gly Ser Gly Ile Asp Leu Ser His Tyr Val
            20                  25                  30

Val Gly Trp Val Arg Gln Ala Pro Gly Lys Gly Leu Glu Trp Ile Gly
        35                  40                  45

Ile Ile Tyr Gly Ser Gly Arg Thr Tyr Tyr Ala Asn Trp Ala Lys Gly
    50                  55                  60

Arg Phe Thr Ile Ser Lys Thr Ser Thr Thr Val Asp Leu Arg Ile Ala
65                  70                  75                  80

Arg Pro Thr Ala Glu Asp Thr Ala Thr Tyr Phe Cys Ala Arg Asp Ala
                85                  90                  95

Ser Val Ser Val Tyr Tyr Trp Gly Tyr Phe Asp Leu Trp Gly Gln Gly
            100                 105                 110

Thr Leu Val Thr Val Ser Ser
        115

<210> SEQ ID NO 12
<211> LENGTH: 110
<212> TYPE: PRT
<213> ORGANISM: Oryctolagus cuniculus
<220> FEATURE:
<221> NAME/KEY: misc_feature
<223> OTHER INFORMATION: LC variable region of clone/well 833 - rabbit

<400> SEQUENCE: 12

Ala Tyr Asp Met Thr Gln Thr Pro Val Ser Val Glu Val Ala Val Gly
1               5                   10                  15

Gly Thr Val Thr Ile Lys Cys Gln Ala Ser Gln Ser Ile Gly Ser Glu
            20                  25                  30

Leu Ala Trp Tyr Gln Gln Lys Pro Gly Gln Pro Pro Lys Leu Leu Ile
        35                  40                  45

Tyr Arg Ala Ser Thr Leu Glu Ser Gly Val Pro Ser Arg Phe Ser Gly
    50                  55                  60

Ser Gly Ser Gly Thr Glu Phe Thr Leu Thr Ile Ser Gly Val Glu Ser
65                  70                  75                  80

Ala Asp Ala Ala Thr Tyr Tyr Cys Gln Gln Gly Tyr Thr Tyr Ser Glu
                85                  90                  95

Ile Asp Asn Ala Phe Gly Gly Gly Thr Glu Val Val Val Lys
            100                 105                 110

<210> SEQ ID NO 13
<211> LENGTH: 120
<212> TYPE: PRT
<213> ORGANISM: Oryctolagus cuniculus
<220> FEATURE:
<221> NAME/KEY: misc_feature
<223> OTHER INFORMATION: HC variable region of clone/well 834 - rabbit

<400> SEQUENCE: 13

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Thr Tyr Ser
            20                  25                  30

Met Ser Trp Val Arg Gln Ala Pro Gly Lys Gly Leu Glu Trp Ile Gly
        35                  40                  45

Val Ile Ser Arg Gly Gly Ser Ala Tyr Tyr Ala Ser Trp Ala Lys Gly
    50                  55                  60

Arg Phe Thr Ile Ser Lys Thr Ser Thr Thr Val Asp Leu Lys Val Thr
65                  70                  75                  80
```

-continued

Ser Pro Thr Thr Glu Asp Thr Ala Thr Tyr Phe Cys Ala Arg Gly Ala
                85                  90                  95

Ile Ser Ser Gly Tyr Tyr Val Tyr Asp Gly Met Asp Leu Trp Gly Pro
            100                 105                 110

Gly Thr Leu Val Thr Val Ser Ser
        115                 120

<210> SEQ ID NO 14
<211> LENGTH: 110
<212> TYPE: PRT
<213> ORGANISM: Oryctolagus cuniculus
<220> FEATURE:
<221> NAME/KEY: misc_feature
<223> OTHER INFORMATION: LC variable region of clone/well 834 - rabbit

<400> SEQUENCE: 14

Asp Ile Val Met Thr Gln Thr Pro Gly Ser Val Glu Ala Ala Val Gly
1               5                   10                  15

Gly Thr Val Thr Ile Lys Cys Gln Ala Ser Glu Ser Ile Ser Ser Tyr
            20                  25                  30

Leu Ala Trp Tyr Gln Gln Lys Pro Gly Gln Pro Pro Lys Phe Leu Ile
        35                  40                  45

Tyr Ser Ala Ser Thr Leu Ala Ser Gly Val Pro Ser Arg Phe Lys Gly
    50                  55                  60

Ser Gly Ser Gly Thr Glu Phe Thr Leu Thr Ile Ser Asp Leu Glu Ser
65                  70                  75                  80

Ala Asp Ala Ala Thr Tyr Tyr Cys Gln Cys Thr Asp Tyr Gly Ser Asp
                85                  90                  95

Tyr Met Gly Ala Phe Gly Gly Gly Thr Gly Val Val Val Lys
            100                 105                 110

<210> SEQ ID NO 15
<211> LENGTH: 117
<212> TYPE: PRT
<213> ORGANISM: Oryctolagus cuniculus
<220> FEATURE:
<221> NAME/KEY: misc_feature
<223> OTHER INFORMATION: HC variable region of clone/well 835 - rabbit

<400> SEQUENCE: 15

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Gly Ala
            20                  25                  30

Met Gly Trp Val Arg Gln Ala Pro Gly Lys Gly Leu Glu Trp Ile Gly
        35                  40                  45

Leu Ile Ser Ser Ser Pro Ile Thr Tyr Tyr Ala Asn Trp Ala Arg Gly
    50                  55                  60

Arg Phe Thr Ile Ser Lys Thr Ser Thr Thr Val Asp Leu Lys Ile Thr
65                  70                  75                  80

Ser Pro Thr Thr Ala Asp Thr Ala Thr Tyr Phe Cys Ala Arg Gly Tyr
                85                  90                  95

Asp Asp Tyr Gly Glu Ile Trp Phe Asn Ile Trp Gly Pro Gly Thr Leu
            100                 105                 110

Val Thr Val Ser Leu
        115

<210> SEQ ID NO 16

<211> LENGTH: 109
<212> TYPE: PRT
<213> ORGANISM: Oryctolagus cuniculus
<220> FEATURE:
<221> NAME/KEY: misc_feature
<223> OTHER INFORMATION: LC variable region of clone/well 835 - rabbit

<400> SEQUENCE: 16

```
Ala Ile Glu Met Thr Gln Ser Pro Ser Leu Ser Ala Ser Val Gly
1               5                   10                  15

Glu Thr Val Arg Ile Arg Cys Leu Ala Gly Asp Ile Tyr Ser Ser
            20                  25                  30

Ile Ser Trp Tyr Gln Gln Lys Pro Gly Lys Pro Thr Leu Leu Ile
        35                  40                  45

Tyr Gly Ala Ser Asn Leu Glu Ser Gly Val Pro Pro Arg Phe Ser Gly
50                  55                  60

Ser Gly Ser Gly Thr Asp Tyr Thr Leu Thr Ile Gly Gly Val Gln Ala
65                  70                  75                  80

Glu Asp Ala Ala Thr Tyr Tyr Cys Leu Gly Gly Trp Ser Tyr Ser Ser
                85                  90                  95

Ser Leu Thr Phe Gly Ala Gly Thr Lys Val Glu Ile Lys
            100                 105
```

<210> SEQ ID NO 17
<211> LENGTH: 120
<212> TYPE: PRT
<213> ORGANISM: Oryctolagus cuniculus
<220> FEATURE:
<221> NAME/KEY: misc_feature
<223> OTHER INFORMATION: HC variable region of clone/well 841 - rabbit

<400> SEQUENCE: 17

```
Gln Ser Leu Glu Glu Ser Gly Gly Arg Leu Val Thr Pro Gly Thr Pro
1               5                   10                  15

Leu Thr Leu Thr Cys Lys Ala Ser Gly Phe Ser Leu Ser Thr Tyr Trp
            20                  25                  30

Met Ser Trp Val Arg Gln Ala Pro Gly Lys Gly Leu Glu Trp Ile Gly
        35                  40                  45

Ile Met Leu Ser Tyr Gly Asn Thr Val Tyr Ala Asn Trp Ala Lys Gly
50                  55                  60

Arg Phe Thr Ile Ser Lys Thr Ser Thr Thr Val Asp Leu Lys Ile
65                  70                  75                  80

Thr Ser Pro Thr Thr Glu Asp Thr Ala Thr Tyr Phe Cys Ala Arg Gly
                85                  90                  95

Leu Tyr Gly Gly Tyr Pro Asn Tyr Gly Val Tyr Asp Leu Trp Gly Gln
            100                 105                 110

Gly Thr Leu Val Thr Val Ser Ser
        115                 120
```

<210> SEQ ID NO 18
<211> LENGTH: 110
<212> TYPE: PRT
<213> ORGANISM: Oryctolagus cuniculus
<220> FEATURE:
<221> NAME/KEY: misc_feature
<223> OTHER INFORMATION: LC variable region of clone/well 841 - rabbit

<400> SEQUENCE: 18

```
Asp Val Val Met Thr Gln Thr Pro Ala Ser Val Glu Ala Ala Val Gly
1               5                   10                  15
```

```
Gly Thr Val Thr Ile Lys Cys Gln Ala Ser Gln Ser Ile Ser Ser Tyr
            20                  25                  30

Leu Ser Trp Tyr Gln Gln Lys Pro Gly Gln Pro Pro Lys Leu Leu Ile
        35                  40                  45

Tyr Ala Ala Ser Asn Leu Ala Ser Gly Val Ser Ser Arg Phe Lys Gly
    50                  55                  60

Ser Arg Ser Gly Thr Glu Tyr Thr Leu Thr Ile Ser Asp Leu Glu Ser
65                  70                  75                  80

Ala Asp Ala Ala Thr Tyr Tyr Cys Gln Cys Thr Asp Tyr Gly Ser Asn
                85                  90                  95

Tyr Val Gly Ala Phe Gly Gly Gly Thr Glu Val Val Val Lys
            100                 105                 110

<210> SEQ ID NO 19
<211> LENGTH: 121
<212> TYPE: PRT
<213> ORGANISM: Oryctolagus cuniculus
<220> FEATURE:
<221> NAME/KEY: misc_feature
<223> OTHER INFORMATION: HC variable region of clone/well 843 - rabbit

<400> SEQUENCE: 19

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Asn Asn Ala Tyr
            20                  25                  30

Met Asn Trp Val Arg Gln Ala Pro Gly Lys Gly Leu Glu Trp Ile Gly
        35                  40                  45

Ile Ile Asn Thr Tyr Gly Ser Thr Tyr Phe Ala Thr Trp Ala Lys Gly
    50                  55                  60

Arg Phe Thr Phe Ser Lys Thr Ser Thr Val Asp Leu Lys Ile Thr
65                  70                  75                  80

Ser Pro Thr Thr Glu Asp Thr Ala Thr Tyr Phe Cys Ala Arg Ala Tyr
                85                  90                  95

Ala Pro Phe Ser Thr Tyr Ser His Tyr Tyr Gly Met Asp Leu Trp Gly
            100                 105                 110

Pro Gly Thr Leu Val Thr Val Ser Ser
        115                 120

<210> SEQ ID NO 20
<211> LENGTH: 110
<212> TYPE: PRT
<213> ORGANISM: Oryctolagus cuniculus
<220> FEATURE:
<221> NAME/KEY: misc_feature
<223> OTHER INFORMATION: LC variable region of clone/well 843 - rabbit

<400> SEQUENCE: 20

Asp Val Val Met Thr Gln Thr Pro Ser Val Ser Ala Ala Val Gly
1               5                   10                  15

Gly Thr Val Thr Ile Lys Cys Gln Ala Ser Glu Ser Ile Gly Ser Trp
            20                  25                  30

Leu Ser Trp Tyr Gln Gln Lys Pro Gly Gln Pro Pro Lys Leu Leu Ile
        35                  40                  45

Tyr Glu Ala Ser Lys Leu Thr Ser Gly Val Pro Ser Arg Phe Lys Gly
    50                  55                  60

Ser Gly Ser Gly Thr Glu Tyr Thr Leu Thr Ile Ser Asp Leu Glu Ser
65                  70                  75                  80
```

Ala Asp Ala Ala Thr Tyr Tyr Cys Gln Tyr Thr Asp Tyr Gly Ser Asn
            85                  90                  95

Tyr Leu Gly Thr Phe Gly Gly Gly Thr Glu Val Val Val Lys
            100                 105                 110

<210> SEQ ID NO 21
<211> LENGTH: 119
<212> TYPE: PRT
<213> ORGANISM: Oryctolagus cuniculus
<220> FEATURE:
<221> NAME/KEY: misc_feature
<223> OTHER INFORMATION: HC variable region of clone/well 845 - rabbit

<400> SEQUENCE: 21

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Thr
            20                  25                  30

Met Asn Trp Val Arg Gln Ala Pro Gly Lys Gly Leu Glu Trp Ile Gly
        35                  40                  45

Val Ile Thr Ser His Asn Thr Tyr Tyr Ala Ser Trp Ala Lys Gly Arg
    50                  55                  60

Phe Thr Ile Ser Lys Thr Ser Thr Thr Val Asp Leu Lys Ile Thr Ser
65                  70                  75                  80

Pro Thr Thr Glu Asp Thr Ala Thr Tyr Phe Cys Ala Arg Ser Asn Tyr
                85                  90                  95

Gly Ser Thr Ile Tyr Tyr Met Gly Gly Met Asp Pro Trp Gly Pro Gly
            100                 105                 110

Thr Leu Val Thr Val Ser Ser
        115

<210> SEQ ID NO 22
<211> LENGTH: 110
<212> TYPE: PRT
<213> ORGANISM: Oryctolagus cuniculus
<220> FEATURE:
<221> NAME/KEY: misc_feature
<223> OTHER INFORMATION: LC variable region of clone/well 845 - rabbit

<400> SEQUENCE: 22

Asp Val Val Met Thr Gln Thr Pro Ala Ser Val Ser Ala Ala Val Gly
1               5                   10                  15

Gly Thr Val Thr Ile Asn Cys Gln Ala Ser Gln Ser Ile Gly Ser Tyr
            20                  25                  30

Leu Ala Trp Tyr Gln His Gln Pro Gly Gln Pro Lys Leu Leu Ile
        35                  40                  45

Tyr Ser Ala Ser Thr Leu Glu Ser Gly Val Ser Ser Arg Phe Glu Gly
    50                  55                  60

Ser Arg Ser Gly Thr Glu Tyr Thr Leu Thr Ile Ser Asp Leu Asp Ser
65                  70                  75                  80

Ala Asp Ala Ala Thr Tyr Tyr Cys Gln Cys Thr Asp Tyr Gly Ala Ser
                85                  90                  95

Tyr Leu Gly Ala Phe Gly Gly Gly Thr Glu Val Val Val Lys
            100                 105                 110

<210> SEQ ID NO 23
<211> LENGTH: 118
<212> TYPE: PRT
<213> ORGANISM: Oryctolagus cuniculus
<220> FEATURE:

<221> NAME/KEY: misc_feature
<223> OTHER INFORMATION: HC variable region of clone/well 847 - rabbit

<400> SEQUENCE: 23

```
Gln Ser Val Glu Glu Ser Gly Gly Arg Leu Val Thr Pro Gly Thr Pro
1               5                   10                  15
Leu Thr Leu Thr Cys Thr Val Ser Gly Phe Ser Leu Ser Ser Tyr Asp
            20                  25                  30
Met Ser Trp Val Arg Gln Ala Pro Gly Lys Gly Leu Glu Tyr Ile Gly
        35                  40                  45
Tyr Ile Asn Ser Asp Gly Ser Ala Tyr Tyr Ala Ser Trp Ala Lys Gly
    50                  55                  60
Arg Phe Thr Ile Ser Lys Thr Ser Ser Thr Thr Val Asp Leu Lys Ile
65                  70                  75                  80
Thr Ser Pro Thr Thr Glu Asp Thr Ala Thr Tyr Phe Cys Ala Arg Asp
                85                  90                  95
Ala Gly Ser Thr Tyr Leu Tyr Gly Met Asp Pro Trp Gly Pro Gly Thr
            100                 105                 110
Leu Val Thr Val Ser Ser
        115
```

<210> SEQ ID NO 24
<211> LENGTH: 109
<212> TYPE: PRT
<213> ORGANISM: Oryctolagus cuniculus
<220> FEATURE:
<221> NAME/KEY: misc_feature
<223> OTHER INFORMATION: LC variable region of clone/well 847 - rabbit

<400> SEQUENCE: 24

```
Asp Val Val Met Thr Gln Thr Pro Ala Ser Val Ser Glu Pro Val Gly
1               5                   10                  15
Gly Thr Val Thr Ile Asn Cys Gln Ala Ser Gln Ser Ile Tyr Ser Tyr
            20                  25                  30
Leu Ala Trp Tyr Gln Gln Lys Pro Gly Gln Arg Pro Lys Leu Leu Ile
        35                  40                  45
Tyr Ala Ala Ser Thr Leu Ala Ser Gly Val Ser Ser Arg Phe Lys Gly
    50                  55                  60
Ser Gly Ser Gly Thr Gln Phe Thr Leu Thr Ile Ser Asp Leu Glu Ser
65                  70                  75                  80
Ala Asp Ala Ala Thr Tyr Tyr Cys Gln Cys Thr Tyr Tyr Gly Gly Thr
                85                  90                  95
Phe Asn Thr Phe Gly Gly Gly Thr Glu Val Val Val Lys
            100                 105
```

<210> SEQ ID NO 25
<211> LENGTH: 120
<212> TYPE: PRT
<213> ORGANISM: Oryctolagus cuniculus
<220> FEATURE:
<221> NAME/KEY: misc_feature
<223> OTHER INFORMATION: HC variable region of clone/well 848 - rabbit

<400> SEQUENCE: 25

```
Gln Ser Val Glu Glu Ser Gly Gly Arg Leu Val Thr Pro Gly Thr Pro
1               5                   10                  15
Leu Thr Leu Thr Cys Thr Val Ser Gly Phe Ser Leu Ser Ser Tyr Thr
            20                  25                  30
Met Ser Trp Val Arg Gln Ala Pro Gly Lys Gly Leu Glu Trp Ile Gly
```

```
            35                  40                  45
Ile Ile Ser Ser Ile Gly Ser Ile Trp Tyr Ala Ser Trp Ala Lys Gly
 50                  55                  60

Arg Phe Thr Ile Ser Lys Thr Ser Thr Val Asp Leu Lys Met Thr
 65                  70                  75                  80

Ser Leu Thr Thr Glu Asp Thr Ala Thr Tyr Phe Cys Ala Arg Asp Gly
                 85                  90                  95

Thr Gly Ser Lys Tyr Tyr Thr Trp Asp Arg Leu Asp Leu Trp Gly Gln
            100                 105                 110

Gly Thr Leu Val Thr Val Ser Ser
            115                 120

<210> SEQ ID NO 26
<211> LENGTH: 110
<212> TYPE: PRT
<213> ORGANISM: Oryctolagus cuniculus
<220> FEATURE:
<221> NAME/KEY: misc_feature
<223> OTHER INFORMATION: LC variable region of clone/well 848 - rabbit

<400> SEQUENCE: 26

Asn Ile Val Met Thr Gln Thr Pro Ser Pro Val Ser Gly Ala Val Gly
 1               5                  10                  15

Gly Thr Val Thr Ile Asn Cys Gln Ala Ser Gln Ser Ile Tyr Asn Glu
                20                  25                  30

Leu Ser Trp Tyr Gln Gln Lys Pro Gly Gln Pro Pro Lys Leu Leu Ile
             35                  40                  45

Tyr Tyr Thr Ser Thr Leu Ala Ser Gly Val Ser Ser Arg Phe Lys Gly
 50                  55                  60

Ser Gly Ser Gly Thr Gln Phe Thr Leu Thr Ile Ser Gly Val Glu Ser
 65                  70                  75                  80

Val Asp Ala Ala Thr Tyr Tyr Cys Gln Gln Gly Tyr Ser Ser Ser Asp
                 85                  90                  95

Val Asp Asn Val Phe Gly Gly Gly Thr Glu Val Val Val Lys
            100                 105                 110

<210> SEQ ID NO 27
<211> LENGTH: 117
<212> TYPE: PRT
<213> ORGANISM: Oryctolagus cuniculus
<220> FEATURE:
<221> NAME/KEY: misc_feature
<223> OTHER INFORMATION: HC variable region of clone/well 849 - rabbit

<400> SEQUENCE: 27

Gln Ser Val Glu Glu Ser Gly Gly Arg Leu Val Thr Pro Gly Thr Pro
 1               5                  10                  15

Leu Thr Leu Thr Cys Thr Val Ser Gly Phe Ser Leu Ser Arg Tyr Asp
                20                  25                  30

Met Ser Trp Val Arg Gln Ala Pro Gly Lys Gly Leu Glu Tyr Ile Gly
             35                  40                  45

Tyr Ile Asn Arg Asp Gly Ser Ala Tyr Tyr Ala Asn Trp Ala Lys Gly
 50                  55                  60

Arg Phe Thr Ile Ser Lys Thr Ser Thr Thr Val Asp Leu Lys Ile Thr
 65                  70                  75                  80

Ser Pro Thr Thr Asp Asp Thr Ala Thr Tyr Phe Cys Ala Arg His Ala
                 85                  90                  95

Gly Ser Thr Tyr Leu Tyr Gly Met Asp Pro Trp Gly Pro Gly Thr Leu
```

Val Thr Val Ser Ser
        115

<210> SEQ ID NO 28
<211> LENGTH: 109
<212> TYPE: PRT
<213> ORGANISM: Oryctolagus cuniculus
<220> FEATURE:
<221> NAME/KEY: misc_feature
<223> OTHER INFORMATION: LC variable region of clone/well 849 - rabbit

<400> SEQUENCE: 28

Asp Val Val Met Thr Gln Thr Pro Ser Ser Val Ser Ala Ala Val Gly
1               5                   10                  15

Gly Thr Val Thr Ile Lys Cys Gln Ala Ser Gln Ser Ile Ser Asn Tyr
            20                  25                  30

Leu Ala Trp Tyr Gln Gln Lys Pro Gly Gln Pro Pro Lys Leu Leu Ile
        35                  40                  45

Tyr Ala Ala Ser Thr Leu Ala Ser Gly Val Ser Ser Arg Phe Lys Gly
    50                  55                  60

Ser Gly Ser Gly Thr Glu Phe Thr Leu Thr Ile Ser Asp Leu Glu Ser
65                  70                  75                  80

Ala Asp Ala Ala Thr Tyr Tyr Cys Gln Cys Thr Tyr Phe Gly Asp Thr
                85                  90                  95

Tyr Asn Val Phe Gly Gly Gly Thr Glu Val Val Val Lys
            100                 105

<210> SEQ ID NO 29
<211> LENGTH: 118
<212> TYPE: PRT
<213> ORGANISM: Oryctolagus cuniculus
<220> FEATURE:
<221> NAME/KEY: misc_feature
<223> OTHER INFORMATION: HC variable region of clone/well 868 - rabbit

<400> SEQUENCE: 29

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Asp Tyr Thr
            20                  25                  30

Met Gly Trp Val Arg Gln Ala Pro Gly Lys Gly Leu Glu Trp Ile Gly
        35                  40                  45

Ile Ile Asn Gly Tyr Gly Ser Thr Tyr Tyr Ala Asn Trp Ala Lys Gly
    50                  55                  60

Arg Phe Ala Ile Ser Lys Thr Ser Thr Thr Val Asp Leu Lys Ile Thr
65                  70                  75                  80

Ser Pro Ala Thr Glu Asp Thr Ala Thr Tyr Phe Cys Ala Arg Gly Asp
                85                  90                  95

Thr Gly Arg Thr Tyr Asp Met His Phe Asn Leu Trp Gly Gln Gly Thr
            100                 105                 110

Leu Val Thr Val Ser Ser
        115

<210> SEQ ID NO 30
<211> LENGTH: 110
<212> TYPE: PRT
<213> ORGANISM: Oryctolagus cuniculus
<220> FEATURE:
<221> NAME/KEY: misc_feature
<223> OTHER INFORMATION: LC variable region of clone/well 868 - rabbit

<400> SEQUENCE: 30

Ala Tyr Asp Met Thr Gln Thr Pro Ala Ser Val Ser Ala Val Gly
1               5                   10                  15

Gly Thr Val Thr Ile Lys Cys Gln Ala Ser Glu Ser Ile Arg Ser Trp
            20                  25                  30

Leu Ala Trp Tyr Gln Gln Lys Pro Gly Gln Pro Pro Lys Leu Leu Ile
        35                  40                  45

Tyr Ser Ala Ser Thr Leu Ala Ser Gly Val Ser Ser Arg Phe Lys Gly
    50                  55                  60

Ser Gly Ser Gly Thr Gln Phe Thr Leu Thr Ile Gly Asp Leu Glu Ser
65                  70                  75                  80

Ala Asp Ala Ala Thr Tyr Tyr Cys Gln Gln Gly Tyr Thr Ser Ser Asn
                85                  90                  95

Leu Asp Asn Ala Phe Gly Gly Gly Thr Glu Val Leu Val Lys
            100                 105                 110

<210> SEQ ID NO 31
<211> LENGTH: 120
<212> TYPE: PRT
<213> ORGANISM: Oryctolagus cuniculus
<220> FEATURE:
<221> NAME/KEY: misc_feature
<223> OTHER INFORMATION: HC variable region of clone/well 899 - rabbit

<400> SEQUENCE: 31

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Thr
            20                  25                  30

Met Ser Trp Val Arg Gln Ala Pro Gly Lys Gly Leu Glu Tyr Ile Gly
        35                  40                  45

Ile Ile Ser Ser Ser Asp Gly Thr Trp Tyr Ala Asn Trp Val Lys Gly
    50                  55                  60

Arg Phe Thr Ile Ser Lys Thr Ser Thr Thr Val Asp Leu Lys Met Thr
65                  70                  75                  80

Ser Leu Thr Thr Glu Asp Thr Ala Thr Tyr Phe Cys Ala Arg Asp Gly
                85                  90                  95

Thr Gly Asn Lys Tyr Tyr Thr Trp Asp Arg Leu Asp Leu Trp Gly Gln
            100                 105                 110

Gly Thr Leu Val Thr Val Ser Ser
        115                 120

<210> SEQ ID NO 32
<211> LENGTH: 110
<212> TYPE: PRT
<213> ORGANISM: Oryctolagus cuniculus
<220> FEATURE:
<221> NAME/KEY: misc_feature
<223> OTHER INFORMATION: LC variable region of clone/well 899 - rabbit

<400> SEQUENCE: 32

Asn Ile Val Met Thr Gln Thr Pro Ser Pro Val Ser Gly Ala Val Gly
1               5                   10                  15

Gly Thr Val Thr Ile Asn Cys Gln Ala Ser Gln Ser Ile Tyr Asn Glu
            20                  25                  30

Leu Ser Trp Tyr Gln Gln Lys Pro Gly Gln Pro Pro Lys Leu Leu Ile
        35                  40                  45

-continued

Tyr Tyr Ala Ser Thr Leu Ala Ser Gly Val Ser Ser Arg Phe Lys Gly
            50                  55                  60

Ser Gly Ser Gly Thr Gln Phe Thr Leu Thr Ile Ser Gly Val Glu Ser
65                  70                  75                  80

Val Asp Ala Ala Thr Tyr Tyr Cys Gln Gln Gly Tyr Ser Ser Ser Asn
                85                  90                  95

Val Asp Asn Val Phe Gly Gly Gly Thr Glu Val Val Val Lys
            100                 105                 110

<210> SEQ ID NO 33
<211> LENGTH: 118
<212> TYPE: PRT
<213> ORGANISM: Oryctolagus cuniculus
<220> FEATURE:
<221> NAME/KEY: misc_feature
<223> OTHER INFORMATION: HC variable region of clone/well 908 - rabbit

<400> SEQUENCE: 33

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Phe Ala
            20                  25                  30

Met Ser Trp Val Arg Gln Ala Pro Gly Lys Gly Leu Glu Trp Ile Gly
        35                  40                  45

Ile Ile Asn Gly Tyr Gly Ser Ile Tyr Tyr Ala Thr Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Gly Asp
                85                  90                  95

Ala Gly Arg Thr Tyr Asn His Tyr Phe Asn Ile Trp Gly Pro Gly Thr
            100                 105                 110

Leu Val Thr Val Ser Leu
        115

<210> SEQ ID NO 34
<211> LENGTH: 110
<212> TYPE: PRT
<213> ORGANISM: Oryctolagus cuniculus
<220> FEATURE:
<221> NAME/KEY: misc_feature
<223> OTHER INFORMATION: LC variable region of clone/well 908 - rabbit

<400> SEQUENCE: 34

Asp Val Val Met Thr Gln Thr Pro Ala Ser Val Glu Ala Ala Val Gly
1               5                   10                  15

Gly Thr Val Thr Ile Lys Cys Gln Ala Ser Gln Ser Ile Ser Ser Trp
            20                  25                  30

Leu Ser Trp Tyr Gln Gln Lys Pro Gly Gln Arg Pro Lys Leu Leu Ile
        35                  40                  45

Tyr Ala Ala Ser Asn Leu Ala Ser Gly Val Pro Ser Arg Phe Lys Gly
    50                  55                  60

Ser Gly Ser Gly Thr Gln Phe Thr Leu Thr Ile Ser Asp Leu Glu Ser
65                  70                  75                  80

Asp Asp Ala Ala Thr Tyr Tyr Cys Gln Gln Gly Tyr Thr Ser Tyr Asn
                85                  90                  95

Val Asp Asn Ala Phe Gly Gly Gly Thr Glu Val Val Val Lys
            100                 105                 110

<210> SEQ ID NO 35
<211> LENGTH: 118
<212> TYPE: PRT
<213> ORGANISM: Artificial Sequence
<220> FEATURE:
<223> OTHER INFORMATION: HC variable region 789 humanized version 1

<400> SEQUENCE: 35

```
Glu Val Lys Val Glu Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Trp Met Ser Trp Val Arg Gln Ala Pro Gly Lys Gly Leu Glu Trp Val
        35                  40                  45

Ser Ile Ile Ala Gly Arg Gly Ser Thr Tyr Tyr Ala Ser Trp Ala Lys
    50                  55                  60

Gly Arg Phe Thr Ile Ser Lys Asp Asn Ser Glu Gly Met Val Tyr Leu
65                  70                  75                  80

Gln Met Asn Ser Leu Arg Ala Glu Asp Thr Ala Val Tyr Tyr Cys Ala
                85                  90                  95

Arg Val Ser Ser Ile Tyr Tyr Thr Phe Asn Leu Trp Gly Gln Gly Thr
            100                 105                 110

Thr Val Thr Val Ser Ser
        115
```

<210> SEQ ID NO 36
<211> LENGTH: 118
<212> TYPE: PRT
<213> ORGANISM: Artificial Sequence
<220> FEATURE:
<223> OTHER INFORMATION: HC variable region 789 humanized version 2

<400> SEQUENCE: 36

```
Glu Val Gln Leu Leu Glu Ser Gly Gly Ser Leu Val Leu Pro Gly Gly
1               5                   10                  15

Ser Leu Arg Leu Ser Cys Ala Ala Ser Gly Phe Ser Leu Ser Ser Tyr
            20                  25                  30

Trp Met Ser Trp Val Arg Gln Ala Pro Gly Lys Gly Leu Glu Trp Val
        35                  40                  45

Ser Ile Ile Ala Gly Arg Gly Ser Thr Tyr Tyr Ala Ser Trp Ala Lys
    50                  55                  60

Gly Arg Phe Thr Ile Ser Arg Asp Asn Ser Lys Asn Thr Leu Tyr Met
65                  70                  75                  80

Gln Met Asn Ser Leu Arg Ala Glu Asp Thr Ala Leu Tyr Phe Cys Ala
                85                  90                  95

Arg Val Ser Ser Ile Tyr Tyr Thr Phe Asn Leu Trp Gly Gln Gly Thr
            100                 105                 110

Leu Val Thr Val Ser Ser
        115
```

<210> SEQ ID NO 37
<211> LENGTH: 117
<212> TYPE: PRT
<213> ORGANISM: Artificial Sequence
<220> FEATURE:
<223> OTHER INFORMATION: HC variable region 789 humanized version 3

<400> SEQUENCE: 37

```
Gln Ser Val Glu Glu Ser Gly Gly Leu Val Gln Pro Gly Gly Ser
1               5                   10                  15

Leu Arg Leu Ser Cys Ala Ala Ser Gly Phe Ser Leu Ser Tyr Trp
                20                  25                  30

Met Ser Trp Val Arg Gln Ala Pro Gly Lys Gly Leu Glu Trp Ile Gly
                35                  40                  45

Ile Ile Ala Gly Arg Gly Ser Thr Tyr Tyr Ala Ser Trp Ala Lys Gly
50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Val Ser Ser Ile Tyr Tyr Thr Phe Asn Leu Trp Gly Gln Gly Thr Leu
                100                 105                 110

Val Thr Val Ser Ser
                115

<210> SEQ ID NO 38
<211> LENGTH: 121
<212> TYPE: PRT
<213> ORGANISM: Artificial Sequence
<220> FEATURE:
<223> OTHER INFORMATION: HC variable region 825 humanized version 1

<400> SEQUENCE: 38

Glu Val Gln Leu Val Glu Ser Gly Gly Asp Leu Ala Gln Pro Gly Gly
1               5                   10                  15

Ser Leu Arg Leu Ser Cys Ala Val Ser Gly Ile Asp Leu Ser Ser Tyr
                20                  25                  30

Gly Met Gly Trp Val Arg Gln Ala Pro Gly Lys Gly Leu Glu Trp Val
                35                  40                  45

Ser Ile Ile Ser Arg Asn Ser Val Thr Tyr Tyr Ala Thr Trp Ala Lys
50                  55                  60

Gly Arg Phe Thr Ile Ser Arg Asp Asn Ser Lys Asn Thr Val Tyr Leu
65                  70                  75                  80

Gln Met Thr Ser Leu Arg Ala Glu Asp Thr Ala Leu Tyr Phe Cys Ala
                85                  90                  95

Arg Arg Ala Thr Tyr Ser Gly Ala Leu Gly Tyr Phe Asp Ile Trp Gly
                100                 105                 110

Gln Gly Thr Leu Val Thr Val Ser Ser
            115                 120

<210> SEQ ID NO 39
<211> LENGTH: 121
<212> TYPE: PRT
<213> ORGANISM: Artificial Sequence
<220> FEATURE:
<223> OTHER INFORMATION: HC variable region 825 humanized version 2

<400> SEQUENCE: 39

Glu Val Gln Leu Glu Glu Ser Gly Gly Gly Leu Val Lys Pro Gly Gly
1               5                   10                  15

Ser Leu Arg Leu Ser Cys Ala Ala Ser Gly Ile Asp Leu Ser Ser Tyr
                20                  25                  30

Gly Met Gly Trp Val Arg Gln Ala Pro Gly Lys Gly Leu Glu Trp Val
                35                  40                  45

Ser Ile Ile Ser Arg Asn Ser Val Thr Tyr Tyr Ala Thr Trp Ala Lys
50                  55                  60
```

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Ala Thr Tyr Ser Gly Ala Leu Gly Tyr Phe Asp Ile Trp Gly
            100                 105                 110

Arg Gly Thr Leu Val Thr Val Ser Ser
        115                 120

<210> SEQ ID NO 40
<211> LENGTH: 122
<212> TYPE: PRT
<213> ORGANISM: Artificial Sequence
<220> FEATURE:
<223> OTHER INFORMATION: HC variable region 833 humanized version 1

<400> SEQUENCE: 40

Glu Val Gln Leu Val Glu Ser Gly Gly Gly Leu Ile Gln Pro Gly Gly
1               5                   10                  15

Ser Leu Arg Leu Ser Cys Ala Ala Ser Gly Ile Asp Leu Ser His Tyr
            20                  25                  30

Val Val Gly Trp Val Arg Gln Ala Pro Gly Lys Gly Leu Glu Trp Val
        35                  40                  45

Ser Ile Ile Tyr Gly Ser Gly Arg Thr Tyr Tyr Ala Asn Trp Ala Lys
    50                  55                  60

Gly Arg Phe Thr Ile Ser Lys Asp Asn Ser Lys Asn Thr Leu Tyr Val
65                  70                  75                  80

Arg Met Asn Ser Leu Arg Ala Glu Asp Thr Ala Val Tyr Tyr Cys Ala
                85                  90                  95

Arg Asp Ala Ser Val Ser Val Tyr Tyr Trp Gly Tyr Phe Asp Leu Trp
            100                 105                 110

Gly Gln Gly Thr Leu Val Thr Val Ser Ser
        115                 120

<210> SEQ ID NO 41
<211> LENGTH: 122
<212> TYPE: PRT
<213> ORGANISM: Artificial Sequence
<220> FEATURE:
<223> OTHER INFORMATION: HC variable region 833 humanized version 2

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Leu Ser His Tyr
            20                  25                  30

Val Val Gly Trp Val Arg Gln Ala Pro Gly Lys Gly Leu Glu Trp Val
        35                  40                  45

Ser Ile Ile Tyr Gly Ser Gly Arg Thr Tyr Tyr Ala Asn Trp Ala Lys
    50                  55                  60

Gly Arg Phe Thr Ile Ser Arg Asp Asn Ser Lys Asn Thr Leu Phe Leu
65                  70                  75                  80

Arg Met Asn Ser Leu Arg Val Glu Asp Thr Ala Val Tyr Phe Cys Ala
                85                  90                  95

Arg Asp Ala Ser Val Ser Val Tyr Tyr Trp Gly Tyr Phe Asp Leu Trp
            100                 105                 110

Gly Gln Gly Thr Leu Val Thr Val Ser Ser

```
            115                 120

<210> SEQ ID NO 42
<211> LENGTH: 122
<212> TYPE: PRT
<213> ORGANISM: Artificial Sequence
<220> FEATURE:
<223> OTHER INFORMATION: HC variable region 833 humanized version 3

<400> SEQUENCE: 42

Glu Val Gln Leu Glu Glu Ser Gly Gly Gly Leu Val Lys Pro Gly Gly
1               5                   10                  15

Ser Leu Arg Leu Ser Cys Ala Ala Ser Gly Ile Asp Leu Ser His Tyr
            20                  25                  30

Val Val Gly Trp Val Arg Gln Ala Pro Gly Lys Gly Leu Glu Trp Val
        35                  40                  45

Ser Ile Ile Tyr Gly Ser Gly Arg Thr Tyr Tyr Ala Asn Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Ala Ser Val Ser Val Tyr Tyr Trp Gly Tyr Phe Asp Leu Trp
            100                 105                 110

Gly Arg Gly Thr Leu Val Thr Val Ser Ser
            115                 120

<210> SEQ ID NO 43
<211> LENGTH: 121
<212> TYPE: PRT
<213> ORGANISM: Artificial Sequence
<220> FEATURE:
<223> OTHER INFORMATION: HC variable region 833 humanized version 4

<400> SEQUENCE: 43

Gln Ser Leu Glu Glu Ser Gly Gly Gly Leu Val Gln Pro Gly Gly Ser
1               5                   10                  15

Leu Arg Leu Ser Cys Ala Ala Ser Gly Ile Asp Leu Ser His Tyr Val
            20                  25                  30

Val Gly Trp Val Arg Gln Ala Pro Gly Lys Gly Leu Glu Trp Ile Gly
        35                  40                  45

Ile Ile Tyr Gly Ser Gly Arg Thr Tyr Tyr Ala Asn Trp Ala Lys Gly
    50                  55                  60

Arg Phe Thr Ile Ser Arg His Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Asp Ala Ser Val Ser Val Tyr Tyr Trp Gly Tyr Phe Asp Leu Trp Gly
            100                 105                 110

Gln Gly Thr Leu Val Thr Val Ser Ser
            115                 120

<210> SEQ ID NO 44
<211> LENGTH: 113
<212> TYPE: PRT
<213> ORGANISM: Artificial Sequence
<220> FEATURE:
<223> OTHER INFORMATION: LC variable region 789 humanized version 1

<400> SEQUENCE: 44
```

```
Asp Ile Val Met Thr Gln Ser Pro Asp Ser Leu Ala Val Ser Leu Gly
1               5                   10                  15

Glu Arg Ala Thr Ile Asn Cys Gln Ser Ser Gln Ser Val Tyr Ser Asn
            20                  25                  30

Asn Glu Leu Ser Trp Tyr Gln Gln Lys Pro Gly Gln Pro Pro Lys Leu
        35                  40                  45

Leu Ile Tyr Tyr Ala Ser Thr Leu Ala Ser Gly Val Pro Asp Arg Phe
    50                  55                  60

Ser Gly Ser Gly Ser Gly Thr Asp Phe Thr Leu Thr Ile Ser Ser Leu
65                  70                  75                  80

Gln Ala Glu Asp Val Ala Val Tyr Tyr Cys Gly Gly Tyr Tyr Ser
                85                  90                  95

Gly Ser Gly Trp Tyr Tyr Ala Phe Gly Gly Gly Thr Lys Leu Glu Ile
            100                 105                 110

Lys
```

<210> SEQ ID NO 45
<211> LENGTH: 113
<212> TYPE: PRT
<213> ORGANISM: Artificial Sequence
<220> FEATURE:
<223> OTHER INFORMATION: LC variable region 789 humanized version 2

<400> SEQUENCE: 45

```
Glu Ile Val Leu Thr Gln Ser Pro Ser Ser Leu Ser Ala Ser Val Gly
1               5                   10                  15

Asp Arg Val Thr Ile Thr Cys Gln Ser Ser Gln Ser Val Tyr Ser Asn
            20                  25                  30

Asn Glu Leu Ser Trp Tyr Gln Gln Lys Pro Gly Lys Ala Pro Lys Leu
        35                  40                  45

Leu Ile Tyr Tyr Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gly Gly Tyr Tyr Ser
                85                  90                  95

Gly Ser Gly Trp Tyr Tyr Ala Phe Gly Gln Gly Thr Lys Leu Glu Ile
            100                 105                 110

Lys
```

<210> SEQ ID NO 46
<211> LENGTH: 113
<212> TYPE: PRT
<213> ORGANISM: Artificial Sequence
<220> FEATURE:
<223> OTHER INFORMATION: LC variable region 789 humanized version 3

<400> SEQUENCE: 46

```
Ala Gln Val Leu Thr Gln Ser Pro Ser Ser Leu Ser Ala Ser Val Gly
1               5                   10                  15

Asp Arg Val Thr Ile Thr Cys Gln Ser Ser Gln Ser Val Tyr Ser Asn
            20                  25                  30

Asn Glu Leu Ser Trp Tyr Gln Gln Lys Pro Gly Lys Ala Pro Lys Leu
        35                  40                  45

Leu Ile Tyr Tyr Ala Ser Thr Leu Ala Ser Gly Val Pro Ser Arg Phe
    50                  55                  60
```

-continued

```
Ser Gly Ser Gly Ser Gly Thr Asp Phe Thr Leu Thr Ile Ser Ser Leu
 65                  70                  75                  80

Gln Pro Glu Asp Phe Ala Thr Tyr Tyr Cys Gln Gly Ser Tyr Tyr Ser
                 85                  90                  95

Gly Ser Gly Trp Tyr Tyr Ala Phe Gly Gly Gly Thr Lys Val Glu Ile
            100                 105                 110

Lys

<210> SEQ ID NO 47
<211> LENGTH: 110
<212> TYPE: PRT
<213> ORGANISM: Artificial Sequence
<220> FEATURE:
<223> OTHER INFORMATION: LC variable region 825 humanized version 1

<400> SEQUENCE: 47

Glu Ile Val Met Thr Gln Ser Pro Ser Ser Leu Ser Ala Ser Val Gly
  1               5                  10                  15

Asp Arg Val Thr Ile Thr Cys Gln Ala Ser Glu Asn Ile Tyr Ser Thr
                 20                  25                  30

Leu Ala Trp Tyr Gln Gln Lys Pro Gly Lys Ala Pro Lys Leu Leu Ile
             35                  40                  45

Tyr Asp Ala Phe Asp Leu Ala Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Gly Tyr Ser Gly Thr Asn
                 85                  90                  95

Val Asp Asn Ala Phe Gly Gln Gly Thr Lys Leu Glu Ile Lys
            100                 105                 110

<210> SEQ ID NO 48
<211> LENGTH: 110
<212> TYPE: PRT
<213> ORGANISM: Artificial Sequence
<220> FEATURE:
<223> OTHER INFORMATION: LC variable region 825 humanized version 2

<400> SEQUENCE: 48

Gly Tyr Asp Met Thr Gln Ser Pro Ser Ser Val Ser Ala Ser Val Gly
  1               5                  10                  15

Asp Arg Val Thr Ile Thr Cys Gln Ala Ser Glu Asn Ile Tyr Ser Thr
                 20                  25                  30

Leu Ala Trp Tyr Gln Gln Lys Pro Gly Lys Ala Pro Lys Leu Leu Ile
             35                  40                  45

Tyr Asp Ala Phe Asp Leu Ala Ser Gly Val Pro Ser Arg Phe Lys Gly
 50                  55                  60

Ser Gly Ser Gly Thr Glu Tyr Thr Leu Thr Ile Ser Ser Leu Gln Pro
 65                  70                  75                  80

Glu Asp Phe Ala Thr Tyr Tyr Cys Gln Gln Gly Tyr Ser Gly Thr Asn
                 85                  90                  95

Val Asp Asn Ala Phe Gly Gly Gly Thr Lys Val Glu Ile Lys
            100                 105                 110

<210> SEQ ID NO 49
<211> LENGTH: 110
<212> TYPE: PRT
<213> ORGANISM: Artificial Sequence
<220> FEATURE:
```

<223> OTHER INFORMATION: LC variable region 833 humanized version 1

<400> SEQUENCE: 49

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Gly Ser Glu
            20                  25                  30

Leu Ala Trp Tyr Gln Gln Lys Pro Gly Lys Ala Pro Lys Leu Leu Ile
        35                  40                  45

Tyr Arg Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Tyr Thr Tyr Ser Glu
                85                  90                  95

Ile Asp Asn Ala Phe Gly Gln Gly Thr Lys Val Glu Ile Lys
            100                 105                 110

<210> SEQ ID NO 50
<211> LENGTH: 110
<212> TYPE: PRT
<213> ORGANISM: Artificial Sequence
<220> FEATURE:
<223> OTHER INFORMATION: LC variable region 833 humanized version 2

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Gly Ser Glu
            20                  25                  30

Leu Ala Trp Tyr Gln Gln Lys Pro Gly Gln Ala Pro Lys Leu Leu Ile
        35                  40                  45

Tyr Arg Ala Ser Thr Leu Glu Ser Gly Val Pro Ser Arg Phe Ser Gly
    50                  55                  60

Ser Gly Ser Gly Thr Glu Phe Thr Phe Thr Ile Ser Ser Leu Gln Pro
65                  70                  75                  80

Glu Asp Leu Ala Thr Tyr Tyr Cys Gln Gln Gly Tyr Thr Tyr Ser Glu
                85                  90                  95

Ile Asp Asn Ala Phe Gly Gln Gly Thr Lys Leu Glu Ile Lys
            100                 105                 110

<210> SEQ ID NO 51
<211> LENGTH: 110
<212> TYPE: PRT
<213> ORGANISM: Artificial Sequence
<220> FEATURE:
<223> OTHER INFORMATION: LC variable region 833 humanized version 3

<400> SEQUENCE: 51

Ala Tyr Asp Met Thr Gln Ser Pro Ser Ser Val Ser Ala Ser Val Gly
1               5                   10                  15

Asp Arg Val Thr Ile Thr Cys Gln Ala Ser Gln Ser Ile Gly Ser Glu
            20                  25                  30

Leu Ala Trp Tyr Gln Gln Lys Pro Gly Lys Ala Pro Lys Leu Leu Ile
        35                  40                  45

Tyr Arg Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro

```
                65                  70                  75                  80
Glu Asp Phe Ala Thr Tyr Tyr Cys Gln Gln Gly Tyr Thr Tyr Ser Glu
                    85                  90                  95

Ile Asp Asn Ala Phe Gly Gly Gly Thr Lys Val Glu Ile Lys
                100                 105                 110

<210> SEQ ID NO 52
<211> LENGTH: 120
<212> TYPE: PRT
<213> ORGANISM: Artificial Sequence
<220> FEATURE:
<223> OTHER INFORMATION: H8 HC

<400> SEQUENCE: 52

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Lys Gln Ser Pro Gly Gln Gly Leu Glu Trp Ile
        35                  40                  45

Gly Arg Ile Asn Pro Asn Asn Gly Val Thr Leu Tyr Asn Gln Lys Phe
    50                  55                  60

Lys Asp Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Thr Met Ile Thr Asn Tyr Val Met Asp Tyr Trp Gly Gln
                100                 105                 110

Gly Thr Leu Val Thr Val Ser Ser
            115                 120

<210> SEQ ID NO 53
<211> LENGTH: 107
<212> TYPE: PRT
<213> ORGANISM: Artificial Sequence
<220> FEATURE:
<223> OTHER INFORMATION: H8 LC

<400> SEQUENCE: 53

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Ser Tyr Thr Ser Arg Tyr Ala Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Phe Cys Gln Gln Asp Tyr Asn Ser Pro Pro
                85                  90                  95

Thr Phe Gly Gly Gly Thr Lys Leu Glu Ile Lys
                100                 105

<210> SEQ ID NO 54
<211> LENGTH: 21
<212> TYPE: PRT
<213> ORGANISM: Artificial Sequence
<220> FEATURE:
```

<223> OTHER INFORMATION: HAVT20 leader sequence

<400> SEQUENCE: 54

Met Ala Cys Pro Gly Phe Leu Trp Ala Leu Val Ile Ser Thr Cys Leu
1               5                   10                  15

Glu Phe Ser Met Ala
            20

<210> SEQ ID NO 55
<211> LENGTH: 330
<212> TYPE: PRT
<213> ORGANISM: Artificial Sequence
<220> FEATURE:
<223> OTHER INFORMATION: Human IgG1 antibody HC constant region

<400> SEQUENCE: 55

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

```
Gln Lys Ser Leu Ser Leu Ser Pro Gly Lys
            325                 330
```

<210> SEQ ID NO 56
<211> LENGTH: 107
<212> TYPE: PRT
<213> ORGANISM: Artificial Sequence
<220> FEATURE:
<223> OTHER INFORMATION: Human IgG antibody LC kappa constant region

<400> SEQUENCE: 56

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 57
<211> LENGTH: 19
<212> TYPE: PRT
<213> ORGANISM: Artificial Sequence
<220> FEATURE:
<223> OTHER INFORMATION: rabbit leader sequence for heavy chain

<400> SEQUENCE: 57

```
Met Gly Trp Thr Leu Val Phe Leu Phe Leu Leu Ser Val Thr Ala Gly
1               5                   10                  15

Val His Ser
```

<210> SEQ ID NO 58
<211> LENGTH: 20
<212> TYPE: PRT
<213> ORGANISM: Artificial Sequence
<220> FEATURE:
<223> OTHER INFORMATION: Rabbit leader sequence for light chain

<400> SEQUENCE: 58

```
Met Val Ser Ser Ala Gln Phe Leu Gly Leu Leu Leu Leu Cys Phe Gln
1               5                   10                  15

Gly Thr Arg Cys
            20
```

<210> SEQ ID NO 59
<211> LENGTH: 121
<212> TYPE: PRT
<213> ORGANISM: Artificial Sequence
<220> FEATURE:
<223> OTHER INFORMATION: HC variable region 825 humanized version 1 41C

<400> SEQUENCE: 59

```
Glu Val Gln Leu Val Glu Ser Gly Gly Asp Leu Ala Gln Pro Gly Gly
1               5                   10                  15
```

-continued

```
Ser Leu Arg Leu Ser Cys Ala Val Ser Gly Ile Asp Leu Ser Ser Tyr
            20                  25                  30

Gly Met Gly Trp Val Arg Gln Ala Cys Gly Lys Gly Leu Glu Trp Val
        35                  40                  45

Ser Ile Ile Ser Arg Asn Ser Val Thr Tyr Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Thr Ser Leu Arg Ala Glu Asp Thr Ala Leu Tyr Phe Cys Ala
                85                  90                  95

Arg Arg Ala Thr Tyr Ser Gly Ala Leu Gly Tyr Phe Asp Ile Trp Gly
            100                 105                 110

Gln Gly Thr Leu Val Thr Val Ser Ser
        115                 120
```

<210> SEQ ID NO 60
<211> LENGTH: 121
<212> TYPE: PRT
<213> ORGANISM: Artificial Sequence
<220> FEATURE:
<223> OTHER INFORMATION: HC variable region 825 humanized version 2 41C

<400> SEQUENCE: 60

```
Glu Val Gln Leu Glu Glu Ser Gly Gly Gly Leu Val Lys Pro Gly Gly
1               5                   10                  15

Ser Leu Arg Leu Ser Cys Ala Ala Ser Gly Ile Asp Leu Ser Ser Tyr
            20                  25                  30

Gly Met Gly Trp Val Arg Gln Ala Cys Gly Lys Gly Leu Glu Trp Val
        35                  40                  45

Ser Ile Ile Ser Arg Asn Ser Val Thr Tyr Tyr Ala Thr Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Ala Thr Tyr Ser Gly Ala Leu Gly Tyr Phe Asp Ile Trp Gly
            100                 105                 110

Arg Gly Thr Leu Val Thr Val Ser Ser
        115                 120
```

<210> SEQ ID NO 61
<211> LENGTH: 122
<212> TYPE: PRT
<213> ORGANISM: Artificial Sequence
<220> FEATURE:
<223> OTHER INFORMATION: HC variable region 833 humanized version 1 41C

<400> SEQUENCE: 61

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Ile Asp Leu Ser His Tyr
            20                  25                  30

Val Val Gly Trp Val Arg Gln Ala Cys Gly Lys Gly Leu Glu Trp Val
        35                  40                  45

Ser Ile Ile Tyr Gly Ser Gly Arg Thr Tyr Tyr Ala Asn Trp Ala Lys
    50                  55                  60

Gly Arg Phe Thr Ile Ser Lys Asp Asn Ser Lys Asn Thr Leu Tyr Val
65                  70                  75                  80
```

Arg Met Asn Ser Leu Arg Ala Glu Asp Thr Ala Val Tyr Tyr Cys Ala
                85                  90                  95

Arg Asp Ala Ser Val Ser Val Tyr Tyr Trp Gly Tyr Phe Asp Leu Trp
            100                 105                 110

Gly Gln Gly Thr Leu Val Thr Val Ser Ser
        115                 120

<210> SEQ ID NO 62
<211> LENGTH: 122
<212> TYPE: PRT
<213> ORGANISM: Artificial Sequence
<220> FEATURE:
<223> OTHER INFORMATION: HC variable region 833 humanized version 2 41C

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Leu Ser His Tyr
            20                  25                  30

Val Val Gly Trp Val Arg Gln Ala Cys Gly Lys Gly Leu Glu Trp Val
        35                  40                  45

Ser Ile Ile Tyr Gly Ser Gly Arg Thr Tyr Tyr Ala Asn Trp Ala Lys
    50                  55                  60

Gly Arg Phe Thr Ile Ser Arg Asp Asn Ser Lys Asn Thr Leu Phe Leu
65                  70                  75                  80

Arg Met Asn Ser Leu Arg Val Glu Asp Thr Ala Val Tyr Phe Cys Ala
                85                  90                  95

Arg Asp Ala Ser Val Ser Val Tyr Tyr Trp Gly Tyr Phe Asp Leu Trp
            100                 105                 110

Gly Gln Gly Thr Leu Val Thr Val Ser Ser
        115                 120

<210> SEQ ID NO 63
<211> LENGTH: 122
<212> TYPE: PRT
<213> ORGANISM: Artificial Sequence
<220> FEATURE:
<223> OTHER INFORMATION: HC variable region 833 humanized version 3 41C

<400> SEQUENCE: 63

Glu Val Gln Leu Glu Glu Ser Gly Gly Gly Leu Val Lys Pro Gly Gly
1               5                   10                  15

Ser Leu Arg Leu Ser Cys Ala Ala Ser Gly Ile Asp Leu Ser His Tyr
            20                  25                  30

Val Val Gly Trp Val Arg Gln Ala Cys Gly Lys Gly Leu Glu Trp Val
        35                  40                  45

Ser Ile Ile Tyr Gly Ser Gly Arg Thr Tyr Tyr Ala Asn Trp Ala Lys
    50                  55                  60

Gly Arg Phe Thr Ile Ser Arg Asp Asn Ser Lys Asn Thr Leu Tyr Leu
65                  70                  75                  80

```
Gln Met Asn Ser Leu Arg Ala Glu Asp Thr Ala Val Tyr Tyr Cys Ala
                85                  90                  95

Arg Asp Ala Ser Val Ser Val Tyr Tyr Trp Gly Tyr Phe Asp Leu Trp
            100                 105                 110

Gly Arg Gly Thr Leu Val Thr Val Ser Ser
        115                 120

<210> SEQ ID NO 64
<211> LENGTH: 121
<212> TYPE: PRT
<213> ORGANISM: Artificial Sequence
<220> FEATURE:
<223> OTHER INFORMATION: HC variable region 833 humanized version 4 41C

<400> SEQUENCE: 64

Gln Ser Leu Glu Glu Ser Gly Gly Gly Leu Val Gln Pro Gly Gly Ser
1               5                   10                  15

Leu Arg Leu Ser Cys Ala Ala Ser Gly Ile Asp Leu Ser His Tyr Val
                20                  25                  30

Val Gly Trp Val Arg Gln Ala Cys Gly Lys Gly Leu Glu Trp Ile Gly
            35                  40                  45

Ile Ile Tyr Gly Ser Gly Arg Thr Tyr Tyr Ala Asn Trp Ala Lys Gly
    50                  55                  60

Arg Phe Thr Ile Ser Arg His Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Asp Ala Ser Val Ser Val Tyr Tyr Trp Gly Tyr Phe Asp Leu Trp Gly
            100                 105                 110

Gln Gly Thr Leu Val Thr Val Ser Ser
        115                 120
```

ANTI-5T4 ANTIBODIES AND ANTIBODY-DRUG CONJUGATES

FIELD OF THE INVENTION

The present invention relates to antibodies against the 5T4 (oncofoetal) antigen and corresponding antibody-drug conjugates (ADCs).

BACKGROUND OF THE PRESENT INVENTION

The 5T4 oncofoetal antigen is a 72 kDa glycoprotein defined by a monoclonal antibody raised against wheat germ agglutinin isolated glycoproteins from human placental syncytiotrophoblast microvillus membrane. This monoclonal antibody (mAb) was named 5T4 in WO89/07947. Whereas the 5T4 antigen has a limited expression in normal tissue, it is (over)expressed by various types of cancer cells. This renders the 5T4 antigen a specific cancer target and a potential and promising therapeutic target. However, although the target was discovered in the late eighties, approved therapeutic antibodies are still not available.

WO2006/031653 discloses the original mAb 5T4, i.e., H8 and its humanized version, both of which are not cross-reactive towards various non-human animal species typically used in in vivo preclinical (toxicity) studies. These preclinical studies aim to identify an initial safe dose for subsequent dose escalation schemes in humans; to identify healthy tissues or organs that are potential targets of reversible or irreversible toxic effects; and to identify safety parameters for clinical monitoring. For biopharmaceuticals, such as monoclonal antibodies, regulatory guidelines require testing in at least one relevant species (e.g. ICH S6 regulatory guideline). The species is not relevant in case the monoclonal antibody is not cross-reactive for the species and therefore insufficiently potent in said species. In such cases an alternative animal model may be used, e.g. a genetically modified species. However, this will require extensive effort not only to develop the model, but also to be able to provide an acceptable scientific justification to the regulatory authorities.

WO2007/106744 discloses the anti-5T4 antibodies A1, A2 and A3, but although these three antibodies exhibit some cross-reactivity towards non-human animal species, e.g. cynomolgus monkey, their affinities for human 5T4 are much lower than the affinity of H8 for human 5T4.

Anti-5T4 antibodies H8, A1, A2 and A3 linked via 4-(4'-acetylphenoxy)-butanoic acid to calicheamicin were disclosed in WO2007/106744 on p. 73. WO2012/131527 discloses A1 linked to maleimidocapronic-monomethylauristatin F (A1-mc-MMAF).

Only a few therapies targeting the 5T4 antigen have reached the clinical trial stage. The vaccine of modified vaccinia virus Ankara (MVA) vector encoding the 5T4 antigen induces an endogenous antibody response against the 5T4 antigen, but its phase III study on metastatic renal cancer failed to meet its primary end point of increased survival. Another example is naptumomab estafenatox, which is the Fab fragment of mAb 5T4 conjugated to a modified Staphylococcal enterotoxin E. This conjugate is thought to activate a T-cell response in the proximity of the tumour. However, a randomized phase II/III study of naptumomab estafenatox plus IFN-α versus IFN-α in advanced renal cell carcinoma did not meet its primary endpoint of prolonged survival. Recently as well, clinical development evaluating the A1-mc-MMAF ADC was discontinued. Currently, no active clinical trials are listed in the US and EU clinical trials registers.

WO 2015/155345 discloses new anti-5T4 antibodies and corresponding ADCs wherein an anti-5T4 antibody is (site-specifically) linked to a pyrrolobenzodiazepine (PDB) dimer or to a tubulysin. However, no clinical data is yet available.

The above leads to the conclusion that the clinically tested 5T4 targeted therapies, i.e. antibodies, antibody-drug conjugates and vaccines, do not measure up to the requirements of a cancer therapeutic. Therefore, there is a need for new antibodies against the 5T4 antigen and for corresponding antibody-drug conjugates for cancer therapy. To determine the suitability of these antibodies and corresponding ADCs in a preclinical setting, such antibodies should be cross-reactive for the 5T4 antigen of non-human animal species relevant for the preclinical development of a drug candidate.

BRIEF DESCRIPTION OF THE PRESENT INVENTION

The present invention relates to antibodies against the human 5T4 oncofoetal antigen and corresponding ADCs that are suitable for testing in clinical trials. Suitable antibodies and corresponding ADCs in a preclinical setting should be cross-reactive for the 5T4 antigen of non-human animal species relevant for preclinical development of a drug candidate.

Preferably, the antibodies are cross-reactive for humans and cynomolgus monkeys and exhibit an affinity for human 5T4 antigen (hu 5T4) which is in the same order of magnitude as their affinity for cynomolgus monkey 5T4 antigen (cyno 5T4).

The invention further relates to the use of the antibodies and corresponding ADCs in the treatment of solid tumours and haematological malignancies.

DETAILED DESCRIPTION OF THE PRESENT INVENTION

Figure 1A:
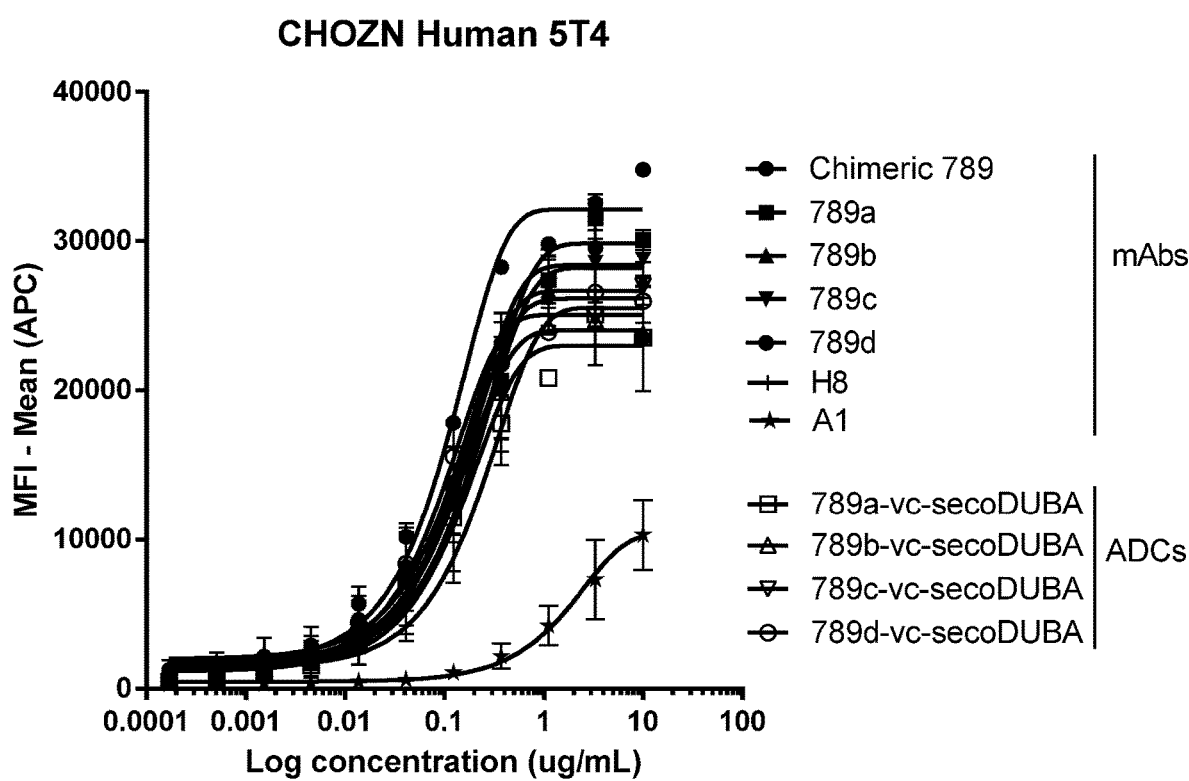
FIG. 1 shows the binding of chimeric mAbs, humanized mAbs with HC-41C mutation and corresponding anti-5T4 ADCs to hu 5T4-expressing CHO cells (CHOZN) versus that of H8 and A1 (FIG. 1A clone 789, FIG. 1B clone 833, FIG. 1C clone 825).

Whereas 5T4 oncofoetal antigen has a limited expression in normal tissues, it is (over)expressed by various cancer cells, thus rendering the 5T4 antigen a specific cancer target and a potential and promising therapeutic target. However, although the target was discovered in the late eighties, there currently are no approved therapeutics directed towards this target.

The present invention relates to antibodies against the 5T4 antigen and corresponding antibody-drug conjugates (ADCs), which are cross-reactive for cyno 5T4 and also exhibit excellent affinity for hu 5T4 antigen. The anti-5T4 antibodies and ADCs according to the invention show an affinity for cyno 5T4 antigen in the same order of magnitude as their affinity for hu 5T4. The term "same order of magnitude" means that the affinities for hu and cyno 5T4 antigen differ less than a factor ten from each other. The anti-5T4 antibodies of the invention have an improved affinity for hu 5T4 antigen compared to the prior art anti-5T4 antibodies A1 and A3, and an improved affinity for cyno 5T4 antigen compared to the prior art anti-5T4 antibody H8. Affinity is preferably measured as $EC_{50}$ in µg/ml in a cell-based assay using cells expressing hu or cyno 5T4 antigen. The present inventors measured the $EC_{50}$ on various cells, such as MDA-MB-468, PA-1 and Chinese Hamster Ovary (CHO) cells engineered to express hu 5T4 or cyno 5T4. The antibodies of the invention typically exhibit an $EC_{50}$ lower than 0.8 µg/ml measured using cells expressing hu 5T4 or cyno 5T4 antigen after incubation of the cells with the antibodies for 30 minutes at 4° C.

Prior art anti-5T4 antibody A1 is characterised by a heavy chain (HC) variable region (VR) of the mouse A1 amino acid sequence from U.S. Pat. No. 8,044,178, SEQ ID NO:2, positions 20-138 and a light chain (LC) VR of the mouse A1 amino acid sequence from U.S. Pat. No. 8,044,178, SEQ ID NO:4, positions 21-127. Prior art anti-5T4 antibody A3 is characterised by an HCVR of the mouse A3 amino acid sequence from U.S. Pat. No. 8,044,178, SEQ ID NO:10, positions 20-141 and an LCVR of the mouse A3 amino acid sequence from U.S. Pat. No. 8,044,178, SEQ ID NO:12, positions 21-127. Prior art anti-5T4 antibody H8 is characterised by the HCVR of SEQ ID NO:52 and the LCVR of SEQ ID NO:53.

The term "antibody" as used throughout the present specification refers to a monoclonal antibody (mAb) comprising two heavy chains and two light chains or an antigen binding fragment thereof, e.g. a Fab, Fab' or F(ab')$_2$ fragment, a single chain (sc) antibody, a scFv, a single domain (sd) antibody, a diabody, or a minibody. Antibodies may be of any isotype such as IgG, IgA or IgM antibodies. Preferably, the antibody is an IgG antibody, more preferably an IgG1 or IgG2 antibody. The antibodies may be chimeric, humanized or human. Preferably, the antibodies of the invention are humanized. Even more preferably, the antibody is a humanized or human IgG antibody, most preferably a humanized or human IgG1 mAb. The antibody may have κ (kappa) or λ (lambda) light chains, preferably κ (kappa) light chains, i.e., a humanized or human IgG1-κ antibody.

In humanized antibodies, the antigen-binding complementarity determining regions (CDRs) in the variable regions of the HC and LC are derived from antibodies from a non-human species, commonly mouse, rat or rabbit. These non-human CDRs may be placed within a human framework (FR1, FR2, FR3 and FR4) of the variable regions of the HC and LC. Selected amino acids in the human FRs may be exchanged for the corresponding original non-human species amino acids to improve binding affinity, while retaining low immunogenicity. Alternatively, selected amino acids of the original non-human species FRs are exchanged for their corresponding human amino acids to reduce immunogenicity, while retaining the antibody's binding affinity. The thus humanized variable regions are combined with human constant regions.

The present invention particularly relates to an anti-5T4 antibody comprising HCVR and LCVR CDRs selected from the group consisting of:
a. CDR1, CDR2 and CDR3 amino acid sequences of SEQ ID NO:1 and CDR1, CDR2 and CDR3 amino acid sequences of SEQ ID NO:2;
b. CDR1, CDR2 and CDR3 amino acid sequences of SEQ ID NO:3 and CDR1, CDR2 and CDR3 amino acid sequences of SEQ ID NO:4;
c. CDR1, CDR2 and CDR3 amino acid sequences of SEQ ID NO:5 and CDR1, CDR2 and CDR3 amino acid sequences of SEQ ID NO:6;
d. CDR1, CDR2 and CDR3 amino acid sequences of SEQ ID NO:7 and CDR1, CDR2 and CDR3 amino acid sequences of SEQ ID NO:8;
e. CDR1, CDR2 and CDR3 amino acid sequences of SEQ ID NO:9 and CDR1, CDR2 and CDR3 amino acid sequences of SEQ ID NO:10;
f. CDR1, CDR2 and CDR3 amino acid sequences of SEQ ID NO:11 and CDR1, CDR2 and CDR3 amino acid sequences of SEQ ID NO:12;
g. CDR1, CDR2 and CDR3 amino acid sequences of SEQ ID NO:13 and CDR1, CDR2 and CDR3 amino acid sequences of SEQ ID NO:14;
h. CDR1, CDR2 and CDR3 amino acid sequences of SEQ ID NO:15 and CDR1, CDR2 and CDR3 amino acid sequences of SEQ ID NO:16;
i. CDR1, CDR2 and CDR3 amino acid sequences of SEQ ID NO:17 and CDR1, CDR2 and CDR3 amino acid sequences of SEQ ID NO:18;
j. CDR1, CDR2 and CDR3 amino acid sequences of SEQ ID NO:19 and CDR1, CDR2 and CDR3 amino acid sequences of SEQ ID NO:20;
k. CDR1, CDR2 and CDR3 amino acid sequences of SEQ ID NO:21 and CDR1, CDR2 and CDR3 amino acid sequences of SEQ ID NO:22;
l. CDR1, CDR2 and CDR3 amino acid sequences of SEQ ID NO:23 and CDR1, CDR2 and CDR3 amino acid sequences of SEQ ID NO:24;
m. CDR1, CDR2 and CDR3 amino acid sequences of SEQ ID NO:25 and CDR1, CDR2 and CDR3 amino acid sequences of SEQ ID NO:26;
n. CDR1, CDR2 and CDR3 amino acid sequences of SEQ ID NO:27 and CDR1, CDR2 and CDR3 amino acid sequences of SEQ ID NO:28;
o. CDR1, CDR2 and CDR3 amino acid sequences of SEQ ID NO:29 and CDR1, CDR2 and CDR3 amino acid sequences of SEQ ID NO:30;
p. CDR1, CDR2 and CDR3 amino acid sequences of SEQ ID NO:31 and CDR1, CDR2 and CDR3 amino acid sequences of SEQ ID NO:32; and
q. CDR1, CDR2 and CDR3 amino acid sequences of SEQ ID NO:33 and CDR1, CDR2 and CDR3 amino acid sequences of SEQ ID NO:34.

For clarity, the CDR1, CDR2 and CDR3 sequences of the HCVR and the CDR1, CDR2 and CDR3 sequences of the LCVR of the antibodies listed under a to q hereinabove are underlined in the sequence listings given at the end of the present description.

In one embodiment, the anti-5T4 antibody of the invention comprises HCVR and LCVR CDRs selected from the group consisting of:
a. CDR1, CDR2 and CDR3 amino acid sequences of SEQ ID NO:1 and CDR1, CDR2 and CDR3 amino acid sequences of SEQ ID NO:2;

b. CDR1, CDR2 and CDR3 amino acid sequences of SEQ ID NO:5 and CDR1, CDR2 and CDR3 amino acid sequences of SEQ ID NO:6;
c. CDR1, CDR2 and CDR3 amino acid sequences of SEQ ID NO:11 and CDR1, CDR2 and CDR3 amino acid sequences of SEQ ID NO:12;
d. CDR1, CDR2 and CDR3 amino acid sequences of SEQ ID NO:13 and CDR1, CDR2 and CDR3 amino acid sequences of SEQ ID NO:14;
e. CDR1, CDR2 and CDR3 amino acid sequences of SEQ ID NO:17 and CDR1, CDR2 and CDR3 amino acid sequences of SEQ ID NO:18; and
f. CDR1, CDR2 and CDR3 amino acid sequences of SEQ ID NO:25 and CDR1, CDR2 and CDR3 amino acid sequences of SEQ ID NO:26.

In a preferred embodiment, the anti-5T4 antibody of the invention comprises HCVR and LCVR CDRs selected from the group consisting of:
 a. CDR1, CDR2 and CDR3 amino acid sequences of SEQ ID NO:1 and CDR1, CDR2 and CDR3 amino acid sequences of SEQ ID NO:2;
 b. CDR1, CDR2 and CDR3 amino acid sequences of SEQ ID NO:5 and CDR1, CDR2 and CDR3 amino acid sequences of SEQ ID NO:6; and
 c. CDR1, CDR2 and CDR3 amino acid sequences of SEQ ID NO:11 and CDR1, CDR2 and CDR3 amino acid sequences of SEQ ID NO:12.

In a more preferred embodiment, the anti-5T4 antibody of the invention comprises HCVR and LCVR CDRs selected from the group consisting of:
 a. CDR1, CDR2 and CDR3 amino acid sequences of SEQ ID NO:5 and CDR1, CDR2 and CDR3 amino acid sequences of SEQ ID NO:6; and
 b. CDR1, CDR2 and CDR3 amino acid sequences of SEQ ID NO:11 and CDR1, CDR2 and CDR3 amino acid sequences of SEQ ID NO:12.

In another embodiment, the invention relates to a humanized anti-5T4 antibody comprising a HCVR and a LCVR selected from the group consisting of:
 a. HCVR amino acid sequence of SEQ ID NO:35 and LCVR amino acid sequence of SEQ ID NO:45;
 b. HCVR amino acid sequence of SEQ ID NO:36 and LCVR amino acid sequence of SEQ ID NO:45;
 c. HCVR amino acid sequence of SEQ ID NO:37 and LCVR amino acid sequence of SEQ ID NO:44;
 d. HCVR amino acid sequence of SEQ ID NO:37 and LCVR amino acid sequence of SEQ ID NO:46;
 e. HCVR amino acid sequence of SEQ ID NO:40 and LCVR amino acid sequence of SEQ ID NO:51;
 f. HCVR amino acid sequence of SEQ ID NO:41 and LCVR amino acid sequence of SEQ ID NO:51;
 g. HCVR amino acid sequence of SEQ ID NO:42 and LCVR amino acid sequence of SEQ ID NO:49;
 h. HCVR amino acid sequence of SEQ ID NO:43 and LCVR amino acid sequence of SEQ ID NO:50;
 i. HCVR amino acid sequence of SEQ ID NO:38 and LCVR amino acid sequence of SEQ ID NO:47;
 j. HCVR amino acid sequence of SEQ ID NO:39 and LCVR amino acid sequence of SEQ ID NO:47; and
 k. HCVR amino acid sequence of SEQ ID NO:39 and LCVR amino acid sequence of SEQ ID NO:48.

In a first embodiment of the invention the humanized anti-5T4 antibody comprises HCVR amino acid sequence of SEQ ID NO:35 and LCVR amino acid sequence of SEQ ID NO:45.

In a second embodiment of the invention the humanized anti-5T4 antibody comprises HCVR amino acid sequence of SEQ ID NO:36 and LCVR amino acid sequence of SEQ ID NO:45.

In a third embodiment of the invention the humanized anti-5T4 antibody comprises HCVR amino acid sequence of SEQ ID NO:37 and LCVR amino acid sequence of SEQ ID NO:44.

In a fourth embodiment of the invention the humanized anti-5T4 antibody comprises HCVR amino acid sequence of SEQ ID NO:37 and LCVR amino acid sequence of SEQ ID NO:46.

In a fifth, preferred embodiment of the invention the humanized anti-5T4 antibody comprises HCVR amino acid sequence of SEQ ID NO:40 and LCVR amino acid sequence of SEQ ID NO:51.

In a sixth, preferred embodiment of the invention the humanized anti-5T4 antibody comprises HCVR amino acid sequence of SEQ ID NO:41 and LCVR amino acid sequence of SEQ ID NO:51.

In a seventh, preferred embodiment of the invention the humanized anti-5T4 antibody comprises HCVR amino acid sequence of SEQ ID NO:42 and LCVR amino acid sequence of SEQ ID NO:49.

In an eighth, preferred embodiment of the invention the humanized anti-5T4 antibody comprises HCVR amino acid sequence of SEQ ID NO:43 and LCVR amino acid sequence of SEQ ID NO:50.

In a ninth, preferred embodiment of the invention the humanized anti-5T4 antibody comprises HCVR amino acid sequence of SEQ ID NO:38 and LCVR amino acid sequence of SEQ ID NO:47.

In a tenth embodiment of the invention the humanized anti-5T4 antibody comprises HCVR amino acid sequence of SEQ ID NO:39 and LCVR amino acid sequence of SEQ ID NO:47.

In an eleventh, preferred embodiment of the invention the humanized anti-5T4 antibody comprises HCVR amino acid sequence of SEQ ID NO:39 and LCVR amino acid sequence of SEQ ID NO:48.

The present invention additionally relates to an ADC, wherein a linker drug is conjugated to an anti-5T4 antibody according to the invention.

In one embodiment, the present invention relates to an ADC wherein a linker drug is randomly conjugated to an anti-5T4 antibody according to the invention through a native cysteine liberated through reduction of the interchain disulfide bonds.

In another embodiment, the present invention relates to an ADC wherein a linker drug is site-specifically conjugated to an anti-5T4 antibody according to the invention through an engineered cysteine (site-specific ADC).

The anti-5T4 antibodies comprising at least one engineered cysteine in the HC or LC have several advantages. Antibodies comprising engineered cysteines provide the opportunity to prepare site-specific ADCs, can provide conjugation positions that show good reactivity with the linker drug, and at the same time have a reduced risk of forming additional disulfide bonds between antibodies (leading to aggregation) or disturbing the antibody structure. An additional advantage of having cysteines at specific positions in the HC or LC is the effect of decreased hydrophobicity of the resulting ADCs.

Multiple suitable conjugation positions for linker drug attachment have been identified in and in close proximity to cavities which are present in all antibody structures, i.e., with good accessibility of engineered cysteines at these locations as disclosed and claimed in WO2015/177360.

When linker drugs are conjugated at the specific positions of the anti-5T4 antibodies as claimed herein, said linker drug fits into the Fab cavity that is formed by the constant heavy chain 1 (CH1), variable heavy chain (VH), variable light chain (VL) and constant light chain (CL) regions of the antibody. As a result, the linker drug (most toxins/linker drugs are hydrophobic) is shielded from the aqueous environment surrounding the antibody and the ADC as such is less hydrophobic as compared to ADCs wherein the linker drug is conjugated through native interchain disulfide bond cysteines of the antibody and is much less hydrophobic as compared to ADCs wherein the linker drug is site-specifically conjugated at different positions where the linker drug is forced to the outside of the antibody, i.e., more exposed to the hydrophilic aqueous environment.

In a preferred embodiment of the present invention, the anti-5T4 antibody according to the invention comprises at least one engineered cysteine at a position in a HC variable region FR or a LC variable region FR. The term "engineered cysteine" as used throughout the present specification means replacing a non-cysteine amino acid in the HC or LC of an antibody by a cysteine. As is known by the person skilled in the art, this can be done either at the amino acid level or at the DNA level, e.g. by using site-directed mutagenesis. Preferably, such engineered cysteine is introduced by specific point mutations, replacing an existing amino acid in the original/parent antibody.

Preferably, the at least one engineered cysteine is present at one or more positions of the anti-5T4 antibodies according to the invention selected from HC 40, 41 and 89 (according to Kabat numbering); and LC 40 and 41 (according to Kabat numbering). The expression "Kabat numbering" refers to the numbering system commonly used for HC variable regions or LC variable regions of the compilation of antibodies in Kabat, E.A. et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable region. The Kabat numbering of residues may be determined for a given antibody by alignment at regions of homology of the sequence of the antibody with a "standard" Kabat numbered sequence.

In addition to the anti-5T4 antibodies comprising the HCVR and LCVR CDRs and the humanized antibodies comprising HCVRs and LCVRs as disclosed hereinabove, the present invention also relates to said antibodies comprising in the HC and/or LC at least one engineered cysteine at a position selected from HC 40, 41 and 89, and LC 40 and 41.

In a preferred embodiment, the anti-5T4 antibody of the invention comprises at least one engineered cysteine at a position selected from HC 40, 41 and 89, and LC 40 and 41 and comprises HCVR and HCVR CDRs selected from the group consisting of:
   a. CDR1, CDR2 and CDR3 amino acid sequences of SEQ ID NO:1 and CDR1, CDR2 and CDR3 amino acid sequences of SEQ ID NO:2;
   b. CDR1, CDR2 and CDR3 amino acid sequences of SEQ ID NO:5 and CDR1, CDR2 and CDR3 amino acid sequences of SEQ ID NO:6; and
   c. CDR1, CDR2 and CDR3 amino acid sequences of SEQ ID NO:11 and CDR1, CDR2 and CDR3 amino acid sequences of SEQ ID NO:12.

In another preferred embodiment, the invention relates to a humanized anti-5T4 antibody comprising at least one engineered cysteine at a position selected from HC 40, 41 and 89, and LC 40 and 41 and comprising HCVR and LCVR selected from the group consisting of:
   a. HC amino acid sequence of SEQ ID NO:40 and LC amino acid sequence of SEQ ID NO:51;
   b. HC amino acid sequence of SEQ ID NO:41 and LC amino acid sequence of SEQ ID NO:51;
   c. HC amino acid sequence of SEQ ID NO:42 and LC amino acid sequence of SEQ ID NO:49;
   d. HC amino acid sequence of SEQ ID NO:43 and LC amino acid sequence of SEQ ID NO:50;
   e. HC amino acid sequence of SEQ ID NO:38 and LC amino acid sequence of SEQ ID NO:47; and
   f. HC amino acid sequence of SEQ ID NO:39 and LC amino acid sequence of SEQ ID NO:48.

Positions HC 40, 41 and 89 and LC 40 and 41 are located in the variable region FRs of the antibody as well as in the Fab part of the antibody.

In a preferred embodiment, the present invention relates to an ADC wherein a linker drug is site-specifically conjugated to an anti-5T4 antibody according to the invention through an engineered cysteine at one or more positions of said anti-5T4 antibody selected from HC 40, 41 and 89 (according to Kabat numbering) and LC 40 and 41 (according to Kabat numbering).

The present inventors surprisingly have found that the site-specifically conjugated ADCs of the present invention show improved physicochemical, pharmacological and/or pharmacokinetic properties, as compared to conventional ADCs in which the linker drug is conjugated through native interchain disulfide bond cysteines of the anti-5T4 antibody.

Modification of the variable part of an antibody is generally avoided as it can lead to partial or complete loss of antigen binding affinities. However, contrary to the general expectations, it was found that specific residues in the FRs of the HC and LC of the antibody are both suitable for conjugation and do not lead to (significant) reduction of antigen binding after conjugation of the linker drug. In a particularly preferred embodiment, the present invention relates to an ADC wherein said engineered cysteine is at one or more positions of said anti-5T4 antibody selected from HC 40 and 41, and LC 40 and 41 (in the Fab part of said antibody). Preferably, said engineered cysteine is at position HC 41 or LC 40 or 41, more preferably at HC 41.

As it is known from the literature that tumour-associated proteases in the tumour microenvironment can partially cleave the Fc constant domains, under the hinge region, conjugation in the Fab part is preferred over conjugation in the Fc part. Cleavage of the Fc constant domains would result in loss of Fc-conjugated linker drugs, which in turn could lead to a decreased activity of the ADC in vivo. (Fan et al. Breast Cancer Res. 2012; 14: R116 and Brezsky et al. PNAS 2009; 106: 17864-17869). Moreover, conjugation to these positions in the Fab part also enables the use of antigen binding fragments of the anti-5T4 antibodies disclosed herein.

The (site-specific) ADCs in accordance with the present invention have binding affinities similar to the naked antibodies and excellent in vitro potency, and have an improved in vivo profile over the 5T4-targeting ADCs known from the prior art. It is expected that the site-specific ADCs in accordance with the present invention will exhibit low non-specific toxicity in vivo in comparison with the 5T4-targeting ADCs of the prior art. In the anti-5T4 ADCs of the invention the linker drug is shielded (rendering the ADCs less susceptible to cleavage by extracellular proteases) and thus the drug is less likely to be released prematurely.

In accordance with the present invention, any linker drug known in the art of ADCs can be used for (site-specific) conjugation to the antibodies according to the present invention, provided it has a chemical group which can react with the thiol group of a native or an engineered cysteine, typically a maleimide or haloacetyl group. Suitable linker drugs may comprise a duocarmycin, calicheamicin, pyrrolobenzodiazepine (PBD) dimer, maytansinoid or auristatin derivative as a cytotoxic drug. Either a cleavable or a non-cleavable linker may be used in accordance with the present invention. Preferably, the cytotoxic drug is a duocarmycin, a maytansinoid or an auristatin derivative. Suitable examples of maytansinoid drugs include DM1 and DM4. Suitable examples of auristatin drugs include MMAE and MMAF.

These abbreviations are well-known to the skilled artisan. Examples of suitable linker drugs known to the person skilled in the art include mc-vc-PAB-MMAE (also abbreviated as mc-vc-MMAE and vc-MMAE), mc-MMAF, and mc-vc-MMAF. Preferably, the linker used is a cleavable linker comprising valine-citrulline (vc) or valine-alanine (va).

The generic molecular structures of a (site-specific) vc-MMAE ADC and mc-MMAF ADC in accordance with the present invention are depicted below.

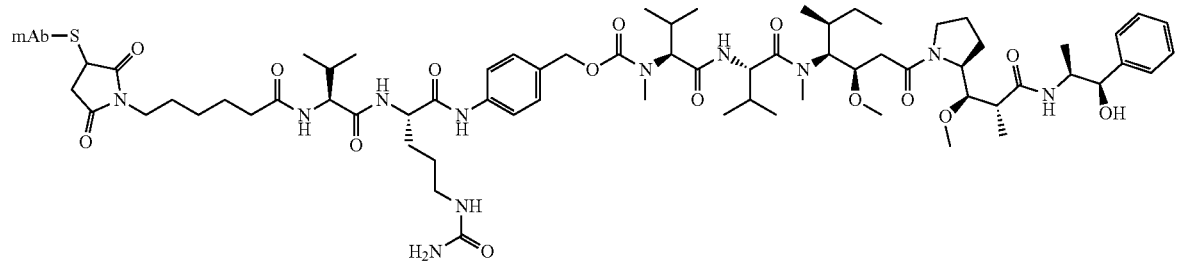

Molecular structure of vc-MMAE linked to a mAb

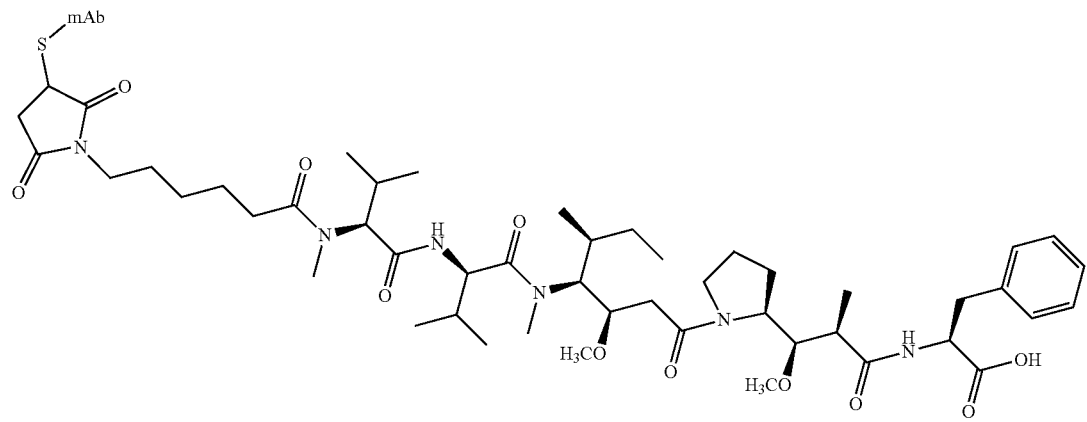

Molecular structure of mc-MMAF linked to a mAb

In one embodiment, the present invention relates to an ADC wherein the linker drug comprises a duocarmycin derivative.

Duocarmycins, first isolated from a culture broth of *Streptomyces* species, are members of a family of antitumour antibiotics that include duocarmycin A, duocarmycin SA, and CC-1065. Duocarmycins bind to the minor groove of DNA and subsequently cause irreversible alkylation of DNA. This disrupts the nucleic acid architecture, which eventually leads to tumour cell death.

WO2011/133039 discloses a series of linker drugs comprising a duocarmycin derivative of CC-1065. Suitable linker-duocarmycin derivatives to be used in accordance with the present invention are disclosed on pages 182-197. The chemical synthesis of a number of these linker drugs is described in Examples 1-12 of WO2011/133039.

In one embodiment, the present invention relates to an ADC of formula (I)

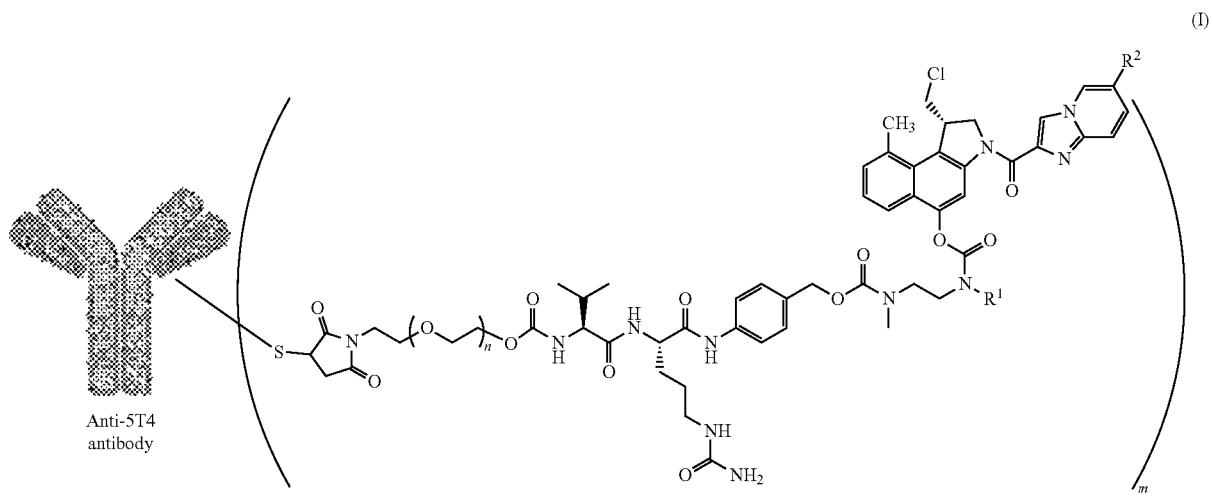

wherein
"Anti-5T4 antibody" is an anti-5T4 antibody according to the present invention either without or with at least one engineered cysteine in the HC or LC as disclosed herein,
n is 0-3, preferably 0-1,
m represents an average DAR of from 1 to 6, preferably of from 1 to 4,
$R^1$ is selected from y is 1-16, and
$R^2$ is selected from

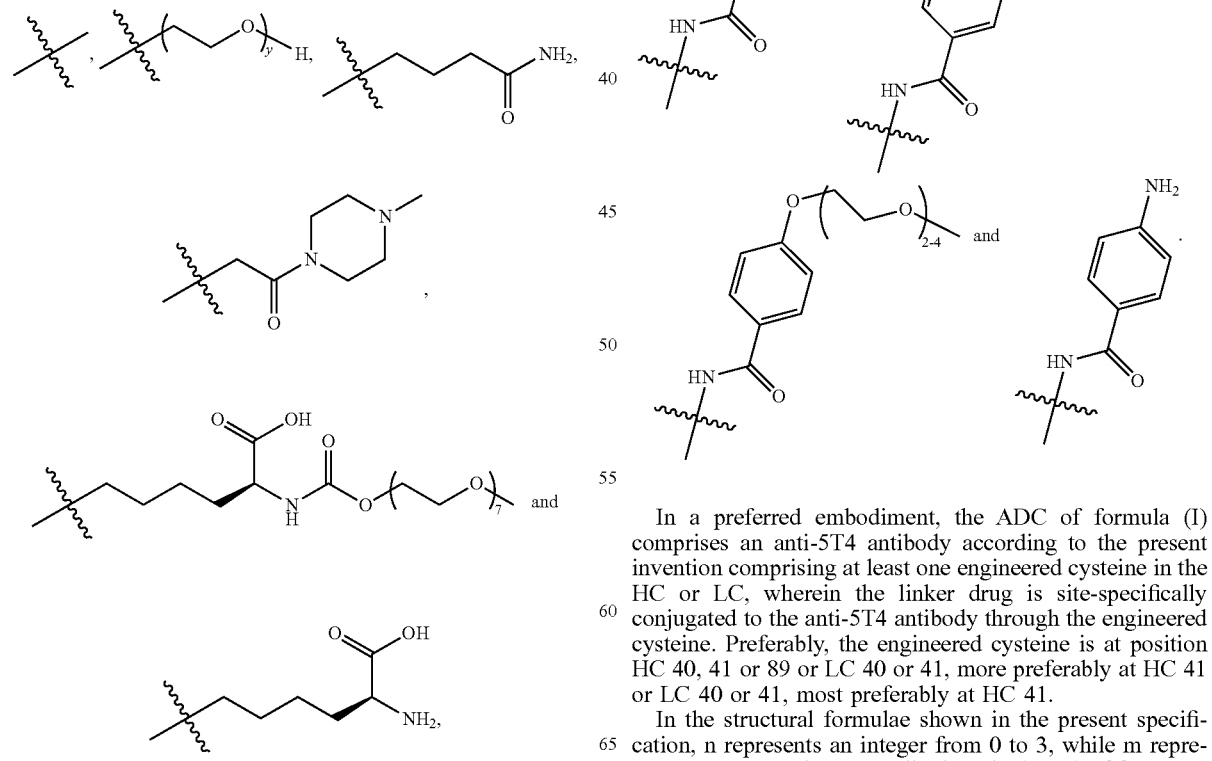

In a preferred embodiment, the ADC of formula (I) comprises an anti-5T4 antibody according to the present invention comprising at least one engineered cysteine in the HC or LC, wherein the linker drug is site-specifically conjugated to the anti-5T4 antibody through the engineered cysteine. Preferably, the engineered cysteine is at position HC 40, 41 or 89 or LC 40 or 41, more preferably at HC 41 or LC 40 or 41, most preferably at HC 41.

In the structural formulae shown in the present specification, n represents an integer from 0 to 3, while m represents an average drug-to-antibody ratio (DAR) of from 1 to 6. As is well-known in the art, the DAR and drug load distribution can be determined, for example, by using hydrophobic interaction chromatography (HIC) or reversed phase high-performance liquid chromatography (RP-HPLC). HIC is particularly suitable for determining the average DAR.

ADCs of formula (I) in accordance with the present invention can be obtained according to methods and procedures that are well known to a person skilled in the art.

A suitable method for the aspecific (random) conjugation of duocarmycin linker drugs, i.e., conjugation to a native cysteine, is disclosed in Example 15 of WO2011/133039, whereas Doronina et al. Bioconjugate Chem. 17 (2006): 114-124 describes aspecific conjugation with mc-MMAF.

Suitable methods for site-specifically conjugating linker drugs can for example be found in Examples 7 and 8 of WO2005/084390, which describe complete reduction strategies for (partial) loading of antibodies with the linker drug vc-MMAE, and in Examples 11 and 12 of WO2006/034488, which describe the site-specific conjugation of a maytansinoid (DM1)-comprising linker drug.

In a particular embodiment, the present invention relates to an ADC of formula (I) as disclosed hereinabove, wherein n is 0-1, m represents an average DAR of from 1 to 6, preferably of from 1 to 4, more preferably of from 1 to 2, even more preferably of from 1.5 to 2, most preferably of from 1.8 to 2, $R^1$ is selected from

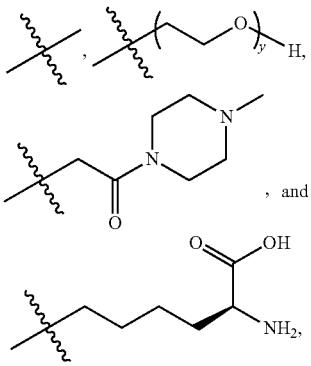

, and y is 1-16, preferably 1-4, and
$R^2$ is selected from

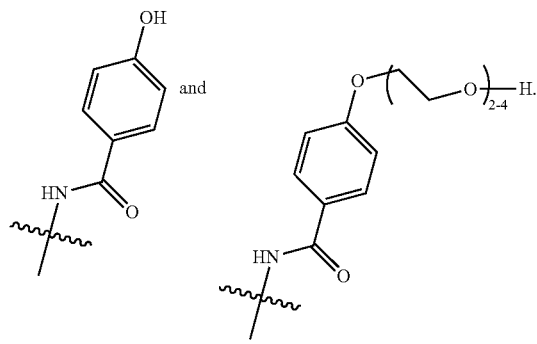

In a specific embodiment, the present invention relates to an ADC of structural formula (I) as disclosed hereinabove, wherein n is 0-1, m represents an average DAR of from 1.5 to 2, preferably of from 1.8 to 2, $R^1$ is

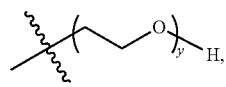

y is 1-4, and $R^2$ is selected from

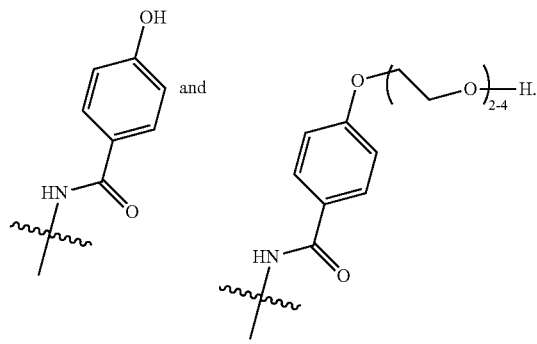

In a particularly preferred embodiment, the present invention relates to an ADC of formula (II)

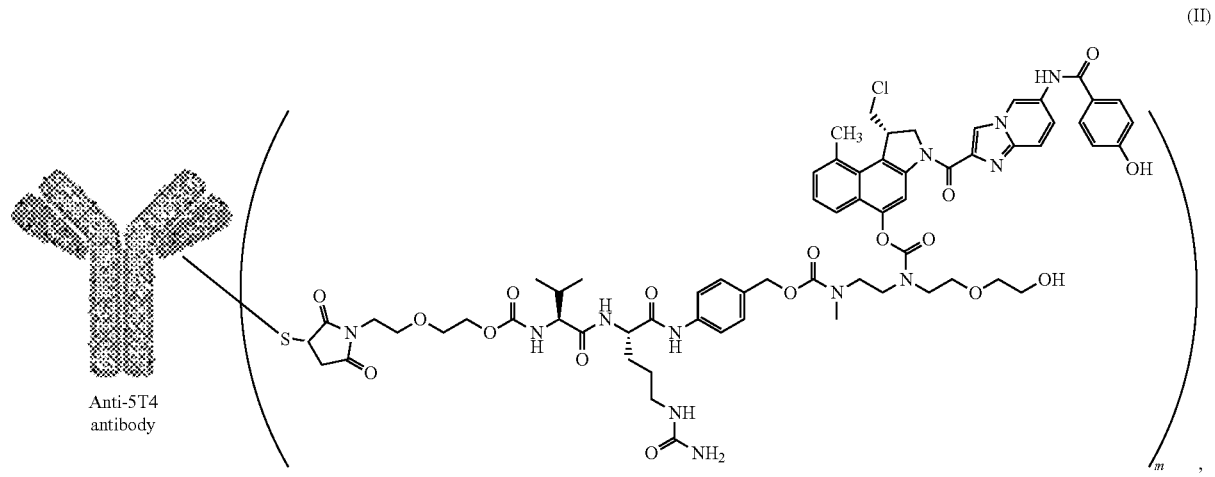

wherein "Anti-5T4 antibody" is an anti-5T4 antibody according to the present invention either without or with at least one engineered cysteine in the HC or LC as disclosed herein and m represents an average DAR of from 1.5 to 2, preferably of from 1.8 to 2.

In a preferred embodiment, the ADC of formula (II) comprises an anti-5T4 antibody according to the present invention comprising at least one engineered cysteine in the HC or LC, wherein the linker drug is site-specifically conjugated to the antibody through the engineered cysteine. Preferably, said engineered cysteine is at position HC 40, 41 or 89 or LC 40 or 41, more preferably at HC 41 or LC 40 or 41, most preferably at HC 41.

In a preferred embodiment, the present invention relates to an ADC of formula (II) comprising an anti-5T4 antibody comprising HCVR and LCVR CDRs selected from the group consisting of:
  a. CDR1, CDR2 and CDR3 amino acid sequences of SEQ ID NO:1 and CDR1, CDR2 and CDR3 amino acid sequences of SEQ ID NO:2;
  b. CDR1, CDR2 and CDR3 amino acid sequences of SEQ ID NO:5 and CDR1, CDR2 and CDR3 amino acid sequences of SEQ ID NO:6; and
  c. CDR1, CDR2 and CDR3 amino acid sequences of SEQ ID NO:11 and CDR1, CDR2 and CDR3 amino acid sequences of SEQ ID NO:12.

In a more preferred embodiment, the present invention relates to an ADC of formula (II) comprising a humanized anti-5T4 antibody comprising HCVR and LCVR selected from the group consisting of:
  a. HC amino acid sequence of SEQ ID NO:40 and LC amino acid sequence of SEQ ID NO:51;
  b. HC amino acid sequence of SEQ ID NO:41 and LC amino acid sequence of SEQ ID NO:51;
  c. HC amino acid sequence of SEQ ID NO:42 and LC amino acid sequence of SEQ ID NO:49;
  d. HC amino acid sequence of SEQ ID NO:43 and LC amino acid sequence of SEQ ID NO:50;
  e. HC amino acid sequence of SEQ ID NO:38 and LC amino acid sequence of SEQ ID NO:47; and
  f. HC amino acid sequence of SEQ ID NO:39 and LC amino acid sequence of SEQ ID NO:48.

In an even more preferred embodiment, the present invention relates to an ADC of formula (II) comprising an anti-5T4 antibody according to the present invention comprising at least one engineered cysteine at one or more positions selected from HC 40 and 41, and LC 40 and 41, wherein the linker drug is site-specifically conjugated to the anti-5T4 antibody through the engineered cysteine. Preferably, said engineered cysteine is at position HC 41 or LC 40 or 41, most preferably at HC 41.

In a most preferred embodiment, the present invention relates to an ADC of formula (II) comprising a humanized anti-5T4 antibody comprising HCVR and LCVR selected from the group consisting of:
  a. HCVR amino acid sequence of SEQ ID NO:61 and LCVR amino acid sequence of SEQ ID NO:51;
  b. HCVR amino acid sequence of SEQ ID NO:62 and LCVR amino acid sequence of SEQ ID NO:51;
  c. HCVR amino acid sequence of SEQ ID NO:63 and LCVR amino acid sequence of SEQ ID NO:49;
  d. HCVR amino acid sequence of SEQ ID NO:64 and LCVR amino acid sequence of SEQ ID NO:50;
  e. HCVR amino acid sequence of SEQ ID NO:59 and LCVR amino acid sequence of SEQ ID NO:47; and
  f. HCVR amino acid sequence of SEQ ID NO:60 and LCVR amino acid sequence of SEQ ID NO:48;

wherein the linker drug is site-specifically conjugated to the anti-5T4 antibody through the engineered cysteine at position HC 41.

The present invention further relates to a pharmaceutical composition comprising an anti-5T4 antibody or an anti-5T4 ADC as described hereinabove and one or more pharmaceutically acceptable excipients. Typical pharmaceutical formulations of therapeutic proteins such as mAbs and (monoclonal) ADCs take the form of lyophilized cakes (lyophilized powders), which require (aqueous) dissolution (i.e., reconstitution) before intravenous infusion, or frozen (aqueous) solutions, which require thawing before use.

Typically, the pharmaceutical composition is provided in the form of a lyophilized cake. Suitable pharmaceutically acceptable excipients for inclusion into the pharmaceutical composition (before freeze-drying) in accordance with the present invention include buffer solutions (e.g. citrate, histidine or succinate containing salts in water), lyoprotectants (e.g. sucrose, trehalose), tonicity modifiers (e.g. sodium chloride), surfactants (e.g. polysorbate), and bulking agents (e.g. mannitol, glycine). Excipients used for freeze-dried protein formulations are selected for their ability to prevent protein denaturation during the freeze-drying process as well as during storage. As an example, the sterile, lyophilized powder single-use formulation of Kadcyla™ (Roche) contains—upon reconstitution with Bacteriostatic or Sterile Water for Injection (BWFI or SWFI)—20 mg/mL ado-trastuzumab emtansine, 0.02% w/v polysorbate 20, 10 mM sodium succinate, and 6% w/v sucrose with a pH of 5.0.

The present invention further relates to an anti-5T4 antibody, ADC or pharmaceutical composition as described hereinabove for use as a medicament.

In one embodiment, the present invention relates to an anti-5T4 antibody, ADC or pharmaceutical composition as described hereinabove for use in the treatment of human solid tumours and haematological malignancies, preferably human solid tumours.

In a preferred embodiment, the present invention relates to an anti-5T4 antibody, an ADC or a pharmaceutical composition as described hereinabove, particularly an ADC comprising a duocarmycin derivative linker drug, for use in the treatment of human solid tumours selected from the group consisting of breast cancer, gastric cancer, colorectal cancer, ovarian cancer, lung cancer (especially non-small cell lung cancer (NSCLC) and small-cell lung cancer (SCLC)), and (malignant pleural) mesothelioma.

In a further embodiment, the present invention relates to an anti-5T4 antibody, ADC or pharmaceutical composition as described hereinabove, particularly an ADC comprising a duocarmycin derivative linker drug, for use in the treatment of human haematological malignancies, particularly leukaemia, selected from the group consisting of acute lymphoblastic and myeloid leukaemia (ALL and AML, respectively).

The present invention further relates to the use of a sequentially or simultaneously administered combination of an anti-5T4 antibody, an anti-5T4 ADC or a pharmaceutical composition as described hereinabove with a therapeutic antibody, a chemotherapeutic agent, and/or an ADC against a cancer-related target other than the 5T4 antigen for the treatment of human solid tumours and haematological malignancies as described hereinabove.

In one embodiment of the present invention, particularly in case of an anti-5T4 ADC comprising a duocarmycin derivative linker drug, the therapeutic antibody is bevacizumab, cetuximab, nivolumab, or ramucirumab and the chemotherapeutic agent is an alkylating agent, particularly cyclophosphamide, ifosfamide or a triazine, particularly temozolomide, or a platinum drug, more particularly cisplatin or carboplatin, an anti-metabolite, particularly gemcitabine or pemetrexed, a topoisomerease II inhibitor, particularly etoposide, a mitotic inhibitor, particularly a taxane, more particularly paclitaxel or docetaxel, or a vinca alkaloid, more particularly vinblastine or vinorelbine, or a signalling cascade inhibitor, particularly a tyrosine kinase inhibitor, more particularly imatinib, erlotinib, ceritinib, crizotinib or afatinib.

In a further embodiment of the present invention, particularly in case of an anti-5T4 ADC comprising a duocarmycin derivative linker drug, the therapeutic antibody is bevacizumab and the chemotherapeutic agent is an alkylating agent, particularly a nitrogen mustard, particularly ifosfamide or cyclophosphamide, a platinum drug, particularly cisplatin or carboplatin, or a triazine, particularly temozolomide, an anti-tumour antibiotic, particularly doxorubicin, an anti-metabolite, particularly gemcitabine, a topoisomerease I or II inhibitor, particularly topotecan, irinotecan or etoposide, or a mitotic inhibitor, particularly a taxane, more particularly paclitaxel or docetaxel, or a vinca alkaloid, more particularly vincristine or vinorelbine.

In yet a further embodiment of the present invention, particularly in case of an anti-5T4 ADC comprising a duocarmycin derivative linker drug, the therapeutic antibody is amatuximab and the chemotherapeutic agent is an alkylating agent, particularly a platinum drug, more particularly cisplatin or carboplatin, an anti-metabolite, particularly gemcitabine or pemetrexed, or a mitotic inhibitor, particularly a vinca alkaloid, more particularly vinorelbine.

A therapeutically effective amount of the anti-5T4 antibody or ADC in accordance with the present invention lies in the range of about 0.01 to about 15 mg/kg body weight, particularly in the range of about 0.1 to about 10 mg/kg body weight, more particularly in the range of about 0.3 to about 10 mg/kg body weight. This latter range corresponds roughly to a flat dose in the range of 20 to 800 mg of the antibody or ADC. The compound of the present invention may be administered weekly, bi-weekly, three-weekly, monthly or six-weekly. Suitable treatment regimens are depending upon the severity of the disease, the age of the patient, the compound being administered, and such other factors as would be considered by the treating physician.

EXAMPLES

Immunization Protocol and Selection

Rabbits were repeatedly immunized with a mixture of hu 5T4/cyno5T4 protein (2 rabbits) and MDA-MB-468 cells (2 rabbits). About 20 ml blood was collected at different time points. Single B-cells were deposited into single wells of microtiter plates. These B-cells were cultivated for several days in the presence of conditioned medium and feeder cells. During this time they produced and released monoclonal antibodies into the cultivation medium (B-cell supernatants). The supernatants of these single B-cells were analyzed for IgG production, subsequently specific binding of the hu and cyno 5T4 antigen and binding to 5T4 expressing MDA-MB-468 cells was determined. 160 B-cell supernatants were selected and sequenced, as these antibodies bound to both human and cyno 5T4 antigen as well as to the MDA-MB-468 cells. 131 unique variable regions of antibody heavy and light chains were obtained, gene synthesized and cloned on human immunoglobulin constant parts of the IgG1 subclass. HEK 293 cells were transiently transfected with the immunoglobulin sequence containing plasmids using an automated procedure on a Tecan Freedom Evo platform. Immunoglobulins were purified from the cell supernatant using affinity purification (Protein A) on a Dionex Ultimate 3000 HPLC system with a plate autosampler. 4 samples with very low productivity were excluded, resulting in a total number of 127 antibodies for retesting. Antibodies were selected based upon their specific binding of the human and cyno 5T4 antigen and for binding to human 5T4 expressing MDA-MB-468 cells.

Binding to hu and cyno 5T4 antigen was determined by the following procedure. Hu or cyno 5T4 antigen was coated on a 384-format microtiter plate. A reference antibody, B-cell supernatants or a recombinantly produced antibody was added and the binding was detected via an anti-rabbit or human-POD antibody.

For binding to MDA-MB-468 cells, the cells were seeded on black cell culture microtiter plates (Corning). Specific antibodies originating from B-cell supernatants or the reference antibodies were allowed to interact with the cells. Binding was detected using an Alexa Fluor 488-labeled antibody. The fluorescence was read using a CellInsight (Thermo Fischer) device.

17 antibodies were selected and affinity to 5T4 antigen was measured using MDA-MB-468 cells, PA-1 cells and Chinese Hamster Ovary (CHO) mammalian cells expressing human or cyno 5T4 antigen (Table 2). In the current application the utilized CHO cells are referred to as CHOZN as these CHO cells expressing human or cyno 5T4 antigen were obtained using the CHOZN® Platform of Sigma-Aldrich. CHOZN cells (SAFC) were transiently transfected, using an Amaxa nucleofector device (Lonza) according to the manufacturer's instructions. Standard, commercially available mammalian expression vectors (SAFC, Life Technologies) were used, which contained the full length human and cyno 5T4 antigen coding sequence (according to accession number NP_006661.1 and Q4R8Y9 respectively), preceded by a human CMV promoter. Transiently transfected CHOZN cells were cultured according the manufacturer's instructions, before being used in antibody binding studies. The 17 selected antibodies are characterised by the amino acid sequences according to the following table (Table 1).

TABLE 1

Chimeric anti-5T4 monoclonal antibodies

| Antibody | HCVR | LCVR |
| --- | --- | --- |
| 789 | SEQ ID NO: 1 | SEQ ID NO: 2 |
| 811 | SEQ ID NO: 3 | SEQ ID NO: 4 |
| 825 | SEQ ID NO: 5 | SEQ ID NO: 6 |
| 828 | SEQ ID NO: 7 | SEQ ID NO: 8 |
| 829 | SEQ ID NO: 9 | SEQ ID NO: 10 |
| 833 | SEQ ID NO: 11 | SEQ ID NO: 12 |
| 834 | SEQ ID NO: 13 | SEQ ID NO: 14 |
| 835 | SEQ ID NO: 15 | SEQ ID NO: 16 |
| 841 | SEQ ID NO: 17 | SEQ ID NO: 18 |
| 843 | SEQ ID NO: 19 | SEQ ID NO: 20 |
| 845 | SEQ ID NO: 21 | SEQ ID NO: 22 |
| 847 | SEQ ID NO: 23 | SEQ ID NO: 24 |
| 848 | SEQ ID NO: 25 | SEQ ID NO: 26 |
| 849 | SEQ ID NO: 27 | SEQ ID NO: 28 |
| 868 | SEQ ID NO: 29 | SEQ ID NO: 30 |
| 899 | SEQ ID NO: 31 | SEQ ID NO: 32 |
| 908 | SEQ ID NO: 33 | SEQ ID NO: 34 |

In Vitro Affinity Protocol

MDA-MB-468 cells, PA-1 cells or CHOZN cells expressing human or cyno 5T4 antigen (100,000 cells/well in a 96-well plate) were washed three times with ice-cold FACS buffer (1×PBS (Lonza) containing 0.2% v/w BSA (Sigma-Aldrich, St. Louis, Mo.)) and 0.02% v/w $NaN_3$ (Sigma-Aldrich), followed by the addition of a concentration range of each primary mAb (50 μl/well) diluted in ice-cold FACS buffer. After an incubation of 30 minutes at 4° C., cells were washed three times with ice-cold FACS buffer and 50 μl/well secondary mAb (AffiniPure F(ab')$_2$ fragment Goat-anti-human IgG-APC, 1:6,000 dilution, Jackson Immuno Research) was added. After 30 minutes at 4° C., cells were washed twice and resuspended in 150 μl FACS buffer. Fluorescence intensities were determined by flow cytometry (BD FACS-Verse, Franklin Lakes, N.J.) and indicated as the median fluorescence intensity (MFI). Curves were fitted by nonlinear regression using the sigmoidal dose-response equation with variable slope (four parameters) in GraphPad Prism (version 5.01/6.01 for Windows, GraphPad, San Diego, Calif.). $EC_{50}$ values were calculated as the concentration in μg/ml that gives a response half way between bottom and top of the curve, when using a 4 parameter logistic fit.

The affinity of the chimeric antibodies measured on human 5T4 antigen (hu 5T4)-expressing MDA-MB-468 cells ranges from an $EC_{50}$ of 0.040 μg/ml to 0.730 μg/ml, comparable to the $EC_{50}$ value of H8, which is 0.19 μg/ml. However, the A1 antibody exhibits binding to hu 5T4 with a lower affinity (the $EC_{50}$ value is 4.72 μg/ml) as measured on MDA-MB-468 cells. The affinity of the chimeric antibodies for hu 5T4 was also measured on PA-1 cells and on CHOZN cells expressing hu 5T4. The $EC_{50}$ values of the chimeric antibodies were again in the same range as the $EC_{50}$ values of H8, whereas A1 showed at least a 3-fold lower binding affinity for hu 5T4 (Table 2). The $EC_{50}$ values of A3 on the three cell types expressing hu 5T4 were lower than the $EC_{50}$ values of the chimeric antibodies on the corresponding cell types.

The chimeric anti-5T4 antibodies have similar affinity for hu 5T4 and for cyno 5T4 when measured using CHOZN expressing hu 5T4 or CHOZN cells expressing cyno 5T4 as is shown in Table 2. Compared to the binding of H8 to cyno 5T4, the binding shows a 32-fold improvement for most chimeric antibodies, except for 846 (10-fold) and 828 (7-fold).

TABLE 2

Affinity of chimeric mAbs measured on hu 5T4- and cyno 5T4 expressing cells

| mAb | Affinity (hu 5T4) | | | Affinity (cyno 5T4) |
|---|---|---|---|---|
| | MDA-MB-468 $EC_{50}$ (μg/ml) | PA-1 $EC_{50}$ (μg/ml) | CHOZN $EC_{50}$ (μg/ml) | CHOZN $EC_{50}$ (μg/ml) |
| 833 | 0.04 | 0.02 | 0.14 | 0.08 |
| 825 | 0.07 | 0.03 | 0.13 | 0.14 |
| 843 | 0.08 | 0.04 | 0.21 | 0.21 |
| 835 | 0.09 | 0.08 | 0.17 | 0.18 |
| 828 | 0.10 | 0.10 | 0.19 | 0.82 |
| 789 | 0.10 | 0.03 | 0.27 | 0.15 |
| 848 | 0.09 | 0.05 | 0.17 | 0.12 |
| 868 | 0.14 | 0.04 | 0.22 | 0.17 |
| 899 | 0.09 | 0.05 | 0.17 | 0.18 |
| 841 | 0.10 | 0.02 | 0.24 | 0.14 |
| 845 | 0.11 | 0.05 | 0.20 | 0.17 |
| 834 | 0.13 | 0.05 | 0.19 | 0.13 |
| 829 | 0.17 | 0.07 | 0.24 | 0.22 |
| 847 | 0.20 | 0.22 | 0.22 | 0.20 |
| 908 | 0.21 | 0.04 | 0.23 | 0.24 |
| 846 | 0.42 | 0.33 | 0.57 | 1.11 |
| 811 | 0.73 | 0.40 | 0.34 | 0.25 |
| Reference mAb | | | | |
| H8 | 0.19 | 0.07 | 0.21 | 8.11 |
| A1 | 4.72 | 1.34 | 3.00 | 3.23 |
| A3 | 0.99 | 0.62 | 0.82 | 0.57 |

Humanization

Humanized antibodies were prepared by CDR grafting as described below.

The CDRs of the clones 789, 825 and 833 were identified using the CDR-definitions from the numbering system IMGT (LEFRANC, MP, The IMGT unique numbering for immunoglobulins, T cell receptors and Ig-like domains. The Immunologist, 7 (1999), pp. 132-136) and Kabat.

Online public databases of human IgG sequences were searched using the rabbit VH domain using BLAST search algorithms, and candidate human variable domains were selected from the top 200 BLAST results. Five candidates were selected based on criteria such as framework homology, maintaining key framework residues, canonical loop structure and immunogenicity. The same procedure was repeated for the VL domain of the antibody. All humanized VH variants were combined with all humanized VL variants resulting in 25 humanized variants for each antibody.

The humanized variants comprising a HC-41C mutation were synthesized according to the procedure below and their affinity for human and cyno 5T4 was measured using CHOZN cells expressing either human or cyno 5T4. 11 variants were selected for further evaluation.

Transient Expression of Antibodies a) Preparation of cDNA Constructs and Expression Vectors The HCVR of the mouse A1 amino acid sequence from U.S. Pat. No. 8,044,178, SEQ ID NO:2, positions 20-138, the HCVR of the mouse A3 amino acid sequence from U.S. Pat. No. 8,044,178, SEQ ID NO:10, positions 20-141, and the HCVR of H8 humanized variant 1 amino acid sequence from SEQ ID NO:52 were each joined at the N-terminus to a HAVT20 leader sequence (SEQ ID NO:54), and at the C-terminus to the constant domain of a human IgG1 HC according to SEQ ID NO:55. The resulting chimeric amino acid sequences were back-translated into a cDNA sequence codon-optimized for expression in human cells (*Homo sapiens*).

Similarly, the chimeric cDNA sequence for the LC of the construct was obtained by joining the sequences of a suitable secretion signal (also the HAVT20 leader sequence), the LCVR of the mouse A1 amino acid sequence from U.S. Pat. No. 8,044,178, SEQ ID NO:4, positions 21-127, the LCVR of the mouse A3 amino acid sequence from U.S. Pat. No. 8,044,178, SEQ ID NO:12, positions 21-127, or the LCVR of the H8 humanized variant 1 amino acid sequence SEQ ID NO:53, and a human IgG κ light chain constant region (SEQ ID NO:56), and back-translating the obtained amino acid sequences into a cDNA sequence codon-optimized for expression in human cells (*Homo sapiens*).

The cDNA sequences for the LC and HC of the humanized variants with the HC-41C mutation were obtained using a similar procedure, however, in this case the HC and LC sequences were joined at the N terminus to rabbit leader sequences (SEQ ID NO:57 and 58, respectively), and at the C-terminus to the constant domain of the human IgG1 HC according to SEQ ID NO:55. The sequences according to the following table were used, having a cysteine at position 41 of the HCVR according to Kabat numbering (Table 3).

TABLE 3

HCVR and LCVR of HC-41C humanized variants

| Humanized variant | HCVR | LCVR |
|---|---|---|
| 789a | SEQ ID NO: 35 | SEQ ID NO: 45 |
| 789b | SEQ ID NO: 36 | SEQ ID NO: 45 |
| 789c | SEQ ID NO: 37 | SEQ ID NO: 44 |
| 789d | SEQ ID NO: 37 | SEQ ID NO: 46 |
| 833a | SEQ ID NO: 61 | SEQ ID NO: 51 |
| 833b | SEQ ID NO: 62 | SEQ ID NO: 51 |
| 833c | SEQ ID NO: 63 | SEQ ID NO: 49 |
| 833d | SEQ ID NO: 64 | SEQ ID NO: 50 |
| 825a | SEQ ID NO: 59 | SEQ ID NO: 47 |
| 825b | SEQ ID NO: 60 | SEQ ID NO: 47 |
| 825c | SEQ ID NO: 60 | SEQ ID NO: 48 | b) Vector Construction and Cloning Strategy

For expression of the antibody chains a derivative of the commercially available (Thermo Fisher) mammalian expression vector pcDNA3.3 was used, which contains a CMV:BGHpA expression cassette. This vector was slightly adapted by changing the multiple cloning site downstream of the CMV promoter to contain AscI and NheI restriction sites, giving rise to expression vector 0080pcDNA3.3-SYN.

The cDNAs for the HC and the LC of the construct were ligated directly into the 0080pcDNA3.3-SYN vector, using AscI and NheI restriction sites. The final vectors containing either the HC or the LC expression cassette (CMV:HC:BGHpA and CMV:LC-BGHpA, respectively) were transferred to and expanded in *E. coli* NEB 5-alpha cells. Large-scale production of the final expression vectors for transfection was performed using Maxi- or Megaprep kits (Qiagen).

c) Transient Expression in Mammalian Cells

Commercially available Expi293F cells (Thermo Fisher) were transfected with the expression vectors using the ExpiFectamine transfection agent according to the manufacturer's instructions as follows: 75×10$^7$ cells were seeded in 300 mL FortiCHO medium, 300 μg of the expression vector was combined with 800 μl of ExpiFectamine transfection agent and added to the cells. One day after transfection, 1.5 ml Enhancer 1 and 15 ml Enhancer 2 were added to the culture. Six days post transfection, the cell culture supernatant was harvested by centrifugation at 4,000 g for 15 minutes and filtering the clarified harvest over PES bottle filters/MF 75 filters (Nalgene).

Affinity Measurements Using a Cell Based Assay

The humanized anti-5T4 antibodies have similar affinity for hu 5T4 and cyno 5T4 as measured on CHOZN cells expressing either hu 5T4 or cyno 5T4, except for the 825a, 825b and 825c humanized anti-5T4 antibodies, which show 2- to 3-fold lower binding to cyno 5T4 as compared to hu 5T4 (Table 4). Compared to the binding of H8 to cyno 5T4, the binding is 4- to 17-fold improved for the humanized anti-5T4 antibodies. Compared to A1, the binding is similarly improved. The affinity of the humanized anti-5T4 antibodies for hu 5T4 expressing CHOZN cells is comparable to H8.

TABLE 4

The affinity of humanized mAbs with HC-41C mutation and one chimeric mAb with HC-41C mutation measured on hu 5T4- and cyno 5T4-expressing CHOZN cells

| | CHOZN - hu 5T4 | | CHOZN - cyno 5T4 | |
|---|---|---|---|---|
| mAb | Avg EC$_{50}$ (μg/ml) | 95% CI[1] (μg/ml) | Avg EC$_{50}$ (μg/ml) | 95% CI[1] (μg/ml) |
| 789a | 0.20 | 0.14 to 0.28 | 0.33 | 0.24 to 0.48 |
| 789b | 0.15 | 0.10 to 0.20 | 0.24 | 0.16 to 0.30 |
| 789c | 0.20 | 0.11 to 0.29 | 0.21 | 0.16 to 0.26 |
| 789d | 0.12 | 0.08 to 0.18 | 0.15 | 0.08 to 0.27 |
| 833a | 0.22 | 0.11 to 0.30 | 0.12 | 0.084 to 0.17 |
| 833b | 0.15 | 0.08 to 0.24 | 0.18 | 0.12 to 0.26 |
| 833c | 0.18 | 0.11 to 0.26 | 0.17 | 0.12 to 0.20 |
| 833d | 0.18 | 0.11 to 0.25 | 0.16 | 0.11 to 0.23 |
| 825a | 0.15 | 0.09 to 0.21 | 0.53 | 0.33 to 0.80 |
| 825b | 0.16 | 0.11 to 0.23 | 0.46 | 0.30 to 0.58 |
| 825c | 0.21 | 0.13 to 0.31 | 0.42 | 0.34 to 0.49 |
| chimeric 899 | 0.14 | 0.08 to 0.26 | 0.18 | 0.11 to 0.27 |
| Reference mAbs | | | | |
| H8 | 0.22 | 0.15 to 0.32 | 1.99 | 1.19 to 2.52 |
| A1 | 4.42 | 0.53 to 19.19 | 1.58 | 1.09 to 2.27 |

[1]95% CI is 95% confidence interval

General Site-Specific Conjugation Protocol

To a solution of cysteine engineered anti-5T4 antibody (5-10 mg/ml in 4.2 mM histidine, 50 mM trehalose, pH 6) EDTA (25 mM in water, 4% v/v) was added. The pH was adjusted to ~7.4 using TRIS (1 M in water, pH 8) after which TCEP (10 mM in water, 20 equivalents) was added and the resulting mixture was incubated at room temperature for 1-3 hrs. The excess TCEP was removed by either a PD-10 desalting column or a Vivaspin centrifugal concentrator (30 kDa cut-off, PES) using 4.2 mM histidine, 50 mM trehalose, pH 6. The pH of the resulting antibody solution was raised to ~7.4 using TRIS (1 M in water, pH 8) after which dehydroascorbic acid (10 mM in water, 20 equivalents) was added and the resulting mixture was incubated at room temperature for 1-2 hrs. DMA was added followed by a solution of linker drug (10 mM in DMA). The final concentration of DMA was 5-10%. The resulting mixture was incubated at room temperature in the absence of light for 1-16 hrs. In order to remove the excess of linker drug, activated charcoal was added and the mixture was incubated at room temperature for 1 hr. The coal was removed using a 0.2 μm PES filter and the resulting ADC was formulated in 4.2 mM histidine, 50 mM trehalose, pH 6 using a Vivaspin centrifugal concentrator (30 kDa cut-off, PES). Finally, the ADC solution was sterile filtered using a 0.22 μm PES filter.

General (Random) Conjugation Protocol for Conjugation Via Partially Reduced Native Interchain Disulfide Bond Cysteines (Wild-Type or wt Conjugation)

To a solution of anti-5T4 antibody (5-10 mg/ml in 4.2 mM histidine, 50 mM trehalose, pH 6) EDTA (25 mM in water, 4% v/v) was added. The pH was adjusted to ~7.4 using TRIS (1 M in water, pH 8) after which TCEP (10 mM in water, 1-3 equivalents depending on the antibody and the desired DAR) was added and the resulting mixture was incubated at room temperature for 1-3 hrs. DMA was added followed by a solution of linker drug (10 mM in DMA). The final concentration of DMA was 5-10%. The resulting mixture was incubated at room temperature in the absence of light for 1-16 hrs. In order to remove the excess of linker drug, activated charcoal was added and the mixture was incubated at room temperature for 1 hr. The coal was removed using a 0.2 μm PES filter and the resulting ADC was formulated in 4.2 mM histidine, 50 mM trehalose, pH 6 using a Vivaspin centrifugal concentrator (30 kDa cut-off, PES). Finally, the ADC solution was sterile filtered using a 0.22 μm PES filter.

Using the above general procedures, cysteine engineered and wild-type ADCs based on vc-seco-DUBA (SYD980; i.e., compound 18b, n=1 in Example 10 on page 209 of WO2011/133039), were synthesized and characterized using analytical Hydrophobic Interaction Chromatography (HIC), Size Exclusion Chromatography (SEC), Shielded Hydrophobic Phase Chromatography (SHPC), RP-HPLC and LAL endotoxin-testing.

For analytical HIC, 5-10 μL of sample (1 mg/ml) was injected onto a TSKgel Butyl-NPR column (4.6 mm ID×3.5 cm L, Tosoh Bioscience, cat. nr. 14947). The elution method consisted of a linear gradient from 100% Buffer A (25 mM sodium phosphate, 1.5 M ammonium sulphate, pH 6.95) to 100% of Buffer B (25 mM sodium phosphate, pH 6.95, 20% isopropanol) at 0.4 ml/min over 20 minutes. A Waters Acquity H-Class UPLC system equipped with PDA-detector and Empower software was used. Absorbance was measured at 214 nm and the retention time of ADCs was determined. As made apparent by analytical HIC, there were differences in the retention times (RTs) for the DAR2 species of the different cysteine engineered ADCs. As well, the RT of the DAR2 species of most of the engineered ADCs was lower than the RT of the wt H8 conjugate (Table 5) and the increase in retention time ($RT_{DAR2}$-$RT_{DAR0}$) upon conjugation of two linker drugs is lower for the HC-41C engineered humanized ADCs compared to the increase for the wt H8-vc-seco-DUBA. All the engineered humanized ADCs have a $RT_{DAR2}$-$RT_{DAR0}$ value of between 2.1-3.1, which is lower than the $RT_{DAR2}$-$RT_{DAR0}$ value of wt H8-vc-seco-DUBA of 3.5, indicating that the engineered humanized ADCs exhibit decreased hydrophobicity.

TABLE 5

The hydrophobicity of vc-seco-DUBA ADCs by analytical HIC

| ADC | DAR | $RT_{DAR2}$ | $RT_{DAR0}$ | $RT_{DAR2}$-$RT_{DAR0}$ |
|---|---|---|---|---|
| H8-wt[1] | 2.0 | 9.9 | 6.4 | 3.5 |
| 789a | 1.8 | 9.4 | 6.3 | 3.1 |
| 789b | 1.7 | 9.1 | 6.4 | 2.7 |
| 789c | 1.7 | 9.1 | 6.3 | 2.8 |
| 789d | 1.7 | 9.2 | 6.4 | 2.8 |
| 833a | 1.7 | 9.4 | 6.9 | 2.5 |
| 833b | 1.7 | 9.5 | 6.9 | 2.6 |
| 833c | 1.7 | 9.0 | 6.9 | 2.1 |
| 833d | 1.5 | 9.9 | 7.1 | 2.8 |
| 825a | 1.7 | 8.5 | 6.4 | 2.1 |
| 825b | 1.7 | 8.6 | 6.4 | 2.2 |
| 825c | 1.7 | 8.2 | 6.0 | 2.2 |
| 899 chimeric | 0.9 | 10.3 | 6.5 | 3.8 |

[1]Random (non-site specific) attachment

In Vitro Cytotoxicity

Figure 1B:
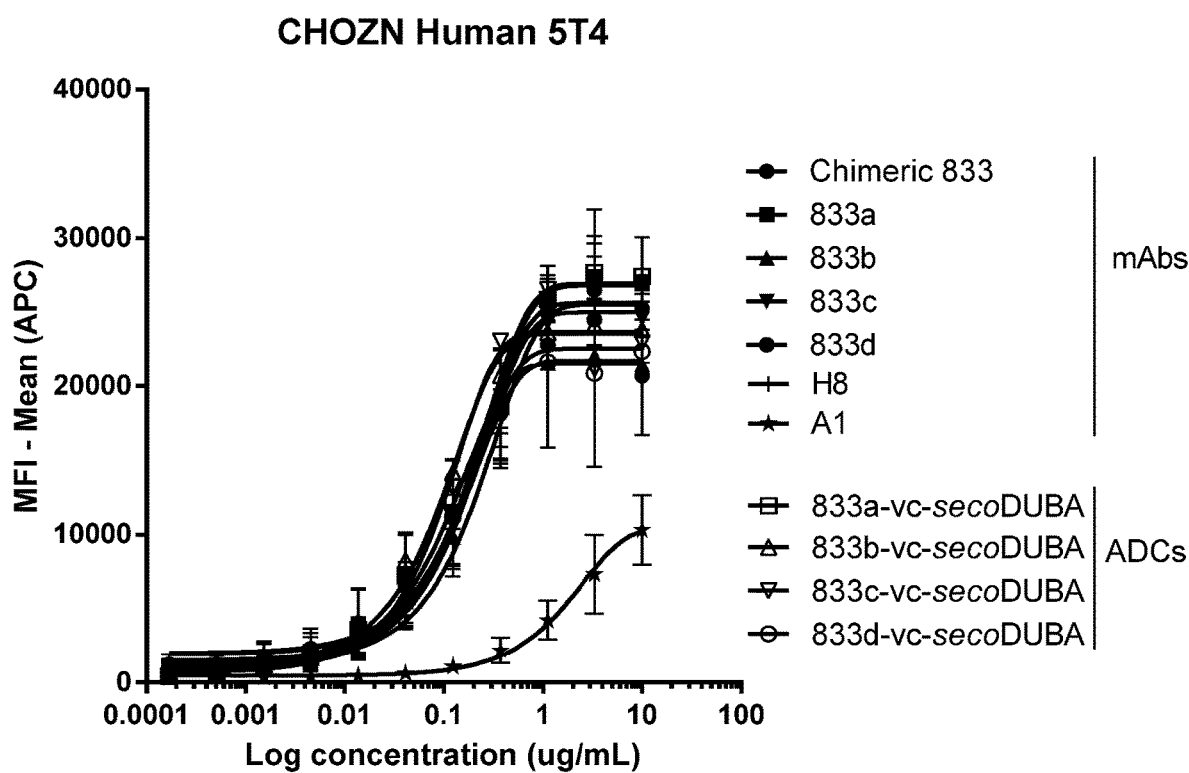
Figure 1C:
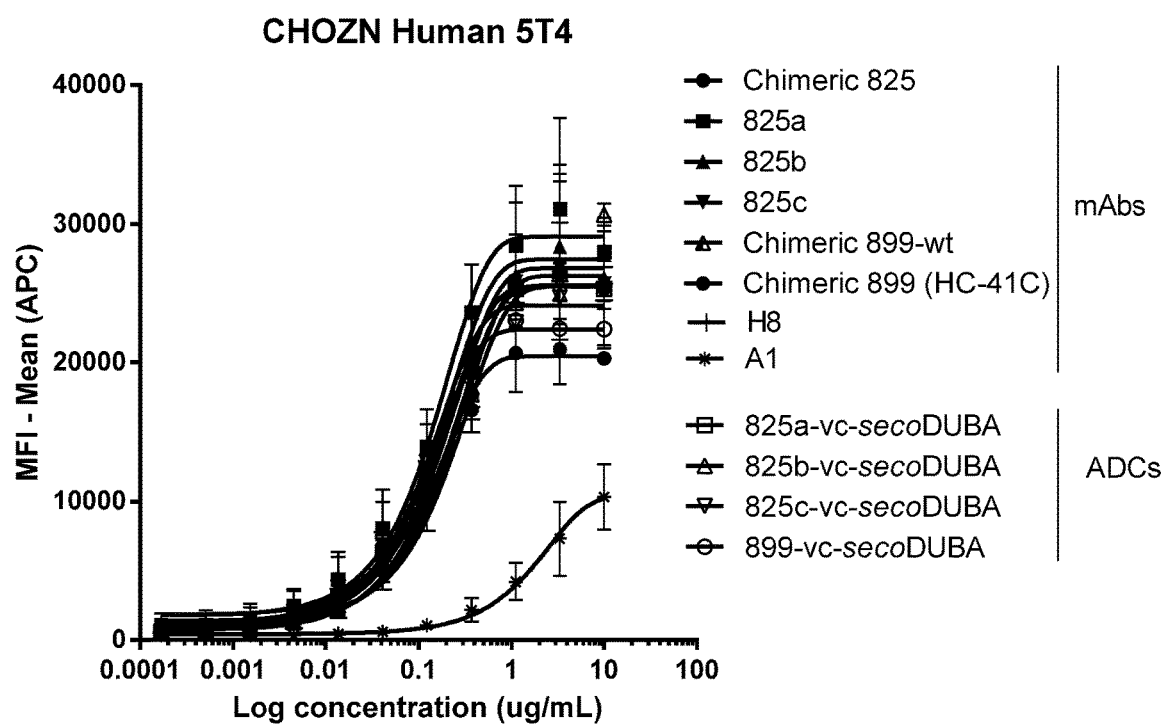
Figure 2A:
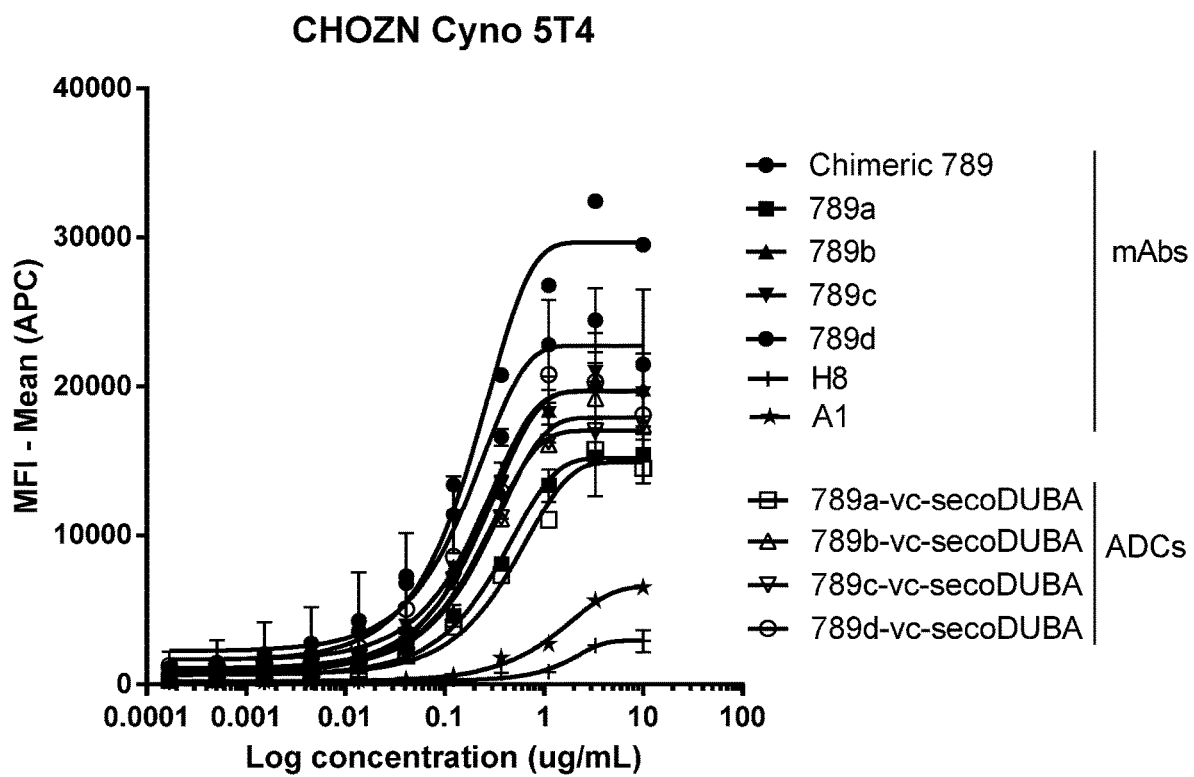
FIG. 2 shows the binding of chimeric mAbs, humanized mAbs with HC-41C mutation and corresponding anti-5T4 ADCs to cyno 5T4-expressing CHO cells (CHOZN) versus that of H8 and A1 (FIG. 2A clone 789, FIG. 2B clone 833, FIG. 2C clone 825).
Figure 2B:
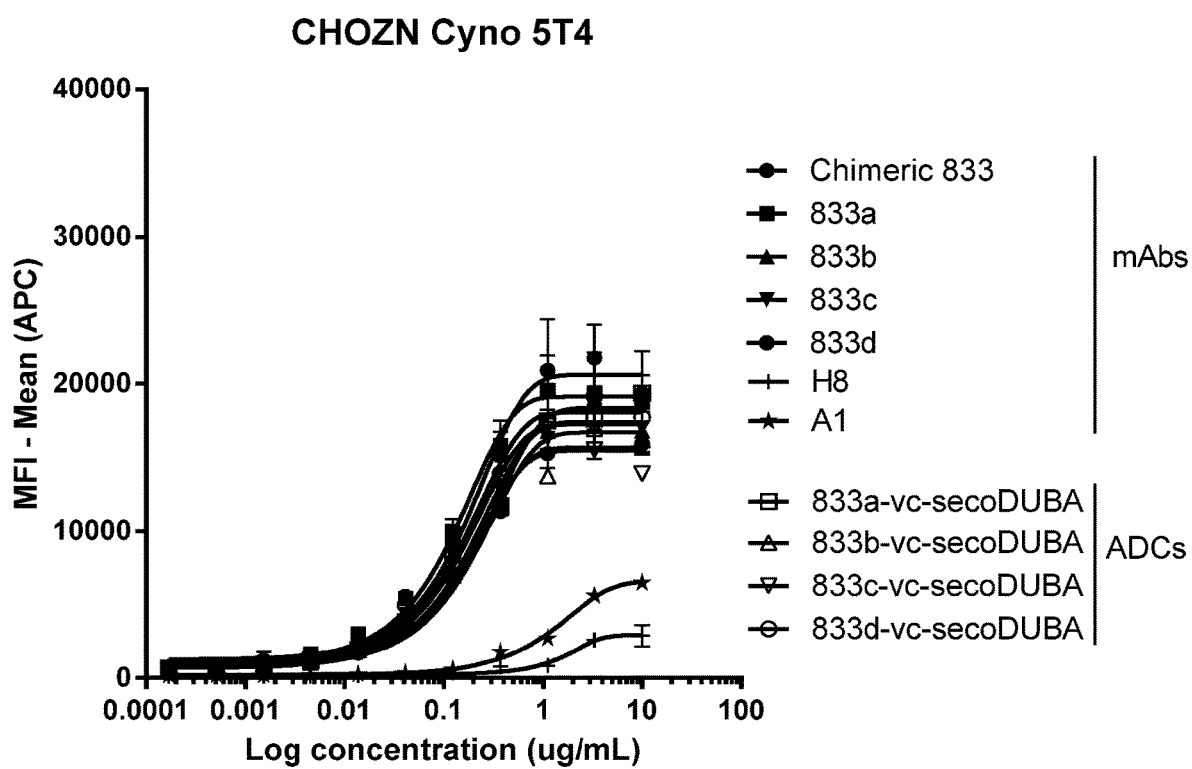
Figure 2C:
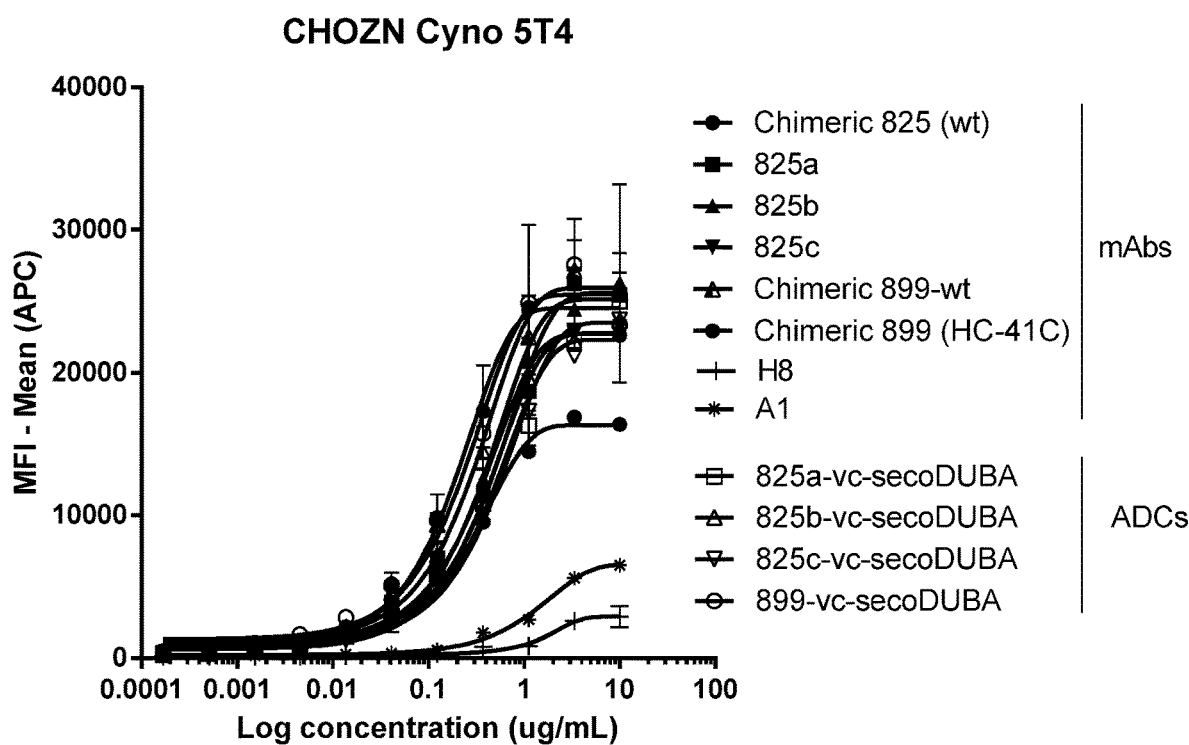

The antigen binding affinities of the (site-specific) anti-5T4 ADCs were unaffected by the attached duocarmycin derivative linker drug as measured on CHOZN cells expressing either hu 5T4 or cyno 5T4 (FIGS. 1 and 2). As expected, the non-binding control ADC (rituximab-vc-seco-DUBA) had an effect on the growth of the 5T4-expressing tumour cells only at high concentrations. All humanized anti-5T4 ADCs were inactive ($IC_{50}$>10 nM) on SK-MEL-30, a 5T4-negative human tumour cell line (about 400 5T4 antigen binding sites per cell).

The potencies of the engineered humanized anti-5T4 ADCs were comparable to the potency of the conventionally conjugated H8-wt ADC on hu 5T4-expressing MDA-MB-468 cells and PA-1 cells (Table 6). However, the 833-ADC series were unable to decrease the PA-1 cell viability completely (efficacy 65 to 72%). Furthermore, the engineered humanized anti-5T4 ADCs were over 2.5 times more potent than the A3-vc-seco-DUBA and more than 14 times more potent than the A1-vc-seco-DUBA.

TABLE 6

In vitro cytotoxicity of the vc-seco-DUBA ADCs in human tumour cells expressing 5T4

| HC-41C | MDA-MB-468 | | | PA-1 | | |
|---|---|---|---|---|---|---|
| | Avg $IC_{50}$ (nM) | Efficacy (%) | 95% CI[1] (nM) | Avg $IC_{50}$ (nM) | Efficacy (%) | 95% CI[1] (nM) |
| ADC | | | | | | |
| 789a | 0.16 | 99 | 0.18 to 0.22 | 0.13 | 96 | 0.09 to 0.16 |
| 789 b | 0.14 | 99 | 0.15 to 0.19 | 0.11 | 97 | 0.07 to 0.14 |
| 789 c | 0.14 | 99 | 0.15 to 0.20 | 0.11 | 91 | 0.07 to 0.13 |
| 789d | 0.10 | 99 | 0.10 to 0.14 | 0.08 | 89 | 0.05 to 0.10 |
| 833a | 0.11 | 99 | 0.13 to 0.17 | 0.13 | 67 | 0.07 to 0.18 |
| 833b | 0.10 | 99 | 0.12 to 0.15 | 0.13 | 72 | 0.06 to 0.20 |
| 833c | 0.13 | 98 | 0.15 to 0.21 | 0.13 | 66 | 0.07 to 0.17 |
| 833d | 0.12 | 99 | 0.11 to 0.14 | 0.18 | 65 | 0.08 to 0.26 |
| 825a | 0.14 | 99 | 0.15 to 0.19 | 0.11 | 95 | 0.08 to 0.13 |
| 825b | 0.14 | 99 | 0.15 to 0.18 | 0.12 | 97 | 0.08 to 0.13 |
| 825c | 0.12 | 99 | 0.15 to 0.18 | 0.09 | 97 | 0.06 to 0.10 |

TABLE 6-continued

In vitro cytotoxicity of the vc-seco-DUBA ADCs in human tumour cells expressing 5T4

| | MDA-MB-468 | | | PA-1 | | |
|---|---|---|---|---|---|---|
| HC-41C | Avg IC$_{50}$ (nM) | Efficacy (%) | 95% CI[1] (nM) | Avg IC$_{50}$ (nM) | Efficacy (%) | 95% CI[1] (nM) |
| Reference ADC | | | | | | |
| H8-vc-seco-DUBA | 0.11 | 99 | 0.10 to 0.12 | 0.09 | 93 | 0.04 to 0.09 |
| A1-vc-seco-DUBA | 2.25 | 95 | 1.95 to 2.59 | — | — | — |
| A3-vc-seco-DUBA | 0.45 | 97 | 0.40 to 0.51 | — | — | — |
| Rituximab-vc-seco-DUBA | 32.92 | 91 | 26.86 to 47.15 | 8.32 | N/A | N/A |
| Duocarmycin toxin | 0.05 | 99 | 0.04 to 0.04 | 0.14 | 99 | 0.10 to 0.16 |

[1]95% CI is 95% confidence interval
[2]N/A is not applicable

In Vivo Efficacy Study

The in vivo efficacy of anti-5T4 ADCs was evaluated in a BT474 (invasive ductal breast carcinoma from a 60-year old Caucasian female patient) cell-line xenograft model in B6;D2-Ces1c$^e$ Foxn1$^{nu}$/J mice. Immunohistochemical staining confirmed presence of hu 5T4 on the cellular membrane of the BT474 cell line.

Tumours were induced subcutaneously by injecting 2×10$^7$ BT-474 cells in 200 μL RPMI 1640 medium containing matrigel (50:50, v:v) into the right flank of 110 female Ces1c$^e$ nude mice, 24 to 72 hrs after a whole body irradiation with a γ-source (2 Gy, $^{60}$Co, BioMep, Dijon, France). When the tumours had reached a mean volume of 200-300 mm$^3$, the mice were dosed with a single injection of 3 mg/kg H8-, 833a-, 833b-, 833c-, 833d-, 825a- or 825c-vc-seco-DUBA ADC. Vehicle and the non-binding rituximab-vc-seco-DUBA ADC were used as controls. Mice having Ces1c activity in plasma were excluded from analysis.

Figure 3:
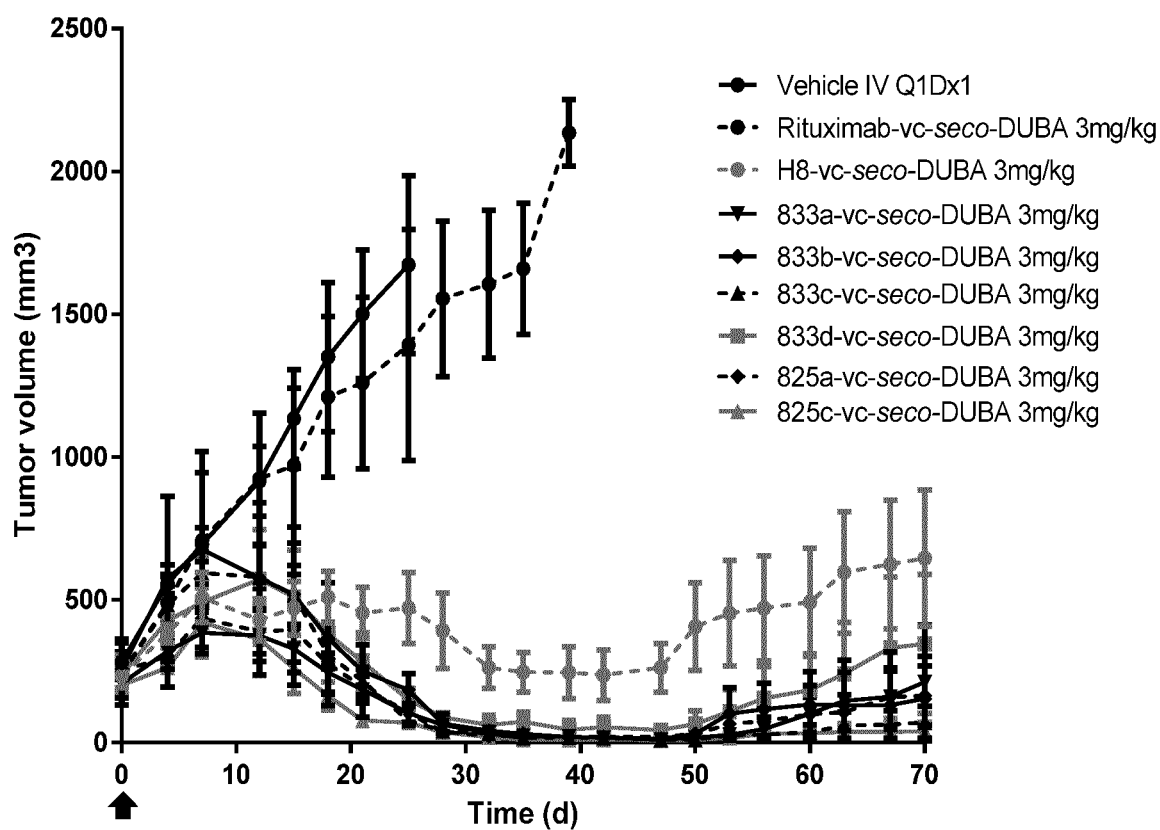
FIG. 3 shows the in vivo efficacy of the anti-5T4 ADCs 833a-, 833b-, 833c-, 833d-, 825a-, 825c-vc-seco-DUBA versus H8-vc-seco-DUBA and non-binding control rituximab-vc-seco-DUBA in the 5T4-positive BT474 cell line xenograft in immunodeficient mice.

All site-specifically conjugated anti-5T4 ADCs reduced the tumour volume more than the prior art H8-vc-seco-DUBA (FIG. 3), indicating improved in vivo efficacy.

In Vivo Pharmacokinetics

A pharmacokinetic study was performed with anti-5T4 ADCs in the B6(Cg)-Ces1c$^{tm1.1Loc}$/J mouse strain. These mice lack exon 5 of the Ces1c gene leading to the abolishment of the function of the enzyme. Mice were dosed with the anti-5T4 ADCs (3 mg/kg, i.v. in the tail vein) and plasma was collected at 0.25, 1, 6, 24, 48, 96, 168, 336, and 504 hrs post dosing. ELISA-based assays were used to quantify total antibody and conjugated antibody. The conjugated antibody assay captures ADC species that contain at least one linker drug. The results presented in Table 7 show that the site-specific ADCs are very stable, are cleared slower and have a longer half life than the prior art H8-vc-seco-DUBA ADC.

TABLE 7

Pharmacokinetics of anti-5T4 ADCs in Ces1c KO mice

| | Approximate t$_{1/2}$ (hrs) | C$_{max}$ (μg/mL) | AUC$_{last}$ (hrs*μg/mL) |
|---|---|---|---|
| Total antibody | | | |
| H8-vc-seco-DUBA | nd | nd | nd |
| 833a-vc-seco-DUBA | 247 | 50.3 | 6484 |
| 833b-vc-seco-DUBA | 388 | 46.6 | 8702 |
| 833c-vc-seco-DUBA | 459 | 64.7 | 13177 |
| 833d-vc-seco-DUBA | nd | nd | nd |
| 825a-vc-seco-DUBA | 582 | 47.7 | 12596 |
| 825c-vc-seco-DUBA | 2471 | 74.9 | 20901 |
| Conjugated antibody | | | |
| H8-vc-seco-DUBA | 113 | 54.5 | 3979 |
| 833a-vc-seco-DUBA | 172 | 61.0 | 4991 |
| 833b-vc-seco-DUBA | 255 | 56.3 | 8116 |
| 833c-vc-seco-DUBA | 327 | 52.5 | 8348 |
| 833d-vc-seco-DUBA | nd | nd | nd |
| 825a-vc-seco-DUBA | 398 | 67.7 | 11934 |
| 825c-vc-seco-DUBA | 1049 | 67.2 | 15558 | nd is not determined

Sequence listings with underlined CDR1, CDR2 and CDR3 amino acid sequences in HCVR and LCVR amino acid sequences SEQ ID NO: 1
(HCVR of clone/well 789 - rabbit)
  1 QSVEESGGRL VTPGTPLTLT CTASGFSLSS YWMSWVRQAP GKGLEWIGII

51 AGRGSTYYAS WAKGRCTISK TSTTVDLKIT SPTTEDTAAY FCARVSSIYY

101 TFNLWGQGTL VTVSS

SEQ ID NO: 2
(LCVR of clone/well 789 - rabbit)
  1 AQVLTQTPSS VSAAVGGTVT INCQSSQSVY SNNELSWYQQ KPGQPPKLLI

51 YYASTLASGV PSRFKGSGSG TQFTLTISGV QSDDAATYYC QGSYYSGSGW

101 YYAFGGGTEVVVK

```
                                               SEQ ID NO: 3
(HCVR of clone/well 811 - rabbit)
   1 QSVEESGGRL VTPGTSLTLT CTASGFSLST YAMIWVRQAP GKGLEWIGII

51 NSSGYTYYAN WAKGRFTISK TSTTVDLKIT SPTTEDTATY FCARGNAGIS

101 YDVSFNLWGQ GTLVTVSS

SEQ ID NO: 4
(LCVR of clone/well 811 - rabbit)
   1 AYDMTQTPAS VEAGVGGTVT INCQASESIS SWLAWYQQKP GQPPNLLIYE

51 ASKLASGVPS RFSGSGSGTE FTLTISGVES ADAATYYCQQ GWTSSNIDNA

101 FGGGTEVVVK

SEQ ID NO: 5
(HCVR of clone/well 825 - rabbit)
   1 QSVEESGGRL VTPGTPLTLT CTVSGIDLSS YGMGWVRQAP GKGLEYIGII

51 SRNSVTYYAT WAKGRFTISK TSTTVDLKMT SPTTEDTATY FCARRATYSG

101 ALGYFDIWGP GTLVTVSF

SEQ ID NO: 6
(LCVR of clone/well 825 - rabbit)
   1 GYDMTQTPAS VSAAVGGTVT INCQASENIY STLAWYQQKP GQPPKVLIYD

51 AFDLASGVPS RFKGSGSGTE YTLTISGVQS DDAATYYCQQ GYSGTNVDNA

104 FGGGTEVVVK

SEQ ID NO: 7
(HCVR of clone/well 828 - rabbit)
   1 QSVEESGGRL VTPGTPLTLT CTVSEIDLST YAMSWVRQAP GKGLEWIGII

51 SAGGSAYYAS WAKGRFTISR TSTTVDLKMT SLTTEDTATY FCARGAAYAG

101 YTYGFSFFDI WGPGTLVTVS L

SEQ ID NO: 8
(LCVR of clone/well 828 - rabbit)
   1 DIVMTQTPSS VSAAVGGTVT INCQASQNIY SNLAWYQQKP GQRPKLLIYG

51 ASNLESGVPS RFKGSGSGTE YTLTISDLES DDAATYYCQS IDYGNNYLGS

101 FGGGTEVVVK

SEQ ID NO: 9
(HCVR of clone/well 829 - rabbit)
   1 QSLEESGGRL VTPGTPLTLT CTASGFSLSS YDMSWVRQAP GKGLEYIGWI

51 NSDDGAYYAN WAKGRFTISR TSTTVDLKIT SPTTEDTATY FCARDAGSTY

101 LYGLDPWGPG TLVTVSS

SEQ ID NO: 10
(LCVR of clone/well 829 - rabbit)
   1 DVVMTQTPSS VSAGVGGTVT IKCQASQSIS SYLAWYQQKP GQRPKLLIYA

51 ASTLASGVSS RFKGSGSGTE YTLTINDLES ADAATYYCQC TYYGGTYNTF

101 GGGTEVVVK

SEQ ID NO: 11
(HCVR of clone/well 833 - rabbit)
   1 QSLEESGGGL VTPGGSLTLT CTGSGIDLSH YVVGWVRQAP GKGLEWIGII

51 YGSGRTYYAN WAKGRFTISK TSTTVDLRIA RPTAEDTATY FCARDASVSV

101 YYWGYFDLWG QGTLVTVSS

SEQ ID NO: 12
(LCVR of clone/well 833 - rabbit)
   1 AYDMTQTPVS VEVAVGGTVT IKCQASQSIG SELAWYQQKP GQPPKLLIYR

51 ASTLESGVPS RFSGSGSGTE FTLTISGVES ADAATYYCQQ GYTYSEIDNA

101 FGGGTEVVVK
```

-continued

```
                                                    SEQ ID NO: 13
(HCVR of clone/well 834 - rabbit)
  1 QSVEESGGRL VTPGTPLTLT CTVSGFSLST YSMSWVRQAP GKGLEWIGVI

51 SRGGSAYYAS WAKGRFTISK TSTTVDLKVT SPTTEDTATY FCARGAISSG

101 YYVYDGMDLW GPGTLVTVSS

SEQ ID NO: 14
(LCVR of clone/well 834 - rabbit)
  1 DIVMTQTPGS VEAAVGGTVT IKCQASESIS SYLAWYQQKP GQPPKFLIYS

51 ASTLASGVPS RFKGSGSGTE FTLTISDLES ADAATYYCQC TDYGSDYMGA

101 FGGGTGVVVK

SEQ ID NO: 15
(HCVR of clone/well 835 - rabbit)
  1 QSVEESGGRL VTPGTPLTLT CTVSGIDLSS GAMGWVRQAP GKGLEWIGLI

51 SSSPITYYAN WARGRFTISK TSTTVDLKIT SPTTADTATY FCARGYDDYG

101 EIWFNIWGPG TLVTVSL

SEQ ID NO: 16
(LCVR of clone/well 835 - rabbit)
  1 AIEMTQSPPS LSASVGETVR IRCLAGEDIY SSISWYQQKP GKPPTLLIYG

51 ASNLESGVPP RFSGSGSGTD YTLTIGGVQA EDAATYYCLG GWSYSSSLTF

101 GAGTKVEIK

SEQ ID NO: 17
(HCVR of clone/well 841 - rabbit)
  1 QSLEESGGRL VTPGTPLTLT CKASGFSLS TYWMSWVRQA PGKGLEWIGI

51 MLSYGNTVYA NWAKGRFTIS KTSSTTVDLK ITSPTTEDTA TYFCARGLYG

101 GYPNYGVYDL WGQGTLVTVS S

SEQ ID NO: 18
(LCVR of clone/well 841 - rabbit)
  1 DVVMTQTPAS VEAAVGGTVT IKCQASQSIS SYLSWYQQKP GQPPKLLIYA

51 ASNLASGVSS RFKGSRSGTE YTLTISDLES ADAATYYCQC TDYGSNYVGA

101 FGGGTEVVVK

SEQ ID NO: 19
(HCVR of clone/well 843 - rabbit)
  1 QSLEESGGRL VTPGTPLTLT CTASGFSLNN AYMNWVRQAP GKGLEWIGII

51 NTYGSTYFAT WAKGRFTFSK TSTTVDLKIT SPTTEDTATY FCARAYAPFS

101 TYSHYYGMDL WGPGTLVTVS S

SEQ ID NO: 20
(LCVR of clone/well 843 - rabbit)
  1 DVVMTQTPSS VSAAVGGTVT IKCQASESIG SWLSWYQQKP GQPPKLLIYE

51 ASKLTSGVPS RFKGSGSGTE YTLTISDLES ADAATYYCQY TDYGSNYLGT

101 FGGGTEVVVK

SEQ ID NO: 21
(HCVR of clone/well 845 - rabbit)
  1 QSLEESGGRL VTPGTPLTLT CTVSGIDLSS YTMNWVRQAP GKGLEWIGVI

51 TSHNTYYASW AKGRFTISKT STTVDLKITS PTTEDTATYF CARSNYGSTI

101 YYMGGMDPWG PGTLVTVSS

SEQ ID NO: 22
(LCVR of clone/well 845 - rabbit)
  1 DVVMTQTPAS VSAAVGGTVT INCQASQSIG SYLAWYQHQP GQPPKLLIYS

51 ASTLESGVSS RFEGSRSGTE YTLTISDLDS ADAATYYCQC TDYGASYLGA

101 FGGGTEVVVK
```

```
                                                         SEQ ID NO: 23
(HCVR of clone/well 847 - rabbit)
  1 QSVEESGGRL VTPGTPLTLT CTVSGFSLSS YDMSWVRQAP GKGLEYIGYI

51 NSDGSAYYAS WAKGRFTISK TSSTTVDLKI TSPTTEDTAT YFCARDAGST

101 YLYGMDPWGP GTLVTVSS

SEQ ID NO: 24
(LCVR of clone/well 847 - rabbit)
  1 DVVMTQTPAS VSEPVGGTVT INCQASQSIY SYLAWYQQKP GQRPKLLIYA

51 ASTLASGVSS RFKGSGSGTQ FTLTISDLES ADAATYYCQC TYYGGTFNTF

101 GGGTEVVVK

SEQ ID NO: 25
(HCVR of clone/well 848 - rabbit)
  1 QSVEESGGRL VTPGTPLTLT CTVSGFSLSS YTMSWVRQAP GKGLEWIGII

51 SSIGSIWYAS WAKGRFTISK TSTTVDLKMT SLTTEDTATY FCARDGTGSK

101 YYTWDRLDLW GQGTLVTVSS

SEQ ID NO: 26
(LCVR of clone/well 848 - rabbit)
  1 NIVMTQTPSP VSGAVGGTVT INCQASQSIY NELSWYQQKP GQPPKLLIYY

51 TSTLASGVSS RFKGSGSGTQ FTLTISGVES VDAATYYCQQ GYSSSDVDNVF

101 GGGTEVVVK

SEQ ID NO: 27
(HCVR of clone/well 849 - rabbit)
  1 QSVEESGGRL VTPGTPLTLT CTVSGFSLSR YDMSWVRQAP GKGLEYIGYI

51 NRDGSAYYAN WAKGRFTISK TSTTVDLKIT SPTTDDTATY FCARHAGSTY

101 LYGMDPWGPG TLVTVSS

SEQ ID NO: 28
(LCVR of clone/well 849 - rabbit)
  1 DVVMTQTPSS VSAAVGGTVT IKCQASQSIS NYLAWYQQKP GQPPKLLIYA

51 ASTLASGVSS RFKGSGSGTE FTLTISDLES ADAATYYCQC TYFGDTYNVF

101 GGGTEVVVK

SEQ ID NO: 29
(HCVR of clone/well 868 - rabbit)
  1 QSVEESGGRL VTPGTPLTLT CTASGFSLSD YTMGWVRQAP GKGLEWIGII

51 NGYGSTYYAN WAKGRFAISK TSTTVDLKIT SPATEDTATY FCARGDTGRT

101 YDMHFNLWGQ GTLVTVSS

SEQ ID NO: 30
(LCVR of clone/well 868 - rabbit)
  1 AYDMTQTPAS VSAAVGGTVT IKCQASESIR SWLAWYQQKP GQPPKLLIYS

51 ASTLASGVSS RFKGSGSGTQ FTLTIGDLES ADAATYYCQQ GYTSSNLDNA

101 FGGGTEVLVK

SEQ ID NO: 31
(HCVR of clone/well 899 - rabbit)
  1 QSVEESGGRL VTPGTPLTLT CTVSGFSLSS YTMSWVRQAP GKGLEYIGII

51 SSSDGTWYAN WVKGRFTISK TSTTVDLKMT SLTTEDTATY FCARDGTGNK

101 YYTWDRLDLW GQGTLVTVSS

SEQ ID NO: 32
(LCVR of clone/well 899 - rabbit)
  1 NIVMTQTPSP VSGAVGGTVT INCQASQSIY NELSWYQQKP GQPPKLLIYY

51 ASTLASGVSS RFKGSGSGTQ FTLTISGVES VDAATYYCQQ GYSSSNVDNV

101 FGGGTEVVVK
```

```
                                                          SEQ ID NO: 33
(HCVR of clone/well 908 - rabbit)
    1 QSVEESGGRL VTPGTPLTLT CTVSGFSLSN FAMSWVRQAP GKGLEWIGII

51 NGYGSIYYAT WAKGRFTISK TSTTVDLKIT SPTTEDTATY FCARGDAGRT

101 YNHYFNIWGP GTLVTVSL

SEQ ID NO: 34
(LCVR of clone/well 908 - rabbit)
    1 DVVMTQTPAS VEAAVGGTVT IKCQASQSIS SWLSWYQQKP GQRPKLLIYA

51 ASNLASGVPS RFKGSGSGTQ FTLTISDLES DDAATYYCQQ GYTSYNVDNA

101 FGGGTEVVVK
```

15

Humanized HCVR amino acid sequences with preferred
positions for cysteine mutation 40, 41 and 89 underlined

```
                                                          SEQ ID NO: 35
(HCVR 789 humanized version 1)
    1 EVKVEESGGG LVQPGGSLRL SCAASGFSLS SYWMSWVRQA PGKGLEWVSI

51 IAGRGSTYYA SWAKGRFTIS KDNSEGMVYL QMNSLRAEDT AVYYCARVSS

101 IYYTFNLWGQ GTTVTVSS

SEQ ID NO: 36
(HCVR 789 humanized version 2)
    1 EVQLLESGGS LVLPGGSLRL SCAASGFSLS SYWMSWVRQA PGKGLEWVSI

51 IAGRGSTYYA SWAKGRFTIS RDNSKNTLYM QMNSLRAEDT ALYFCARVSS

101 IYYTFNLWGQ GTLVTVSS

SEQ ID NO: 37
(HCVR 789 humanized version 3)
    1 QSVEESGGGL VQPGGSLRLS CAASGFSLSS YWMSWVRQAP GKGLEWIGII

51 AGRGSTYYAS WAKGRFTISR DNSKNTLYLQ MNSLRAEDTA VYYCARVSSI

101 YYTFNLWGQG TLVTVSS

SEQ ID NO: 38
(HCVR 825 humanized version 1)
    1 EVQLVESGGD LAQPGGSLRL SCAVSGIDLS SYGMGWVRQA PGKGLEWVSI

51 ISRNSVTYYA TWAKGRFTIS RDNSKNTVYL QMTSLRAEDT ALYFCARRAT

101 YSGALGYFDI WGQGTLVTVS S

SEQ ID NO: 39
(HCVR 825 humanized version 2)
    1 EVQLEESGGG LVKPGGSLRL SCAASGIDLS SYGMGWVRQA PGKGLEWVSI

51 ISRNSVTYYA TWAKGRFTIS RDNSKNTLYL QMNSLRAEDT AVYYCARRAT

101 YSGALGYFDI WGRGTLVTVS S

SEQ ID NO: 40
(HCVR 833 humanized version 1)
    1 EVQLVESGGG LIQPGGSLRL SCAASGIDLS HYVVGWVRQA PGKGLEWVSI

51 IYGSGRTYYA NWAKGRFTIS KDNSKNTLYV RMNSLRAEDT AVYYCARDAS

101 VSVYYWGYFD LWGQGTLVTV SS

SEQ ID NO: 41
(HCVR 833 humanized version 2)
    1 EVQLVESGGG LVQPGGSLRL SCAASGIDLS HYVVGWVRQA PGKGLEWVSI

51 IYGSGRTYYA NWAKGRFTIS RDNSKNTLFL RMNSLRVEDT AVYFCARDAS

101 VSVYYWGYFD LWGQGTLVTV SS
```

```
                                              SEQ ID NO: 42
(HCVR 833 humanized version 3)
   1 EVQLEESGGG LVKPGGSLRL SCAASGIDLS HYVVGWVRQA PGKGLEWVSI

51 IYGSGRTYYA NWAKGRFTIS RDNSKNTLYL QMNSLRAEDT AVYYCARDAS

101 VSVYYWGYFD LWGRGTLVTV SS

SEQ ID NO: 43
(HCVR region 833 humanized version 4)
   1 QSLEESGGGL VQPGGSLRLS CAASGIDLSH YVVGWVRQAP GKGLEWIGII

51 YGSGRTYYAN WAKGRFTISR HNSKNTLYLQ MNSLRAEDTA VYYCARDASV

101 SVYYWGYFDL WGQGTLVTV SS
```

Humanized LCVR amino acid sequences with preferred positions for cysteine mutation 40 and 41 underlined[15]

```
                                              SEQ ID NO: 44
(LCVR 789 humanized version 1)
   1 DIVMTQSPDS LAVSLGERAT INCQSSQSVY SNNELSWYQQ KPGQPPKLLI

51 YYASTLASGV PDRFSGSGSG TDFTLTISSL QAEDVAVYYC QGSYYSGSGW

101 YYAFGGGTKL EIK

SEQ ID NO: 45
(LCVR 789 humanized version 2)
   1 EIVLTQSPSS LSASVGDRVT ITCQSSQSVY SNNELSWYQQ KPGKAPKLLI

51 YYASTLASGV PSRFSGSGSG TDFTLTISSL QPEDFATYYC QGSYYSGSGW

101 YYAFGQGTKL EIK

SEQ ID NO: 46
(LCVR 789 humanized version 3)
   1 AQVLTQSPSS LSASVGDRVT ITCQSSQSVY SNNELSWYQQ KPGKAPKLLI

51 YYASTLASGV PSRFSGSGSG TDFTLTISSL QPEDFATYYC QGSYYSGSGW

101 YYAFGGGTKV EIK

SEQ ID NO: 47
(LCVR 825 humanized version 1)
   1 EIVMTQSPSS LSASVGDRVT ITCQASENIY STLAWYQQKP GKAPKLLIYD

51 AFDLASGVPS RFSGSGSGTD YTLTISSLQP EDFATYYCQQ GYSGTNVDNA

101 FGQGTKLEIK

SEQ ID NO: 48
(LCVR 825 humanized version 2)
   1 GYDMTQSPSS VSASVGDRVT ITCQASENIY STLAWYQQKP GKAPKLLIYD

51 AFDLASGVPS RFKGSGSGTE YTLTISSLQP EDFATYYCQQ GYSGTNVDNA

101 FGGGTKVEIK

SEQ ID NO: 49
(LCVR 833 humanized version 1)
   1 DIQMTQSPST LSASVGDRVT ITCQASQSIG SELAWYQQKP GKAPKLLIYR

51 ASTLESGVPS RFSGSGSGTE FTLTISSLQP DDFATYYCQQ GYTYSEIDNA

101 FGQGTKVEIK

SEQ ID NO: 50
(LCVR 833 humanized version 2)
   1 DIQMTQSPSS LSASVGDRVT ITCQASQSIG SELAWYQQKP GQAPKLLIYR

51 ASTLESGVPS RFSGSGSGTE FTFTISSLQP EDLATYYCQQ GYTYSEIDNA

101 FGQGTKLEIK
```

```
                                                   SEQ ID NO: 51
(LCVR 833 humanized version 3)
   1 AYDMTQSPSS VSASVGDRVT ITCQASQSIG SELAWYQQKP GKAPKLLIYR

51 ASTLESGVPS RFSGSGSGTD FTLTISSLQP EDFATYYCQQ GYTYSEIDNA

101 FGGGTKVEIK

SEQ ID NO: 52
(H8 HC)
   1 QVQLVQSGAE VKKPGASVKV SCKASGYSFT GYYMHWVKQS PGQGLEWIGR

51 INPNNGVTLY NQKFKDRVTM TRDTSISTAY MELSRLRSDD TAVYYCARST

101 MITNYVMDYW GQGTLVTVSS

SEQ ID NO: 53
(H8 LC)
   1 DIVMTQSPDS LAVSLGERAT INCKASQSVS NDVAWYQQKP GQSPKLLISY

51 TSSRYAGVPD RFSGSGSGTD FTLTISSLQA EDVAVYFCQQ DYNSPPTFGG

101 GTKLEIK

SEQ ID NO: 54
(HAVT20 leader sequence)
   1 MACPGFLWAL VISTCLEFSM A

SEQ ID NO: 55
(human IgG1 antibody HC constant region)
   1 ASTKGPSVFP LAPSSKSTSG GTAALGCLVK DYFPEPVTVS WNSGALTSGV

51 HTFPAVLQSS GLYSLSSVVT VPSSSLGTQT YICNVNHKPS NTKVDKKVEP

101 KSCDKTHTCP PCPAPELLGG PSVFLFPPKP KDTLMISRTP EVTCVVVDVS

151 HEDPEVKFNW YVDGVEVHNA KTKPREEQYN STYRVVSVLT VLHQDWLNGK

201 EYKCKVSNKA LPAPIEKTIS KAKGQPREPQ VYTLPPSRDE LTKNQVSLTC

251 LVKGFYPSDI AVEWESNGQP ENNYKTTPPV LDSDGSFFLY SKLTVDKSRW

301 QQGNVFSCSV MHEALHNHYT QKSLSLSPGK

SEQ ID NO: 56
(human IgG antibody LC κ constant region)
   1 RTVAAPSVFI FPPSDEQLKS GTASVVCLLN NFYPREAKVQ WKVDNALQSG

51 NSQESVTEQD SKDSTYSLSS TLTLSKADYE KHKVYACEVT HQGLSSPVTK

101 SFNRGEC

SEQ ID NO: 57
(HC rabbit leader sequence)
   1 MGWTLVFLFL LSVTAGVHS

SEQ ID NO: 58
(LC rabbit leader sequence)
   1 MVSSAQFLGL LLLCFQGTRC
```

Humanized HCVR amino acid sequences with cysteine mutation at position 41 according to the numbering system of Kabat

```
                                                   SEQ ID NO: 59
(HCVR 825 humanized version 1 41C)
   1 EVQLVESGGD LAQPGGSLRL SCAVSGIDLS SYGMGWVRQA CGKGLEWVSI

51 ISRNSVTYYA TWAKGRFTIS RDNSKNTVYL QMTSLRAEDT ALYFCARRAT

101 YSGALGYFDI WGQGTLVTVS S
```

-continued

SEQ ID NO: 60
(HCVR 825 humanized version 2 41C)
  1 EVQLEESGGG LVKPGGSLRL SCAASGIDLS SYGMGWVRQA CGKGLEWVSI

51 ISRNSVTYYA TWAKGRFTIS RDNSKNTLYL QMNSLRAEDT AVYYCARRAT

101 YSGALGYFDI WGRGTLVTVS S

SEQ ID NO: 61
(HCVR 833 humanized version 1 41C)
  1 EVQLVESGGG LIQPGGSLRL SCAASGIDLS HYVVGWVRQA CGKGLEWVSI

51 IYGSGRTYYA NWAKGRFTIS KDNSKNTLYV RMNSLRAEDT AVYYCARDAS

101 VSVYYWGYFD LWGQGTLVTV SS

SEQ ID NO: 62
(HCVR 833 humanized version 2 41C)
  1 EVQLVESGGG LVQPGGSLRL SCAASGIDLS HYVVGWVRQA CGKGLEWVSI

51 IYGSGRTYYA NWAKGRFTIS RDNSKNTLFL RMNSLRVEDT AVYFCARDAS

101 VSVYYWGYFD LWGQGTLVTV SS

SEQ ID NO: 63
(HCVR 833 humanized version 3 41C)
  1 EVQLEESGGG LVKPGGSLRL SCAASGIDLS HYVVGWVRQA CGKGLEWVSI

51 IYGSGRTYYA NWAKGRFTIS RDNSKNTLYL QMNSLRAEDT AVYYCARDAS

101 VSVYYWGYFD LWGRGTLVTV SS

SEQ ID NO: 64
(HCVR 833 humanized version 4 41C)
  1 QSLEESGGGL VQPGGSLRLS CAASGIDLSH YVVGWVRQAC GKGLEWIGII

51 YGSGRTYYAN WAKGRFTISR HNSKNTLYLQ MNSLRAEDTA VYYCARDASV

101 SVYYWGYFDL WGQGTLVTV SS

---

The invention claimed is:

1. An antibody-drug conjugate comprising an anti-5T4 antibody having a linker drug conjugated thereto:
   wherein said antibody comprises a heavy chain (HC) and light chain (LC) variable region (VR) complementarity determining, regions (CDRs) selected from the group consisting of:
   a. CDR1, CDR2, and CDR3 as shown in SEQ ID NO:1 and CDR1, CDR2, and CDR3 as shown in SEQ ID NO:2;
   b. CDR1, CDR2, and CDR3 as shown in SEQ ID NO:5 and CDR1, CDR2, and CDR3 as shown in SEQ ID NO:6;
   c. CDR1, CDR2, and CDR3 as shown in SEQ ID NO:7 and CDR1, CDR2, and CDR3 as shown in SEQ ID NO:8;
   d. CDR1, CDR2, and CDR3 as shown in SEQ ID NO:11 and CDR1, CDR2, and CDR3 as shown in SEQ ID NO:12;
   e. CDR1, CDR2, and CDR3 as shown in SEQ ID NO:13 and CDR1, CDR2, and CDR3 as shown in SEQ ID NO:14;
   f. CDR1, CDR2, and CDR3 as shown in SEQ ID NO:17 and CDR1, CDR2, and CDR3 as shown in SEQ ID NO:18;
   g. CDR1, CDR2, and CDR3 as shown in SEQ ID NO:19 and CDR1, CDR2, and CDR3 as shown in SEQ ID NO 20;
   h. CDR1, CDR2, and CDR3 as shown in SEQ ID NO:25 and CDR1, CDR2, and CDR3 as shown in SEQ ID NO:26.

2. The antibody-drug conjugate according to claim 1, wherein said linker drug is site-specifically conjugated to the antibody through at least one engineered cysteine.

3. The antibody-drug conjugate according to claim 1, wherein said conjugate is of formula (I)
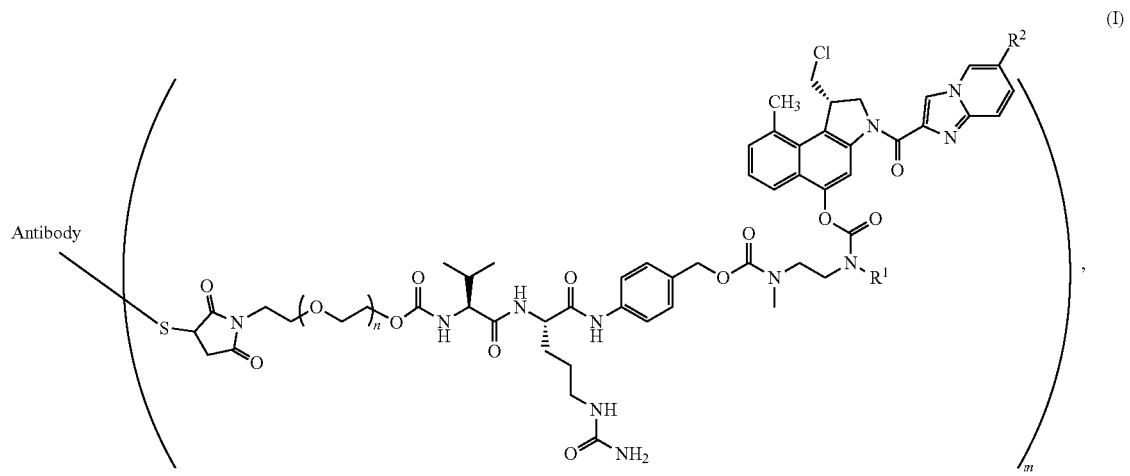
wherein Antibody represents said anti-5T4 antibody,
n is 0-3,
m represents an average DAR of from 1 to 6,
$R^1$ is selected from
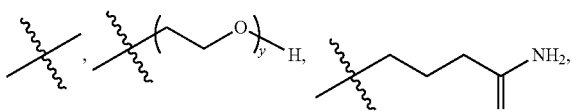
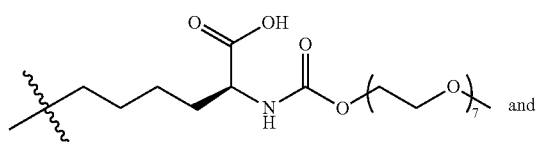
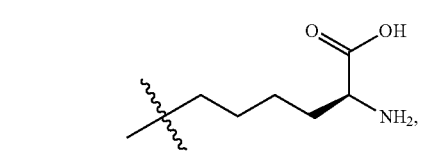
y is 1-16, and
$R^2$ is selected from
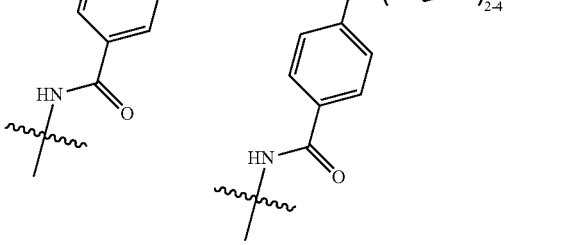
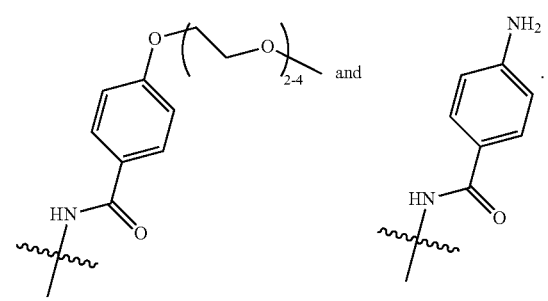

4. The antibody-drug conjugate according to claim 3, wherein n is 0-1, m represents an average DAR of from 1.5 to 2, $R^1$ is

[chemical structure: branched linker with -(O-CH2CH2)y-OH, y is 1-4]

y is 1-4, and $R^2$ is selected from

[chemical structures: para-hydroxybenzamide group, and para-(O-CH2CH2)2-4-OH benzamide group]

5. The antibody-drug conjugate according to claim 1, wherein said conjugate is of formula (II)

[chemical structure of formula (II): Antibody-S-maleimide-PEG-carbamate-Val-Cit-PAB-carbamate-linker-drug (chlorinated CBI-type warhead), with subscript 1.5-2]

(II)

wherein Antibody represents said anti-5T4 antibody.

6. The antibody-drug conjugate according to claim 1, wherein the anti-5T4 antibody is a humanized antibody comprising HCVR and LCVR selected from the group consisting of:
   a. HCVR amino acid sequence of SEQ ID NO:61 and LCVR amino acid sequence of SEQ ID NO:51;
   b. HCVR amino acid sequence of SEQ ID NO:62 and LCVR amino acid sequence of SEQ ID NO:51;
   c. HCVR amino acid sequence of SEQ ID NO:63 and LCVR amino acid sequence of SEQ ID NO:49;
   d. HCVR amino acid sequence of SEQ ID NO:64 and LCVR amino acid sequence of SEQ ID NO:50;
   e. HCVR amino acid sequence of SEQ ID NO:59 and LCVR amino acid sequence of SEQ ID NO:47; and
   f. HCVR amino acid sequence of SEQ ID NO:60 and LCVR amino acid sequence of SEQ ID NO:48;

wherein the linker drug is site-specifically conjugated to the anti-5T4 antibody through the engineered cysteine at heavy chain position 41 (according to Kabat numbering).

7. A pharmaceutical composition comprising the antibody-drug conjugate according to claim 1 and one or more pharmaceutically acceptable excipients.

8. The pharmaceutical composition according to claim 7, wherein said composition is a lyophilized powder.

9. The antibody-drug conjugate according to claim 3, wherein the anti-5T4 antibody is a humanized antibody comprising HCVR and LCVR selected from the group consisting of:
   a. HCVR amino acid sequence of SEQ ID NO:61 and LCVR amino acid sequence of SEQ ID NO:51;
   b. HCVR amino acid sequence of SEQ ID NO:62 and LCVR amino acid sequence of SEQ ID NO:51;
   c. HCVR amino acid sequence of SEQ ID NO:63 and LCVR amino acid sequence of SEQ ID NO:49;
   d. HCVR amino acid sequence of SEQ ID NO:64 and LCVR amino acid sequence of SEQ ID NO:50;
   e. HCVR amino acid sequence of SEQ ID NO:59 and LCVR amino acid sequence of SEQ ID NO:47; and
   f. HCVR amino acid sequence of SEQ ID NO:60 and LCVR amino acid sequence of SEQ ID NO:48;

wherein the linker drug is site-specifically conjugated to the anti-5T4 antibody through the engineered cysteine at heavy chain position 41 (according to Kabat numbering).

10. The antibody-drug conjugate according to claim 5, wherein the anti-5T4 antibody is a humanized antibody comprising HCVR and LCVR selected from the group consisting of:
    a. HCVR amino acid sequence of SEQ ID NO:61 and LCVR amino acid sequence of SEQ ID NO:51;
    b. HCVR amino acid sequence of SEQ ID NO:62 and LCVR amino acid sequence of SEQ ID NO:51;
    c. HCVR amino acid sequence of SEQ ID NO:63 and LCVR amino acid sequence of SEQ ID NO:49;
    d. HCVR amino acid sequence of SEQ ID NO:64 and LCVR amino acid sequence of SEQ ID NO:50;
    e. HCVR amino acid sequence of SEQ ID NO:59 and LCVR amino acid sequence of SEQ ID NO:47; and f. HCVR amino acid sequence of SEQ ID NO:60 and LCVR amino acid sequence of SEQ ID NO:48;

wherein the linker drug is site-specifically conjugated to the anti-5T4 antibody through the engineered cysteine at heavy chain position 41 (according to Kabat numbering).

11. The antibody-drug conjugate according to claim 2, wherein the at least one engineered cysteine is present at one or more positions of said antibody selected from heavy chain 40, 41 and 89 (according to Kabat numbering); and light chain 40 and 41 (according to Kabat numbering).

12. The antibody-drug conjugate according to claim 11, wherein the at least one engineered cysteine is present at heavy chain position 41 (according to Kabat numbering).

13. The antibody-drug conjugate according to claim 12, wherein said antibody comprises a heavy chain (HC) and light chain (LC) variable region (VR) complementarity determining regions (CDRs) selected from the group consisting of:

a. CDR1, CDR2, and CDR3 as shown in SEQ ID NO:1 and CDR1, CDR2, and CDR3 as shown in SEQ ID NO:2;

b. CDR1, CDR2, and CDR3 as shown in SEQ ID NO:5 and CDR1, CDR2, and CDR3 as shown in SEQ ID NO:6; and c. CDR1, CDR2, and CDR3 as shown in SEQ ID NO:11 and CDR1, CDR2, and CDR3 as shown in SEQ ID NO:12.

14. The antibody-drug conjugate according to claim 12, wherein said linker drug comprises a cytotoxic drug selected from the group consisting of duocarmycins, calicheamicins, pyrrolobenzodiazepine dimers, maytansinoids, and auristatins.

15. The antibody-drug conjugate according to claim 10, wherein the anti-5T4 antibody is a humanized antibody comprising HCVR amino acid sequence of SEQ ID NO:61 and LCVR amino acid sequence of SEQ ID NO:51.

16. The antibody-drug conjugate according to claim 10, wherein the anti-5T4 antibody is a humanized antibody comprising HCVR amino acid sequence of SEQ ID NO:62 and LCVR amino acid sequence of SEQ ID NO:51.

17. The antibody-drug conjugate according to claim 10, wherein the anti-5T4 antibody is a humanized antibody comprising HCVR amino acid sequence of SEQ ID NO:63 and LCVR amino acid sequence of SEQ ID NO:49.

18. The antibody-drug conjugate according to claim 10, wherein the anti-5T4 antibody is a humanized antibody comprising HCVR amino acid sequence of SEQ ID NO:64 and LCVR amino acid sequence of SEQ ID NO:50.

19. The antibody-drug conjugate according to claim 10, wherein the anti-5T4 antibody is a humanized antibody comprising HCVR amino acid sequence of SEQ ID NO:59 and LCVR amino acid sequence of SEQ ID NO:47.

20. The antibody-drug conjugate according to claim 10, wherein the anti-5T4 antibody is a humanized antibody comprising HCVR amino acid sequence of SEQ ID NO:60 and LCVR amino acid sequence of SEQ ID NO:48.

* * * * *